(12) United States Patent
Hong et al.

(10) Patent No.: US 8,785,164 B2
(45) Date of Patent: Jul. 22, 2014

(54) EXPRESSION OF CALEOSIN IN RECOMBINANT OLEAGINOUS MICROORGANISMS TO INCREASE OIL CONTENT THEREIN

(75) Inventors: Seung-Pyo Hong, Hockessin, DE (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 84 days.

(21) Appl. No.: 13/478,522

(22) Filed: May 23, 2012

(65) Prior Publication Data

US 2012/0301932 A1    Nov. 29, 2012

Related U.S. Application Data

(60) Provisional application No. 61/490,337, filed on May 26, 2011.

(51) Int. Cl.
*C12P 7/64*    (2006.01)
*C12N 1/00*    (2006.01)

(52) U.S. Cl.
USPC ............... 435/134; 435/254.11; 435/254.2

(58) Field of Classification Search
USPC ................................ 435/134, 254.11, 254.2
See application file for complete search history.

(56) References Cited

U.S. PATENT DOCUMENTS

| | | | |
|---|---|---|---|
| 7,256,014 B2 | 8/2007 | Kinney et al. | |
| 7,666,628 B2 | 2/2010 | Moloney et al. | |
| 2006/0094092 A1* | 5/2006 | Damude et al. | 435/134 |
| 2007/0026484 A1 | 2/2007 | Kinney et al. | |
| 2010/0317072 A1 | 12/2010 | Hong et al. | |

FOREIGN PATENT DOCUMENTS

| | | |
|---|---|---|
| EP | 1952695 A1 | 8/2008 |
| WO | 2009073822 A2 | 6/2009 |
| WO | 2011053169 A1 | 5/2011 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
International Search Report, International Patent Application No. PCT/US2012/03911, Mailed Jul. 27, 2012.
Froissard et al., Heterologous Expression of ATCL01, A Plant Oil Body Protein, Induces Lipid Accumulation in Yeast, FEMS Yeast Research, vol. 9 (2009), pp. 428-438.
Murphy et al., New Insights Into the Mechanisms of Lipid-Body Biogenesis in Plants and Other Organisms, Biochemical Society Transactions, vol. 28, No. 6 (2000), pp. 710-711.
Naested et al., Caleosins: CA2+ Binding Proteins Associated With Lipids Bodies, Plant Molecular Biology, vol. 44 (2000), pp. 463-476.
Pdxleitner et al., A Role for Caleosin in Degradation of Oil-Body Storage Lipid During Seed Germination, The Plant Journal, vol. 47 (2006), pp. 917-933.

* cited by examiner

*Primary Examiner* — Ganapathirama Raghu

(57) ABSTRACT

Recombinant oleaginous microorganisms having increased oil content due to the expression of a caleosin polypeptide are described. A recombinant oleaginous microorganism of the disclosed invention produces at least 25% of its dry cell weight as oil, and comprises a functional polyunsaturated fatty acid (PUFA) biosynthetic pathway and at least one genetic construct encoding a caleosin polypeptide. A method for increasing the amount of oil in a recombinant oleaginous microorganism is also described.

7 Claims, 2 Drawing Sheets

```
AtClo1s      MG-SKTEMMERDAMATVAPYAPVTYHRRARVDLDDRLPKPYMPRALQAPDREHPYGTPGH
             ::  ::::::::::: ::::::::::::::: :::::::::::::::: :::::::::::
cys-AtClo1s  MGCSKTEMMERCAMATVAPYAPVTYCRRARVDLDDCLPKPYMPRALCAPDREHPYGTPGH
                      10        20        30        40        50        60

AtClo1s      KNYGLSVLQQHVSFFDIDDNGIIYPWETYSGIRMLGFNIIGSLIIAAVINLTLSYATLPG
             ::::::::::::::::::::::::::::::::::::::::::::::::::::::::::
cys-AtClo1s  KNYGLSVLQQHVSFFDIDDNGIIYPWETYSGIRMLGFNIIGSLIIAAVINLTLSYATLPG
                      70        80        90       100       110       120

AtClo1s      WLPSPFFPIYIHNIHKSKHGSDSKTYDNEGRFMPVNLELIFSKYAKTLPDKLSLGELWEM
             ::::::::::::::::::::::::::::::::::::::::::::::::::::::::::
cys-AtClo1s  WLPSPFFPIYIHNIHKSKHGSDSKTYDNEGRFMPVNLELIFSKYAKTLPDKLSLGELWEM
                     130       140       150       160       170       180

AtClo1s      TEGNRDAWDIFGWIAGKIEWGLLYLLARDEEGFLSKEAIRRCFDGSLFEYCAKIYAGISE
             ::::::::::::::::::::::: ::::::::::::::::::::::::::::::::::
cys-AtClo1s  TEGNRDAWDIFGWIAGKIEWCLLYLLACDEEGFLSKEAIRRCFDGSLFEYCAKIYAGISE
                     190       200       210       220       230       240

AtClo1s      DKTAYY    (SEQ ID NO:2)
             :::::: 
cys-AtClo1s  CKTAYY    (SEQ ID NO:51)
```

FIG. 2

SEQUENCE LISTING

<160> NUMBER OF SEQ ID NOS: 65

<210> SEQ ID NO 1
<211> LENGTH: 738
<212> TYPE: DNA
<213> ORGANISM: Arabidopsis thaliana

<400> SEQUENCE: 1

```
atggggtcaa agacggagat gatggagaga gacgcaatgg ctacggtggc tccctatgcg      60
ccggtcactt accatcgccg tgctcgtgtt gacttggatg atagacttcc taaaccttat     120
atgccaagag cattgcaagc accagacaga gaacacccgt acggaactcc aggccataag     180
aattacggac ttagtgttct tcaacagcat gtctccttct tcgatatcga tgataatggc     240
atcatttacc cttgggagac ctactctgga ctgcgaatgc ttggtttcaa tatcattggg     300
tcgcttataa tagccgctgt tatcaacctg acccttagct atgccactct tccggggtgg     360
ttaccttcac ctttcttccc tatatacata cacaacatac acaagtcaaa gcatggaagt     420
```

```
gattcaaaaa catatgacaa tgaaggaagg tttatgccgg tgaatcttga gttgatattt      480
agcaaatatg cgaaaacctt gccagacaag ttgagtcttg agaactatg ggagatgaca       540 gaaggaaacc gtgacgcttg ggacattttt ggatggatcg caggcaaaat agagtgggga     600
ctgttgtact tgctagcaag ggatgaagaa gggttttgt caaaagaagc tattaggcgg      660
tgtttcgatg gaagcttgtt cgagtactgt gccaaaatct acgctggtat cagtgaagac     720
aagacagcat actactaa                                                    738
```

<210> SEQ ID NO 2
<211> LENGTH: 245
<212> TYPE: PRT
<213> ORGANISM: Arabidopsis thaliana

<400> SEQUENCE: 2

```
Met Gly Ser Lys Thr Glu Met Met Glu Arg Asp Ala Met Ala Thr Val
1               5                   10                  15

Ala Pro Tyr Ala Pro Val Thr Tyr His Arg Arg Ala Arg Val Asp Leu
            20                  25                  30

Asp Asp Arg Leu Pro Lys Pro Tyr Met Pro Arg Ala Leu Gln Ala Pro
        35                  40                  45

Asp Arg Glu His Pro Tyr Gly Thr Pro Gly His Lys Asn Tyr Gly Leu
    50                  55                  60

Ser Val Leu Gln Gln His Val Ser Phe Phe Asp Ile Asp Asp Asn Gly
65                  70                  75                  80

Ile Ile Tyr Pro Trp Glu Thr Tyr Ser Gly Leu Arg Met Leu Gly Phe
                85                  90                  95

Asn Ile Ile Gly Ser Leu Ile Ile Ala Ala Val Ile Asn Leu Thr Leu
            100                 105                 110

Ser Tyr Ala Thr Leu Pro Gly Trp Leu Pro Ser Pro Phe Phe Pro Ile
        115                 120                 125

Tyr Ile His Asn Ile His Lys Ser Lys His Gly Ser Asp Ser Lys Thr
    130                 135                 140

Tyr Asp Asn Glu Gly Arg Phe Met Pro Val Asn Leu Glu Leu Ile Phe
145                 150                 155                 160

Ser Lys Tyr Ala Lys Thr Leu Pro Asp Lys Leu Ser Leu Gly Glu Leu
                165                 170                 175

Trp Glu Met Thr Glu Gly Asn Arg Asp Ala Trp Asp Ile Phe Gly Trp
            180                 185                 190

Ile Ala Gly Lys Ile Glu Trp Gly Leu Leu Tyr Leu Leu Ala Arg Asp
        195                 200                 205

Glu Glu Gly Phe Leu Ser Lys Glu Ala Ile Arg Arg Cys Phe Asp Gly
    210                 215                 220

Ser Leu Phe Glu Tyr Cys Ala Lys Ile Tyr Ala Gly Ile Ser Glu Asp
225                 230                 235                 240

Lys Thr Ala Tyr Tyr
                245
```

<210> SEQ ID NO 3
<211> LENGTH: 702
<212> TYPE: DNA
<213> ORGANISM: Ricinus communis

<400> SEQUENCE: 3

```
atgggcagtg agatagatga ttcattggct caagctgctc cttatgctcc tgttactttt      60
gagagacctg ttcgtgatga cctggaaact acccttccta agccttatat ggcaagagca     120
```

```
ttggtagctc ctgatacaga acatcctaca ggaacaccag gacataagaa tcacgggctg      180
agtgtgttgc agcagcatgt ggccttcttt gatcaagatg acaatggaat agtttaccct      240
tgggagacat atattgggtt gcgtgcgatt ggttttaata taattgcctc tcttgttatg      300
gccattgtta tcaacgtgtc cttgagctat cctactctcc ctggttggtt tccttcgccc      360
cttttcccca tttacattgg caatatacat aaagccaagc atggcagcga ctcgggaaca      420
tatgacactg aaggacgaca tatgcctgtg aatcttgaaa atatcttcag caagtattct      480
aatacggtgc ctgacaaatt gacattcggg gagctctggg acatgacaga gggacagaga      540
cttgccttcg acatctttgg atggattgca gccaagttag agtggggact cctctatatt      600
cttgcaagag atgaagaagg ttttctgtct aaagaagctg ttcggcgctg ttttgatgga      660
agtttgttcg agtattgtgc taaaatgaac atgggaagat ga                        702
```

<210> SEQ ID NO 4
<211> LENGTH: 233
<212> TYPE: PRT
<213> ORGANISM: Ricinus communis

<400> SEQUENCE: 4

```
Met Gly Ser Glu Ile Asp Asp Ser Leu Ala Gln Ala Ala Pro Tyr Ala
1               5                   10                  15

Pro Val Thr Phe Glu Arg Pro Val Arg Asp Asp Leu Glu Thr Thr Leu
            20                  25                  30

Pro Lys Pro Tyr Met Ala Arg Ala Leu Val Ala Pro Asp Thr Glu His
        35                  40                  45

Pro Thr Gly Thr Pro Gly His Lys Asn His Gly Leu Ser Val Leu Gln
    50                  55                  60

Gln His Val Ala Phe Phe Asp Gln Asp Asp Asn Gly Ile Val Tyr Pro
65                  70                  75                  80

Trp Glu Thr Tyr Ile Gly Leu Arg Ala Ile Gly Phe Asn Ile Ile Ala
                85                  90                  95

Ser Leu Val Met Ala Ile Val Ile Asn Val Ser Leu Ser Tyr Pro Thr
            100                 105                 110

Leu Pro Gly Trp Phe Pro Ser Pro Leu Phe Pro Ile Tyr Ile Gly Asn
        115                 120                 125

Ile His Lys Ala Lys His Gly Ser Asp Ser Gly Thr Tyr Asp Thr Glu
    130                 135                 140

Gly Arg His Met Pro Val Asn Leu Glu Asn Ile Phe Ser Lys Tyr Ser
145                 150                 155                 160

Asn Thr Val Pro Asp Lys Leu Thr Phe Gly Glu Leu Trp Asp Met Thr
                165                 170                 175

Glu Gly Gln Arg Leu Ala Phe Asp Ile Phe Gly Trp Ile Ala Ala Lys
            180                 185                 190

Leu Glu Trp Gly Leu Leu Tyr Ile Leu Ala Arg Asp Glu Glu Gly Phe
        195                 200                 205

Leu Ser Lys Glu Ala Val Arg Arg Cys Phe Asp Gly Ser Leu Phe Glu
    210                 215                 220

Tyr Cys Ala Lys Met Asn Met Gly Arg
225                 230
```

<210> SEQ ID NO 5
<211> LENGTH: 720
<212> TYPE: DNA
<213> ORGANISM: Glycine max

<400> SEQUENCE: 5

```
atggctgcag agatggagag ggagtcattg ataactgaag ctcctaatgc accagttact      60
gcacagagaa gggtcagaaa tgacttagaa aattctctac caaaaccata cttgccaaga     120
gcattgaaag ctcctgatac gggtcaccca aatggaacag caggccacag gcaccacaac     180
ttatctgttc ttcagcagca ttgtgctttt tttgatcaag atgacaatgg aatcatttac     240
ccttgggaaa cttacatggg gctgcgttct attggattta atgttgttgc atctgttatt     300
atggctattg ttatcaatgt tggattgagt taccccactc tacctaattg gttcccttct     360
ctcctttttc ctatctacat acacaacata cacaaagcaa agcatgggag tgactctgga     420
gtttatgaca cagaaggacg ttatgtgcca gcaaatattg agaacatatt cagtaagtat     480
gctcgtacag tacctgacaa gctcacactt ggggagctct gggacttgac agagggaaac     540
cgaaatgctt ttgacatatt tggctggctt gcagcaaaat ttgaatgggg ggttctgtac     600
attctggcaa gggatgagga aggtttcctg tctaaagaag ctgttagaag atgctttgat     660
gggagcttat ttgaatactg tgctaaaatg catactacta gtgatgccaa gatgagttga     720
```

<210> SEQ ID NO 6
<211> LENGTH: 239
<212> TYPE: PRT
<213> ORGANISM: Glycine max

<400> SEQUENCE: 6

```
Met Ala Ala Glu Met Glu Arg Glu Ser Leu Ile Thr Glu Ala Pro Asn
1               5                   10                  15

Ala Pro Val Thr Ala Gln Arg Arg Val Arg Asn Asp Leu Glu Asn Ser
            20                  25                  30

Leu Pro Lys Pro Tyr Leu Pro Arg Ala Leu Lys Ala Pro Asp Thr Gly
        35                  40                  45

His Pro Asn Gly Thr Ala Gly His Arg His His Asn Leu Ser Val Leu
    50                  55                  60

Gln Gln His Cys Ala Phe Phe Asp Gln Asp Asp Asn Gly Ile Ile Tyr
65                  70                  75                  80

Pro Trp Glu Thr Tyr Met Gly Leu Arg Ser Ile Gly Phe Asn Val Val
                85                  90                  95

Ala Ser Val Ile Met Ala Ile Val Ile Asn Val Gly Leu Ser Tyr Pro
            100                 105                 110

Thr Leu Pro Asn Trp Phe Pro Ser Leu Leu Phe Pro Ile Tyr Ile His
        115                 120                 125

Asn Ile His Lys Ala Lys His Gly Ser Asp Ser Gly Val Tyr Asp Thr
    130                 135                 140

Glu Gly Arg Tyr Val Pro Ala Asn Ile Glu Asn Ile Phe Ser Lys Tyr
145                 150                 155                 160

Ala Arg Thr Val Pro Asp Lys Leu Thr Leu Gly Glu Leu Trp Asp Leu
                165                 170                 175

Thr Glu Gly Asn Arg Asn Ala Phe Asp Ile Phe Gly Trp Leu Ala Ala
            180                 185                 190

Lys Phe Glu Trp Gly Val Leu Tyr Ile Leu Ala Arg Asp Glu Glu Gly
        195                 200                 205

Phe Leu Ser Lys Glu Ala Val Arg Arg Cys Phe Asp Gly Ser Leu Phe
    210                 215                 220

Glu Tyr Cys Ala Lys Met His Thr Thr Ser Asp Ala Lys Met Ser
225                 230                 235
```

<210> SEQ ID NO 7
<211> LENGTH: 738
<212> TYPE: DNA
<213> ORGANISM: Sesamum indicum

<400> SEQUENCE: 7

```
atggcaactc atgttttggc tgctgcggcg gagagaaatg ctgcgttggc gccggacgcc      60
ccgcttgctc cggtgactat ggagcgccca gtgcgcactg acttggagac ttcgatcccg     120
aagccctata tggcaagagg attggttgca cctgatatgg atcaccccaa cggaacacca     180
ggccatgtgc atgataattt gagtgtgctg caacagcatt gtgctttctt tgatcaggat     240
gataacggaa tcatctatcc atgggagact tactctggac ttcgccaaat tggtttcaat     300
gtgatagctt cccttataat ggctatcgtc attaatgtgg cgctgagtta tcctactctc     360
ccgggttgga ttccttctcc ttttttcccc atatatttgt acaacataca caaggccaaa     420
catggaagcg actccggaac ctatgatact gaaggaaggt acctaccatat gaattttgag     480
aacctgttca gcaagcatgc ccggacaatg cccgataggc tcactctagg ggagctatgg     540
agcatgactg aagctaacag agaagcattt gacattttcg gctggatcgc aagcaaaatg     600
gagtggactc tcctctacat tcttgcaaga gaccaggacg tttcctgtc gaagaagcc      660
atcaggcggt gttacgatgg cagtttgttc gagtactgtg caaagatgca aggggagcc      720
gaggacaaga tgaaatga                                                   738
```

<210> SEQ ID NO 8
<211> LENGTH: 245
<212> TYPE: PRT
<213> ORGANISM: Sesamum indicum

<400> SEQUENCE: 8

```
Met Ala Thr His Val Leu Ala Ala Ala Glu Arg Asn Ala Ala Leu
1               5                   10                  15

Ala Pro Asp Ala Pro Leu Ala Pro Val Thr Met Glu Arg Pro Val Arg
            20                  25                  30

Thr Asp Leu Glu Thr Ser Ile Pro Lys Pro Tyr Met Ala Arg Gly Leu
        35                  40                  45

Val Ala Pro Asp Met Asp His Pro Asn Gly Thr Pro Gly His Val His
    50                  55                  60

Asp Asn Leu Ser Val Leu Gln Gln His Cys Ala Phe Phe Asp Gln Asp
65                  70                  75                  80

Asp Asn Gly Ile Ile Tyr Pro Trp Glu Thr Tyr Ser Gly Leu Arg Gln
            85                  90                  95

Ile Gly Phe Asn Val Ile Ala Ser Leu Ile Met Ala Ile Val Ile Asn
        100                 105                 110

Val Ala Leu Ser Tyr Pro Thr Leu Pro Gly Trp Ile Pro Ser Pro Phe
    115                 120                 125

Phe Pro Ile Tyr Leu Tyr Asn Ile His Lys Ala Lys His Gly Ser Asp
130                 135                 140

Ser Gly Thr Tyr Asp Thr Glu Gly Arg Tyr Leu Pro Met Asn Phe Glu
145                 150                 155                 160

Asn Leu Phe Ser Lys His Ala Arg Thr Met Pro Asp Arg Leu Thr Leu
            165                 170                 175

Gly Glu Leu Trp Ser Met Thr Glu Ala Asn Arg Glu Ala Phe Asp Ile
        180                 185                 190
```

```
Phe Gly Trp Ile Ala Ser Lys Met Glu Trp Thr Leu Leu Tyr Ile Leu
            195                 200                 205

Ala Arg Asp Gln Asp Gly Phe Leu Ser Lys Glu Ala Ile Arg Arg Cys
210                 215                 220

Tyr Asp Gly Ser Leu Phe Glu Tyr Cys Ala Lys Met Gln Arg Gly Ala
225                 230                 235                 240

Glu Asp Lys Met Lys
                245
```

<210> SEQ ID NO 9
<211> LENGTH: 954
<212> TYPE: DNA
<213> ORGANISM: Coix lacryma

<400> SEQUENCE: 9

```
atgcaggagg cgacgacggc ggcgggcaac aagcagcagg cgcgcagcgg tgaccgcggc        60
gcggcgaaga cggcgacgga tgggaagaag ggcgacgccg acgtggcgaa gggcgacccg       120
gccgccggcg ccaagcaggc tgctggggac gcggggaagg gcggcgccgc cgccaccggc       180
aacaacaagc aggccgcagg cggggccatg catcatcacg gctttcatc ggccgtggag        240
gcgaaggact cccagaccat cgtggcgctg caggcgccgg tgaccgtcac gcgccccgtc       300
cgcggcgacc tcgaggagca cgtccccaag ccatatctgg cgcgagctct ggcggcgccg       360
gacatctacc accccgaggg caccccggaa acgagcaca ggcaccacca catgagcgtg        420
ctgcagcagc acgtcgcctt cttcgaccgc gacgacaacg gcatcatcta cccttgggag       480
acctacagcg gtgccgtgc gcttggggtc aacatggtcc tgtctttctt gatcgctgtc        540
gtcgtgaacg ggaccatgag ctacgccaca ctgcctgggt ggctgccgtc ccctctgttc       600
ccgatctacg tccacaacat ccacaagagc aagcacggca gcgactttgg gacctacgac       660
aacgagggca ggttcatgcc ggtgaacttc gagaacatgt tcagcaagta cgcccgcacg       720
tccccggaca ggctcaccta cagggagctg tggtccatga ccgagggtt ccgcgacgcc        780
ttggatcttt acggctgggt tgcggcgaag ctggagtgga ccatcctgta cgtgctggcg       840
cgggacgacg aggggtacct ggcgcgggag gccatgcgcc gcctgtacga cggcagcctt       900
ttcgagtacg tggagaggca gcggatgcag catgcgcatg ccaagatgtc ctag            954
```

<210> SEQ ID NO 10
<211> LENGTH: 317
<212> TYPE: PRT
<213> ORGANISM: Coix lacryma

<400> SEQUENCE: 10

```
Met Gln Gly Ala Thr Thr Ala Ala Gly Asn Lys Gln Gln Ala Arg Ser
1               5                   10                  15

Gly Asp Arg Gly Ala Ala Lys Thr Ala Thr Asp Gly Lys Lys Gly Asp
            20                  25                  30

Ala Asp Val Ala Lys Gly Asp Pro Ala Ala Gly Ala Lys Gln Ala Ala
        35                  40                  45

Gly Asp Ala Gly Lys Gly Gly Ala Ala Thr Gly Asn Asn Lys Gln
    50                  55                  60

Ala Ala Gly Gly Ala Met His His His Gly Phe Ser Ser Ala Val Glu
65                  70                  75                  80

Ala Lys Asp Ser Gln Thr Ile Val Ala Leu Gln Ala Pro Val Thr Val
                85                  90                  95

Thr Arg Pro Val Arg Gly Asp Leu Glu Glu His Val Pro Lys Pro Tyr
```

```
                100             105             110
Leu Ala Arg Ala Leu Ala Ala Pro Asp Ile Tyr His Pro Glu Gly Thr
            115                 120                 125
Pro Glu Asp Glu His Arg His His His Met Ser Val Leu Gln Gln His
        130                 135                 140
Val Ala Phe Phe Asp Arg Asp Asp Asn Gly Ile Ile Tyr Pro Trp Glu
145                 150                 155                 160
Thr Tyr Ser Gly Cys Arg Ala Leu Gly Phe Asn Met Val Leu Ser Phe
                165                 170                 175
Leu Ile Ala Val Val Asn Gly Thr Met Ser Tyr Ala Thr Leu Pro
            180                 185                 190
Gly Trp Leu Pro Ser Pro Leu Phe Pro Ile Tyr Val His Asn Ile His
        195                 200                 205
Lys Ser Lys His Gly Ser Asp Phe Gly Thr Tyr Asp Asn Glu Gly Arg
    210                 215                 220
Phe Met Pro Val Asn Phe Glu Asn Met Phe Ser Lys Tyr Ala Arg Thr
225                 230                 235                 240
Ser Pro Asp Arg Leu Thr Tyr Arg Glu Leu Trp Ser Met Thr Glu Gly
                245                 250                 255
Phe Arg Asp Ala Leu Asp Leu Tyr Gly Trp Val Ala Ala Lys Leu Glu
            260                 265                 270
Trp Thr Ile Leu Tyr Val Leu Ala Arg Asp Asp Glu Gly Tyr Leu Ala
        275                 280                 285
Arg Glu Ala Met Arg Arg Leu Tyr Asp Gly Ser Leu Phe Glu Tyr Val
    290                 295                 300
Glu Arg Gln Arg Met Gln His Ala His Ala Lys Met Ser
305                 310                 315

<210> SEQ ID NO 11
<211> LENGTH: 849
<212> TYPE: DNA
<213> ORGANISM: Aspergillus niger

<400> SEQUENCE: 11
atgcctcgca aagtctcctt ctccgaaacg caactgccca acttcgacaa acctatccgc      60
ccgccctcaa tcagcgtcga cttctccacc accgccccg aatgcccgt cactgcggcc       120 cgcgagccag cccgctatac gaacgactac attgagaaac ccgtgtccc gcgggccaac      180 accaccgcgt caattgaccg gccggatggg gatgagagct acaccaagca atttagtgac    240 ttcaccccc tccagcaaca tgtcctcttc tgggaccgcg accgcgacgg ccaaatctac      300
ccctgggaca catatatcgg cttccgcgag ctaggattca atatgctgtt ttccttcctg    360
gctgttttga tcatcaacct caacttttcc tatccgactc gtctagcgca ttcgtttctc    420
ccggatccgt ggtttagggt atatgtggat gcggttcata agctaagca tggctccgat     480 agcaatacct acgaccccga aggacgtttt gttcctcaat cgttcgagaa tatgttcgcc   540
aaatatgatc gtgatggtga cggggcattg acactccgcg agctgtttga tatgatgcat    600
ggaaatcggt gcgcggctga tccatttggt tggggagctg caatttgtga atggggcacc   660
acatggttgc tcattgagaa agatggcaaa gtctggaagg aagatgtgcg gggggtttac   720
gatggttcat tgttttggaa ggtccgcgaa gcgaactatt ccggacgggg gtggtcgcag    780
gggttcagac cggggttgtg gatcaaacgg acggtgaagg gggttttgaa tgcatatctg   840
gatggttaa                                                             849
```

<210> SEQ ID NO 12
<211> LENGTH: 282
<212> TYPE: PRT
<213> ORGANISM: Aspergillus niger

<400> SEQUENCE: 12

```
Met Pro Arg Lys Val Ser Phe Ser Glu Thr Gln Leu Pro Asn Phe Asp
1               5                   10                  15

Lys Pro Ile Arg Pro Ser Ile Ser Val Asp Phe Ser Thr Thr Ala
            20                  25                  30

Pro Glu Cys Pro Val Thr Ala Ala Arg Glu Pro Ala Arg Tyr Thr Asn
            35                  40                  45

Asp Tyr Ile Glu Lys Pro Gly Val Pro Arg Ala Asn Thr Thr Ala Ser
        50                  55                  60

Ile Asp Arg Pro Asp Gly Asp Glu Ser Tyr Thr Lys Gln Phe Ser Asp
65                  70                  75                  80

Phe Thr Pro Leu Gln Gln His Val Leu Phe Trp Asp Arg Asp Arg Asp
                85                  90                  95

Gly Gln Ile Tyr Pro Trp Asp Thr Tyr Ile Gly Phe Arg Glu Leu Gly
            100                 105                 110

Phe Asn Met Leu Phe Ser Phe Leu Ala Val Leu Ile Ile Asn Leu Asn
        115                 120                 125

Phe Ser Tyr Pro Thr Arg Leu Ala His Ser Phe Leu Pro Asp Pro Trp
    130                 135                 140

Phe Arg Val Tyr Val Asp Ala Val His Lys Ala Lys His Gly Ser Asp
145                 150                 155                 160

Ser Asn Thr Tyr Asp Pro Glu Gly Arg Phe Val Pro Gln Ser Phe Glu
                165                 170                 175

Asn Met Phe Ala Lys Tyr Asp Arg Asp Gly Asp Gly Ala Leu Thr Leu
            180                 185                 190

Arg Glu Leu Phe Asp Met Met His Gly Asn Arg Cys Ala Ala Asp Pro
        195                 200                 205

Phe Gly Trp Gly Ala Ala Ile Cys Glu Trp Gly Thr Thr Trp Leu Leu
    210                 215                 220

Ile Glu Lys Asp Gly Lys Val Trp Lys Glu Asp Val Arg Gly Val Tyr
225                 230                 235                 240

Asp Gly Ser Leu Phe Trp Lys Val Arg Glu Ala Asn Tyr Ser Gly Arg
                245                 250                 255

Gly Trp Ser Gln Gly Phe Arg Pro Gly Leu Trp Ile Lys Arg Thr Val
            260                 265                 270

Lys Gly Val Leu Asn Ala Tyr Leu Asp Gly
        275                 280
```

<210> SEQ ID NO 13
<211> LENGTH: 900
<212> TYPE: DNA
<213> ORGANISM: Neurospora crassa

<400> SEQUENCE: 13

| | | | | |
|---|---|---|---|---|
| atgccggtca | gagtggttcc | cagagaagat | gaacaggtcg | acgacgaaag acaaggcgtc | 60 |
| gactttgcta | ccgccgtctc | caactgtcct | cccacggccg | agcgtcccca agcaatcgac | 120 |
| atcgacgtcg | acatctacaa | gcctagcatc | gctcgcgcga | atgtggcccc ctcgaccgag | 180 |
| cagcccgagg | gcagtgccga | atatgtcgac | gccctagacc | tcaaggacta caccgtcctc | 240 |
| caacaacact | gcatgttttg | ggaccgcgac | agggatggcg | taatctggcc ccaagacacc | 300 |

```
ttcattggct tctacgaact cggcttcaac ctcttttct gctttttagc gacactcgtc      360
atcaacctca acttctcgta cccaacccgt ctcggtgtct cctacatccc cgaccctat      420 ttccggctgt acctgccgtc catgcacaag gccaagcacg gctcggactc gggcacgtac      480
gacaaggaag gccgcttcgt gccgcaggcg tttgaggaca tgttcagcaa gtgggacagg      540
ggcgacaagg gcgcgctgtc ggcgggcgag ctctggaaca tgatagcggc caacaggctc      600
gctgcggacc cgttcggctg gctgcgggc atctttgagt ttggcgtaac ctggttgttg       660
gtgcagcagg acgggatggt ggacaaggag gatttaagga ggatttacga tggctccatg      720
ttcttcaaaa tcagggaggc ctaccgcacc gaaaagggat ggaacaaggg tttcggcctc      780
tgcgagttct ttaacctggg ccgggagcag tgggctaaga acaagggcag gattccaccg      840
ttgaacggca ttgtcagtaa ggttgagagg agtgttacgc aaaagttgca cagggcctga      900
```

<210> SEQ ID NO 14
<211> LENGTH: 299
<212> TYPE: PRT
<213> ORGANISM: Neurospora crassa

<400> SEQUENCE: 14

```
Met Pro Val Arg Val Pro Arg Glu Asp Glu Gln Val Asp Asp Glu
1               5                   10                  15

Arg Gln Gly Val Asp Phe Ala Thr Ala Val Ser Asn Cys Pro Pro Thr
            20                  25                  30

Ala Glu Arg Pro Gln Ala Ile Asp Ile Asp Val Asp Ile Tyr Lys Pro
        35                  40                  45

Ser Ile Ala Arg Ala Asn Val Ala Pro Ser Thr Glu Gln Pro Glu Gly
    50                  55                  60

Ser Ala Glu Tyr Val Asp Ala Leu Asp Leu Lys Asp Tyr Thr Val Leu
65                  70                  75                  80

Gln Gln His Cys Met Phe Trp Asp Arg Asp Arg Asp Gly Val Ile Trp
                85                  90                  95

Pro Gln Asp Thr Phe Ile Gly Phe Tyr Glu Leu Gly Phe Asn Leu Phe
            100                 105                 110

Phe Cys Phe Leu Ala Thr Leu Val Ile Asn Leu Asn Phe Ser Tyr Pro
        115                 120                 125

Thr Arg Leu Gly Val Ser Tyr Ile Pro Asp Pro Tyr Phe Arg Leu Tyr
    130                 135                 140

Leu Pro Ser Met His Lys Ala Lys His Gly Ser Asp Ser Gly Thr Tyr
145                 150                 155                 160

Asp Lys Glu Gly Arg Phe Val Pro Gln Ala Phe Glu Asp Met Phe Ser
                165                 170                 175

Lys Trp Asp Arg Gly Asp Lys Gly Ala Leu Ser Ala Gly Glu Leu Trp
            180                 185                 190

Asn Met Ile Ala Ala Asn Arg Leu Ala Ala Asp Pro Phe Gly Trp Ala
        195                 200                 205

Ala Gly Ile Phe Glu Phe Gly Val Thr Trp Leu Leu Val Gln Gln Asp
    210                 215                 220

Gly Met Val Asp Lys Glu Asp Leu Arg Arg Ile Tyr Asp Gly Ser Met
225                 230                 235                 240

Phe Phe Lys Ile Arg Glu Ala Tyr Arg Thr Glu Lys Gly Trp Asn Lys
                245                 250                 255

Gly Phe Gly Leu Cys Glu Phe Phe Asn Leu Gly Arg Glu Gln Trp Ala
            260                 265                 270
```

Lys Asn Lys Gly Arg Ile Pro Pro Leu Asn Gly Ile Val Ser Lys Val
              275                 280                 285

Glu Arg Ser Val Thr Gln Lys Leu His Arg Ala
        290                 295

<210> SEQ ID NO 15
<211> LENGTH: 732
<212> TYPE: DNA
<213> ORGANISM: Arabidopsis thaliana

<400> SEQUENCE: 15

```
atgacgtcga tggagaggat ggagagagac gcaatggaga cggtggctcc atacgctcgg     60
gtgacttatc accgccgtgt tcgtggtgac ttggatgaca cacttcctaa accttatttg    120
ccgagagcac tacaagcacc tgacatggaa cacccacaag gaacaccaga tcatagacat    180
aatggcctta gtgttcttca gcaacatgtc gctttcttcg atttggacaa taatggcatc    240
atttatccct tgaaaccttt ctctgggttc cggttactcg gtttcaattt actcgcgtcg    300
cttatcttgg ctgctggtat caacatagct cttagctatg ctactctccc gggatggtta    360
ccgtctccgt tcttccctat atatattcac aacattcaca aggcaaagca cggaagcgac    420
tctaaaacat atgacaatga aggaaggtat acaccagcga atcttgagtt gatgtttagc    480
aaatacgcga ggaccatacc agacaagttg agtcttggag agctatggga catgaccgaa    540
ggaaaccgcg atgcctttga cttttttgga tggttagcga gcaaagtgga atggggtgta    600
ttgtatgcat tagcgagtga tgaagaagga ttccttgtcta aagaagccat aaggcggtgc    660
ttcgatggga gcttgttcga gtattgtgcc aagaactacg ctgagatcaa ggagtacaag    720
acgtactact ga                                                        732
```

<210> SEQ ID NO 16
<211> LENGTH: 243
<212> TYPE: PRT
<213> ORGANISM: Arabidopsis thaliana

<400> SEQUENCE: 16

Met Thr Ser Met Glu Arg Met Glu Arg Asp Ala Met Glu Thr Val Ala
1               5                  10                  15

Pro Tyr Ala Arg Val Thr Tyr His Arg Arg Val Arg Gly Asp Leu Asp
            20                  25                  30

Asp Thr Leu Pro Lys Pro Tyr Leu Pro Arg Ala Leu Gln Ala Pro Asp
        35                  40                  45

Met Glu His Pro Gln Gly Thr Pro Asp His Arg His Asn Gly Leu Ser
    50                  55                  60

Val Leu Gln Gln His Val Ala Phe Phe Asp Leu Asp Asn Asn Gly Ile
65                  70                  75                  80

Ile Tyr Pro Phe Glu Thr Phe Ser Gly Phe Arg Leu Leu Gly Phe Asn
                85                  90                  95

Leu Leu Ala Ser Leu Ile Leu Ala Ala Gly Ile Asn Ile Ala Leu Ser
            100                 105                 110

Tyr Ala Thr Leu Pro Gly Trp Leu Pro Ser Pro Phe Phe Pro Ile Tyr
        115                 120                 125

Ile His Asn Ile His Lys Ala Lys His Gly Ser Asp Ser Lys Thr Tyr
    130                 135                 140

Asp Asn Glu Gly Arg Tyr Thr Pro Ala Asn Leu Glu Leu Met Phe Ser
145                 150                 155                 160

```
Lys Tyr Ala Arg Thr Ile Pro Asp Lys Leu Ser Leu Gly Glu Leu Trp
            165                 170                 175

Asp Met Thr Glu Gly Asn Arg Asp Ala Phe Asp Phe Phe Gly Trp Leu
        180                 185                 190

Ala Ser Lys Val Glu Trp Gly Val Leu Tyr Ala Leu Ala Ser Asp Glu
    195                 200                 205

Glu Gly Phe Leu Ser Lys Glu Ala Ile Arg Arg Cys Phe Asp Gly Ser
210                 215                 220

Leu Phe Glu Tyr Cys Ala Lys Asn Tyr Ala Glu Ile Lys Glu Tyr Lys
225                 230                 235                 240

Thr Tyr Tyr

<210> SEQ ID NO 17
<211> LENGTH: 585
<212> TYPE: DNA
<213> ORGANISM: Arabidopsis thaliana

<400> SEQUENCE: 17
atggcaggag aggcagaggc tttggccacg acggcaccgt tagctccggt caccagtcag      60
cgaaaagtac ggaacgattt ggaggaaaca ttaccaaaac catacatggc aagagcatta     120
gcagctccag atacagagca tccgaatgga acagaaggtc acgatagcaa aggaatgagt     180
gttatgcaac aacatgttgc tttcttcgac caaaacgacg atggaatcgt ctatccttgg     240
gagacttata agggatttcg tgaccttggt ttcaacccaa tttcctctat cttttggacc     300
ttactcataa acttagcgtt cagctacgtt acacttccga gttgggtgcc atcaccatta     360
ttgccggttt atatcgacaa catacacaaa gccaagcatg ggagtgattc gagcacctat     420
gacaccgaag gaaggctttc aaacaaagtt gaatggatac tactctatat tcttgctaag     480
gacgaagatg gtttcctatc taagaagct gtgagaggtt gctttgatgg aagtttattt     540
gaacaaattg ccaagagag ggccaattct cgcaaacaag actaa                      585

<210> SEQ ID NO 18
<211> LENGTH: 194
<212> TYPE: PRT
<213> ORGANISM: Arabidopsis thaliana

<400> SEQUENCE: 18

Met Ala Gly Glu Ala Glu Ala Leu Ala Thr Thr Ala Pro Leu Ala Pro
1               5                   10                  15

Val Thr Ser Gln Arg Lys Val Arg Asn Asp Leu Glu Glu Thr Leu Pro
            20                  25                  30

Lys Pro Tyr Met Ala Arg Ala Leu Ala Ala Pro Asp Thr Glu His Pro
        35                  40                  45

Asn Gly Thr Glu Gly His Asp Ser Lys Gly Met Ser Val Met Gln Gln
    50                  55                  60

His Val Ala Phe Phe Asp Gln Asn Asp Asp Gly Ile Val Tyr Pro Trp
65                  70                  75                  80

Glu Thr Tyr Lys Gly Phe Arg Asp Leu Gly Phe Asn Pro Ile Ser Ser
                85                  90                  95

Ile Phe Trp Thr Leu Leu Ile Asn Leu Ala Phe Ser Tyr Val Thr Leu
            100                 105                 110

Pro Ser Trp Val Pro Ser Pro Leu Leu Pro Val Tyr Ile Asp Asn Ile
        115                 120                 125

His Lys Ala Lys His Gly Ser Asp Ser Ser Thr Tyr Asp Thr Glu Gly
    130                 135                 140
```

Arg Leu Ser Asn Lys Val Glu Trp Ile Leu Leu Tyr Ile Leu Ala Lys
145                 150                 155                 160

Asp Glu Asp Gly Phe Leu Ser Lys Glu Ala Val Arg Gly Cys Phe Asp
                165                 170                 175

Gly Ser Leu Phe Glu Gln Ile Ala Lys Glu Arg Ala Asn Ser Arg Lys
            180                 185                 190

Gln Asp

<210> SEQ ID NO 19
<211> LENGTH: 588
<212> TYPE: DNA
<213> ORGANISM: Arabidopsis thaliana

<400> SEQUENCE: 19
atggcttcct ctatttccac tggagtgaaa tttgttccag aagaagataa tttcttgcag        60
agacatgtcg ctttttttcga taggaacaaa gatggtatcg tttatccctc ggagacattt      120
caaggattta gagcaattgg gtgtggatat ttgttgtcag cagtcgcttc tgtgttcata      180
aacataggtc tcagcagcaa aactcgtccg ggtaaaggat ctctatctg gtttcctata       240 gaggttaaga atattcacct tgccaaacac ggaagcgatt caggcgttta cgacaaagat      300
ggacggtttg ttgcttcgaa gtttgaggag atatttacga agcatgcaca cacacatcgc      360
gatgctttga ccaacgagga actcaaacaa ctcctaaagg caaacaaaga acctaatgat      420
cgtaaaggat ggcttgcagg gtatacggag tggaaggtat tgcattattt gtgtaaagac      480
aagaatggtt tgttgcacaa agacacagtg agagctgcct acgatggttc tcttttcgaa      540
aaactcgaga acaaagatc ttctaaaact tctaagaaac atccataa                    588

<210> SEQ ID NO 20
<211> LENGTH: 195
<212> TYPE: PRT
<213> ORGANISM: Arabidopsis thaliana

<400> SEQUENCE: 20

Met Ala Ser Ser Ile Ser Thr Gly Val Lys Phe Val Pro Glu Glu Asp
1               5                   10                  15

Asn Phe Leu Gln Arg His Val Ala Phe Phe Asp Arg Asn Lys Asp Gly
                20                  25                  30

Ile Val Tyr Pro Ser Glu Thr Phe Gln Gly Phe Arg Ala Ile Gly Cys
            35                  40                  45

Gly Tyr Leu Leu Ser Ala Val Ala Ser Val Phe Ile Asn Ile Gly Leu
        50                  55                  60

Ser Ser Lys Thr Arg Pro Gly Lys Gly Phe Ser Ile Trp Phe Pro Ile
65                  70                  75                  80

Glu Val Lys Asn Ile His Leu Ala Lys His Gly Ser Asp Ser Gly Val
                85                  90                  95

Tyr Asp Lys Asp Gly Arg Phe Val Ala Ser Lys Phe Glu Glu Ile Phe
            100                 105                 110

Thr Lys His Ala His Thr His Arg Asp Ala Leu Thr Asn Glu Glu Leu
        115                 120                 125

Lys Gln Leu Leu Lys Ala Asn Lys Glu Pro Asn Asp Arg Lys Gly Trp
    130                 135                 140

Leu Ala Gly Tyr Thr Glu Trp Lys Val Leu His Tyr Leu Cys Lys Asp
145                 150                 155                 160

Lys Asn Gly Leu Leu His Lys Asp Thr Val Arg Ala Ala Tyr Asp Gly

```
                     165                 170                 175
Ser Leu Phe Glu Lys Leu Glu Lys Gln Arg Ser Ser Lys Thr Ser Lys
            180                 185                 190

Lys His Pro
        195

<210> SEQ ID NO 21
<211> LENGTH: 555
<212> TYPE: DNA
<213> ORGANISM: Arabidopsis thaliana

<400> SEQUENCE: 21
atgactgcat tggagaaaca tgtttccttc ttcgacagga caaagacgg caccgtttat    60 ccatgggaaa cctaccaagg atttagagcg ctcgggacag gcgtctttt ggcggctttt   120 gttgctatat tcatcaacat gggactcagc aagaaaactc gtccgggaaa gggattctcg   180
ccgttgtttc aatagacgt gaagaatagt cacctttgca tgcacggtag tgacaccgac   240
gtctatgacg atgacggaag atttgtggaa tcaaaattcg aggaaatatt caacaagcat   300
gctcgcacac ataaagatgc tctcactgca gaggaaattc aaaaaatgct taagactaac   360
agggatcctt tcgatatcac aggatggctt tcagattatg gagaatggaa aatattacat   420
acgttagctc aagacaaaaa tggtttgtta tcggaaaaga gcgtcagggc catctacgat   480
ggtagccttt tccaccaact ggagaaaaaa agatcttctt cttcttctcg tggcaagaaa   540
caaaaactac cataa                                                    555

<210> SEQ ID NO 22
<211> LENGTH: 184
<212> TYPE: PRT
<213> ORGANISM: Arabidopsis thaliana

<400> SEQUENCE: 22

Met Thr Ala Leu Glu Lys His Val Ser Phe Phe Asp Arg Asn Lys Asp
1               5                   10                  15

Gly Thr Val Tyr Pro Trp Glu Thr Tyr Gln Gly Phe Arg Ala Leu Gly
            20                  25                  30

Thr Gly Arg Leu Leu Ala Ala Phe Val Ala Ile Phe Ile Asn Met Gly
        35                  40                  45

Leu Ser Lys Lys Thr Arg Pro Gly Lys Gly Phe Ser Pro Leu Phe Pro
    50                  55                  60

Ile Asp Val Lys Asn Ser His Leu Cys Met His Gly Ser Asp Thr Asp
65                  70                  75                  80

Val Tyr Asp Asp Asp Gly Arg Phe Val Glu Ser Lys Phe Glu Glu Ile
                85                  90                  95

Phe Asn Lys His Ala Arg Thr His Lys Asp Ala Leu Thr Ala Glu Glu
            100                 105                 110

Ile Gln Lys Met Leu Lys Thr Asn Arg Asp Pro Phe Asp Ile Thr Gly
        115                 120                 125

Trp Leu Ser Asp Tyr Gly Glu Trp Lys Ile Leu His Thr Leu Ala Gln
    130                 135                 140

Asp Lys Asn Gly Leu Leu Ser Glu Lys Ser Val Arg Ala Ile Tyr Asp
145                 150                 155                 160

Gly Ser Leu Phe His Gln Leu Glu Lys Lys Arg Ser Ser Ser Ser Ser
                165                 170                 175

Arg Gly Lys Lys Gln Lys Leu Pro
            180
```

<210> SEQ ID NO 23
<211> LENGTH: 963
<212> TYPE: DNA
<213> ORGANISM: Hordeum vulgare

<400> SEQUENCE: 23

```
ccggcctccg taacgtacag acacagcgac cgggcgtcat ggcgggggag gatgccacta      60
gggcggcgac ggaagaagag ctgtcgtcgg tggcggaggc ggcgccggtg acggcccagc     120
ggccggtccg gtcggacctg gagaagtaca tcccaaagcc atacctggct cgagctctgg     180
tggcgccgga cgtgtaccat cctcaaggga gcaaggagcg cgggcacgag caccgccaca     240
ggagcgtgct gcagcagcac gtagccttct tcgacatgga tggcgacggc gtcatctacc     300
catgggaaac ttaccaagga ctgagggcgc tgggcttcaa catgatcgtg tccttcgtca     360
tcgtcataat catacatgct actctcagct acacaactct gcctactggg taccgtctct     420
ctcttccatt ctacatcgac aacatccaca gggccaagca tggcagcgac accgcgactt     480
acgacaccga gggaaggtac atgccggtga attttgagaa catattcagc aagaacgccc     540
gctggtcacc ggacaagctc acattccggg agatttggac gatgaccgac gaccagcggc     600
aggcgaacga cccatttgga tgggtggcga gcaaggcgga gtggatactg ctgtacatgc     660
tcgccaagga cgaggagggg aaccttccca gagaggctat ccgccgctgc ttcgacggta     720
gcctgttcga gttcatcgcc gacgagagga ggcaggcgca cgggaagcag tactagcctg     780
cgtgcaacgc tgtcggcccg gccggaatgc atgtcttcgt gtctaaaact gtggactggc     840
taccatctca tgtatgccta atgctaataa gttgtgccct cctcaaagtt tcatcagaac     900
aagaaacatc gtcgttttca ataataattt tgttttttct ctataaaaaa aaaaaaaaaa     960
aaa                                                                    963
```

<210> SEQ ID NO 24
<211> LENGTH: 245
<212> TYPE: PRT
<213> ORGANISM: Hordeum vulgare

<400> SEQUENCE: 24

```
Met Ala Gly Glu Asp Ala Thr Arg Ala Ala Thr Glu Glu Leu Ser
1               5                   10                  15

Ser Val Ala Glu Ala Ala Pro Val Thr Ala Gln Arg Pro Val Arg Ser
                20                  25                  30

Asp Leu Glu Lys Tyr Ile Pro Lys Pro Tyr Leu Ala Arg Ala Leu Val
            35                  40                  45

Ala Pro Asp Val Tyr His Pro Gln Gly Ser Lys Glu Arg Gly His Glu
        50                  55                  60

His Arg His Arg Ser Val Leu Gln Gln His Val Ala Phe Phe Asp Met
65                  70                  75                  80

Asp Gly Asp Gly Val Ile Tyr Pro Trp Glu Thr Tyr Gln Gly Leu Arg
                85                  90                  95

Ala Leu Gly Phe Asn Met Ile Val Ser Phe Val Ile Val Ile Ile Ile
            100                 105                 110

His Ala Thr Leu Ser Tyr Thr Thr Leu Pro Thr Gly Tyr Arg Leu Ser
        115                 120                 125

Leu Pro Phe Tyr Ile Asp Asn Ile His Arg Ala Lys His Gly Ser Asp
    130                 135                 140

Thr Ala Thr Tyr Asp Thr Glu Gly Arg Tyr Met Pro Val Asn Phe Glu
```

```
                145                 150                 155                 160
Asn Ile Phe Ser Lys Asn Ala Arg Trp Ser Pro Asp Lys Leu Thr Phe
                    165                 170                 175

Arg Glu Ile Trp Thr Met Thr Asp Asp Gln Arg Gln Ala Asn Asp Pro
                    180                 185                 190

Phe Gly Trp Val Ala Ser Lys Ala Glu Trp Ile Leu Leu Tyr Met Leu
                    195                 200                 205

Ala Lys Asp Glu Glu Gly Asn Leu Pro Arg Glu Ala Ile Arg Arg Cys
    210                 215                 220

Phe Asp Gly Ser Leu Phe Glu Phe Ile Ala Asp Glu Arg Arg Gln Ala
225                 230                 235                 240

His Gly Lys Gln Tyr
                245

<210> SEQ ID NO 25
<211> LENGTH: 615
<212> TYPE: DNA
<213> ORGANISM: Fagus sylvatica

<400> SEQUENCE: 25
atggcctctt catctccatc ttcgaattat attcaggaag catcgggtgg acatatcata      60
ccaactgatc agaacgtcct gcagaaacat gttgcattct ttgataggaa tcaggatggc     120
atagtttatc cttcggaaac ttttaaagga tttcgtgcaa ttggatgtgg tatcttttc     180 tctgctatca gtgccatctt catcaacttc ggtctcagcc agaaaacccg tccgggaaaa     240
tttccttctc tcctctttcc aattgaggtt aagaatattc aaaaagccaa acatgggagc     300
gactctggtg tctatgatac cgaaggaagg tttgttcctt cgaagtttga agagattttc     360
agcaagcatg ctctttctta ccccagtgct ttaacatcgg atgaacttat gaaaatgctg     420
aaggaaaata gggtccccaa ggactacaga ggatggcttg caagctgggc agaatggaag     480
accctatata ttctctgcaa ggacaagaag tgggttacta cagaaagaaa caagttaaag     540
ctgcttatga tggaagcttg gttgaaagaa atggagaagg aaagatcatc agctaaaaag     600
aaagctgttg tttaa                                                     615

<210> SEQ ID NO 26
<211> LENGTH: 204
<212> TYPE: PRT
<213> ORGANISM: Fagus sylvatica

<400> SEQUENCE: 26

Met Ala Ser Ser Ser Pro Ser Ser Asn Tyr Ile Gln Glu Ala Ser Gly
1               5                   10                  15

Gly His Ile Ile Pro Thr Asp Gln Asn Val Leu Gln Lys His Val Ala
                20                  25                  30

Phe Phe Asp Arg Asn Gln Asp Gly Ile Val Tyr Pro Ser Glu Thr Phe
            35                  40                  45

Lys Gly Phe Arg Ala Ile Gly Cys Gly Ile Phe Ser Ala Ile Ser
        50                  55                  60

Ala Ile Phe Ile Asn Phe Gly Leu Ser Gln Lys Thr Arg Pro Gly Lys
65                  70                  75                  80

Phe Pro Ser Leu Leu Phe Pro Ile Glu Val Lys Asn Ile Gln Lys Ala
                85                  90                  95

Lys His Gly Ser Asp Ser Gly Val Tyr Asp Thr Glu Gly Arg Phe Val
            100                 105                 110
```

Pro Ser Lys Phe Glu Glu Ile Phe Ser Lys His Ala Leu Ser Tyr Pro
            115                 120                 125

Ser Ala Leu Thr Ser Asp Glu Leu Met Lys Met Leu Lys Glu Asn Arg
        130                 135                 140

Val Pro Lys Asp Tyr Arg Gly Trp Leu Ala Ser Trp Ala Glu Trp Lys
145                 150                 155                 160

Thr Leu Tyr Ile Leu Cys Lys Asp Lys Lys Trp Val Thr Thr Glu Arg
                165                 170                 175

Asn Lys Leu Lys Leu Leu Met Met Glu Ala Trp Leu Lys Glu Met Glu
            180                 185                 190

Lys Glu Arg Ser Ser Ala Lys Lys Lys Ala Val Val
        195                 200

<210> SEQ ID NO 27
<211> LENGTH: 627
<212> TYPE: DNA
<213> ORGANISM: Cynodon dactylon

<400> SEQUENCE: 27
atggcagcca aatcttcaga gaaagggagc aacaacggca agagtcctc catggcggac      60
gtctaccgcg gcgaactcac gccgctgcag aggcacgtcg ccttcttcga ccggaacaag     120
gacggcgtca tctaccccgc cgagacgtac gaaggcttcc gagcaatcgg cgccggcgtc     180
ccgctctccg ccgtaggagc agccttcgtc aacggcttcc ttggacccaa gacgatcccg     240
gagaacgaga aggttggacc tttcaagttt ccaatttatg tcaagaacat cctcaagggc     300
aagcacggaa gcgattcagg cgtatacgat gcccatggaa ggtttgttcc gaaaagtttt     360
gaggagattt tcaagaagca tgcccatacc aggcctgacg ccctaacggc caagagctg      420
caggaactgc tccaggcgaa cagggaacct aaagatttca ggggatggtt agggggcttc     480
acggagtgga aggtgctgta tgccctttgc aaagataagg acgggtttct tcacaaggat     540
actgtcaagg ctgtctatga tggcagcttg tttgataaga tggagcaaga gaggaaagcc     600
aagaaggaat ctgctaagaa gaaatga                                        627

<210> SEQ ID NO 28
<211> LENGTH: 208
<212> TYPE: PRT
<213> ORGANISM: Cynodon dactylon

<400> SEQUENCE: 28

Met Ala Ala Lys Ser Ser Glu Lys Gly Ser Asn Asn Gly Lys Glu Ser
1               5                   10                  15

Ser Met Ala Asp Val Tyr Arg Gly Glu Leu Thr Pro Leu Gln Arg His
            20                  25                  30

Val Ala Phe Phe Asp Arg Asn Lys Asp Gly Val Ile Tyr Pro Ala Glu
        35                  40                  45

Thr Tyr Glu Gly Phe Arg Ala Ile Gly Ala Gly Val Pro Leu Ser Ala
    50                  55                  60

Val Gly Ala Ala Phe Val Asn Gly Phe Leu Gly Pro Lys Thr Ile Pro
65                  70                  75                  80

Glu Asn Glu Lys Val Gly Pro Phe Lys Phe Pro Ile Tyr Val Lys Asn
                85                  90                  95

Ile Leu Lys Gly Lys His Gly Ser Asp Ser Gly Val Tyr Asp Ala His
            100                 105                 110

Gly Arg Phe Val Pro Glu Lys Phe Glu Glu Ile Phe Lys Lys His Ala
        115                 120                 125

```
His Thr Arg Pro Asp Ala Leu Thr Ala Lys Glu Leu Gln Glu Leu Leu
    130                 135                 140

Gln Ala Asn Arg Glu Pro Lys Asp Phe Arg Gly Trp Leu Gly Gly Phe
145                 150                 155                 160

Thr Glu Trp Lys Val Leu Tyr Ala Leu Cys Lys Asp Lys Asp Gly Phe
                165                 170                 175

Leu His Lys Asp Thr Val Lys Ala Val Tyr Asp Gly Ser Leu Phe Asp
                180                 185                 190

Lys Met Glu Gln Glu Arg Lys Ala Lys Lys Glu Ser Ala Lys Lys Lys
            195                 200                 205

<210> SEQ ID NO 29
<211> LENGTH: 1137
<212> TYPE: DNA
<213> ORGANISM: Aspergillus nidulans

<400> SEQUENCE: 29
atgccatcgt cccaacctgc gagttcccat ataaccaccg caccgccaaa ggctgtcaag      60
ccattggctt cgaagtcaaa gccattggag cctaaggcgc ccgaatcaaa gcccagtgac     120
tcgaatgtgc ctgagccagt ggagccagag gccaaggcac cggagacaaa gtctttcaag     180
gaggctctag tgaacggtgc cggtgatggt gataagcaaa ccgacagctc gaactcgact     240
tcaccgtcgt ctttccagtc cgattctatc agggatagca gccctaatac ctcacgatcg     300
aactccagtt ccagttccca gcctacgaaa gaagagaccg acaaagacac tgagaagaac     360
atcaaggaaa ggaacaaaca agaacaagaa aaagacacta ccaccatccc catcgtatcc     420
aaacactgcg ccgtgacctc caagcgcctc ccagcaacaa atgtctcaat gaaaagtcc      480 ggcgttgctc gatgcaatgt tgtcgatggc gctacctctg atacctccat aaaggatttc     540
catgaataca cacccatgca acaacatatc ctcttctggg accgcgaccg cgacggccag     600
atctacccat atgatacgta ccggggcttc cgggacttgg gcttcaacat cctcttctcc     660
ttcctcgccg tgctgattat caatctgaac ttctcgtacc cgacacggct cgcgcactcg     720
tttctcccgg atcccgtttc agagtttac gtggatagca tctacaaggc gaaacatgga     780
tccgactctg gtagttttga tgccgaaggc cgctttatcc cgcagcattt cgaggacatg     840
tttgccaagt acgatggaga tcaggacgga gcgctgacgt ttggggaatt gtttaatatg     900
atgcacggga accggtgtgc ggcagatccg tttgggtggg gcgccgcttt cttcgaatgg     960
gtcacaacgt ggctgcttat ccagaaggac ggaaaagttt acaaggacga tttactcggt    1020
gtatatgatg gttcgctgtt ctggaagatc gccaaggcga gaagtctccc ccagggctgg    1080
tcccagggat tcgggttggg cggagatggc tttcttgggg gtgttaaagt gatttaa      1137

<210> SEQ ID NO 30
<211> LENGTH: 378
<212> TYPE: PRT
<213> ORGANISM: Aspergillus nidulans

<400> SEQUENCE: 30

Met Pro Ser Ser Gln Pro Ala Ser Ser His Ile Thr Thr Ala Pro Pro
1               5                   10                  15

Lys Ala Val Lys Pro Leu Ala Ser Lys Ser Lys Pro Leu Glu Pro Lys
                20                  25                  30

Ala Pro Glu Ser Lys Pro Ser Asp Ser Asn Val Pro Glu Pro Val Glu
            35                  40                  45
```

```
Pro Glu Ala Lys Ala Pro Glu Thr Lys Ser Phe Lys Glu Ala Leu Val
 50                  55                  60

Asn Gly Ala Gly Asp Gly Asp Lys Gln Thr Asp Ser Ser Asn Ser Thr
 65                  70                  75                  80

Ser Pro Ser Ser Phe Gln Ser Asp Ser Ile Arg Asp Ser Ser Pro Asn
                 85                  90                  95

Thr Ser Arg Ser Asn Ser Ser Ser Ser Gln Pro Thr Lys Glu Glu
            100                 105                 110

Thr Asp Lys Asp Thr Glu Lys Asn Ile Lys Glu Arg Asn Lys Gln Glu
            115                 120                 125

Gln Glu Lys Asp Thr Thr Thr Ile Pro Ile Val Ser Lys His Cys Ala
130                 135                 140

Val Thr Ser Lys Arg Leu Pro Ala Thr Asn Val Ser Ile Glu Lys Ser
145                 150                 155                 160

Gly Val Ala Arg Cys Asn Val Val Asp Gly Ala Thr Ser Asp Thr Ser
                165                 170                 175

Ile Lys Asp Phe His Glu Tyr Thr Pro Met Gln Gln His Ile Leu Phe
            180                 185                 190

Trp Asp Arg Asp Arg Asp Gly Gln Ile Tyr Pro Tyr Asp Thr Tyr Arg
            195                 200                 205

Gly Phe Arg Asp Leu Gly Phe Asn Ile Leu Phe Ser Phe Leu Ala Val
            210                 215                 220

Leu Ile Ile Asn Leu Asn Phe Ser Tyr Pro Thr Arg Leu Ala His Ser
225                 230                 235                 240

Phe Leu Pro Asp Pro Arg Phe Arg Val Tyr Val Asp Ser Ile Tyr Lys
                245                 250                 255

Ala Lys His Gly Ser Asp Ser Gly Ser Phe Asp Ala Glu Gly Arg Phe
            260                 265                 270

Ile Pro Gln His Phe Glu Asp Met Phe Ala Lys Tyr Asp Gly Asp Gln
            275                 280                 285

Asp Gly Ala Leu Thr Phe Gly Glu Leu Phe Asn Met Met His Gly Asn
            290                 295                 300

Arg Cys Ala Ala Asp Pro Phe Gly Trp Gly Ala Ala Phe Phe Glu Trp
305                 310                 315                 320

Val Thr Thr Trp Leu Leu Ile Gln Lys Asp Gly Lys Val Tyr Lys Asp
                325                 330                 335

Asp Leu Leu Gly Val Tyr Asp Gly Ser Leu Phe Trp Lys Ile Ala Lys
            340                 345                 350

Ala Arg Lys Ser Pro Gln Gly Trp Ser Gln Gly Phe Gly Leu Gly Gly
            355                 360                 365

Asp Gly Phe Leu Gly Gly Val Lys Val Ile
    370                 375

<210> SEQ ID NO 31
<211> LENGTH: 744
<212> TYPE: DNA
<213> ORGANISM: Magnaporthe grisea

<400> SEQUENCE: 31
atgggcgatt ctgacactgc caacggcact gtacgtacgt cagttccggg ggttcctgtc      60
acgatcgagc ggaagccctt cgtccaggac gagcatgagg accagaggct gcccaacgct     120
ggcacggccc gtgtcaacac tgccgcctcg tatgagcatc aaacggaac gaccgaggac      180 ggctatgcca ggcgacacag ccaccagacg gtgctgcagc agcactgtga cttttccgac    240
```

```
cgggaccaag acggtgtgat ttggccgcaa gacacctttg tcggcttcta ccgtcttggc    300
tttggtgtaa ttctgtcgct gatttccgtc ttcatcatcc acggcaactt ttcctacccc    360
acgagtccat cctggattcc ggatgctttc ttcaggatcc acctcgaccg tatccacaag    420
gacaagcacg gctctgatac gggcacctat gacaccgagg gcggttcgt gccgcagaag    480 tttgaggaca tctttgccaa gtacgccccc ggacaggaca gcctcacctg gagagatgtt    540
atgcaggttt tgcacggcca gcggctgtac gcagacccca ttggctggtt tgccgcggta    600
tttgaatggc ttgcaacgta tattctacta tggccagaag atggacacat gaagaaggat    660
gatatcaggg gagtctacga cggcagcatc ttctatacca tcgctgcccg tcgggaggaa    720
cgggtcaggc agaagagcag ctag                                           744
```

<210> SEQ ID NO 32
<211> LENGTH: 250
<212> TYPE: PRT
<213> ORGANISM: Magnaporthe grisea

<400> SEQUENCE: 32

```
Ser Glu Ala Met Gly Asp Ser Asp Thr Ala Asn Gly Thr Val Arg Thr
1               5                   10                  15

Ser Val Pro Gly Val Pro Val Thr Ile Glu Arg Lys Pro Phe Val Gln
                20                  25                  30

Asp Glu His Glu Asp Gln Arg Leu Pro Asn Ala Gly Thr Ala Arg Val
            35                  40                  45

Asn Thr Ala Ala Ser Tyr Glu His Pro Asn Gly Thr Thr Glu Asp Gly
        50                  55                  60

Tyr Ala Arg Arg His Ser His Gln Thr Val Leu Gln Gln His Cys Asp
65                  70                  75                  80

Phe Phe Asp Arg Asp Gln Asp Gly Val Ile Trp Pro Gln Asp Thr Phe
                85                  90                  95

Val Gly Phe Tyr Arg Leu Gly Phe Gly Val Ile Leu Ser Leu Ile Ser
            100                 105                 110

Val Phe Ile Ile His Gly Asn Phe Ser Tyr Pro Thr Ser Pro Ser Trp
        115                 120                 125

Ile Pro Asp Ala Phe Phe Arg Ile His Leu Asp Arg Ile His Lys Asp
130                 135                 140

Lys His Gly Ser Asp Thr Gly Thr Tyr Asp Thr Glu Gly Arg Phe Val
145                 150                 155                 160

Pro Gln Lys Phe Glu Asp Ile Phe Ala Lys Tyr Ala Pro Gly Gln Asp
                165                 170                 175

Ser Leu Thr Trp Arg Asp Val Met Gln Val Leu His Gly Gln Arg Leu
            180                 185                 190

Tyr Ala Asp Pro Ile Gly Trp Phe Ala Ala Val Phe Glu Trp Leu Ala
        195                 200                 205

Thr Tyr Ile Leu Leu Trp Pro Glu Asp Gly His Met Lys Lys Asp Asp
    210                 215                 220

Ile Arg Gly Val Tyr Asp Gly Ser Ile Phe Tyr Thr Ile Ala Ala Arg
225                 230                 235                 240

Arg Glu Glu Arg Val Arg Gln Lys Ser Ser
                245                 250
```

<210> SEQ ID NO 33
<211> LENGTH: 738
<212> TYPE: DNA
<213> ORGANISM: Artificial Sequence

```
<220> FEATURE:
<223> OTHER INFORMATION: Codon-optimized AtClo1 (AtClo1s)

<400> SEQUENCE: 33
atgggctcca agaccgagat gatggagcga gacgctatgg ccaccgtcgc tccttacgca      60
cccgttacct accaccgaag agcccgagtc gacctggacg atcgacttcc caaaccttac     120
atgcctcgag ccctgcaggc tcctgaccga gagcatccct acggaactcc tggtcacaag     180
aactacggcc tctccgtgct gcagcagcat gtctctttct tgacattga tgacaacgga     240
atcatttacc cctgggagac ctactccggt ctgcggatgc tcggcttcaa catcattgga     300
tctctgatca ttgccgctgt catcaacctt acactcagct acgccaccct gcctggttgg     360
cttccctctc ccttctttcc catctacatt cacaacattc ataagtccaa gcacggctcc     420
gacagcaaga cttacgacaa tgaaggacga ttcatgcccg tcaacctcga gctgatcttc     480
tcgaagtacg ccaagaccct gcccgacaag ctctccttgg gagagctgtg ggagatgacc     540
gaaggcaacc gagatgcttg ggacatcttt ggatggattg ccggcaagat cgagtggggt     600
ctgctctacc tgctcgctcg agacgaggaa ggcttcttgt ccaaggaggc cattcgaaga     660
tgctttgacg ttctctgtt cgagtactgt gccaagatct atgctggtat cagcgaggat     720
aagaccgcat actattaa                                                    738

<210> SEQ ID NO 34
<211> LENGTH: 702
<212> TYPE: DNA
<213> ORGANISM: Artificial sequence
<220> FEATURE:
<223> OTHER INFORMATION: Codon-optimized Ricinus communis caleosin
      (Cal01s)

<400> SEQUENCE: 34
atgggctccg agatcgacga ttccctggcc caggctgcac cctacgctcc tgtcaccttc      60
gagcgacccg tccgagacga tctcgaaact accctgccca gccttacat ggctagagcc     120
ctcgtggctc ccgacaccga gcatcccacc ggaactcctg ccacaagaa ccacggactg     180
tccgttcttc agcagcacgt cgccttttc gaccaggatg caacggcat tgtctatccc     240
tgggagacct acatcggtct gcgagctatt ggcttcaaca tcattgcatc tctggtcatg     300
gccatcgtca tcaatgtttc gctctcctat cctacacttc caggctggtt tccctctcct     360
ctgtttccca tctacattgg caacatccac aaggccaagc acggttctga ctccggaact     420
tacgataccg agggtcgaca catgcccgtc aacctcgaga catcttttc caagtactcg     480
aataccgtgc ccgacaagct tactttcggc gaactctggg acatgaccga gggtcaacgt     540
ctggccttcg acatctttgg atggattgct gccaaactcg agtggggact gctctacatt     600
ctggctcgag acgaggaagg tttcttgtct aaggaggccg tcagacgatg cttcgatggt     660
tccctgttcg agtactgtgc caagatgaac atgggacgat aa                        702

<210> SEQ ID NO 35
<211> LENGTH: 720
<212> TYPE: DNA
<213> ORGANISM: Artificial sequence
<220> FEATURE:
<223> OTHER INFORMATION: Codon-optimized Glycine max caleosin (Cal02s)

<400> SEQUENCE: 35
atggctgccg agatggaacg agaatccctg atcaccgagg ctcccaacgc tcctgtcact      60
gcccagcgaa gagtgcgaaa cgacctcgag aactctcttc caagccttta cctgccacga     120
```

```
gccctcaagg ctcccgacac cggacacccc aacggcaccg ctggtcaccg acatcacaat      180
ctgtccgtcc tccagcaaca ctgtgccttt ttcgatcagg acgataacgg catcatttac      240
ccctgggaaa cctacatggg actgagatcc attggcttca acgtcgtggc ctcggtcatc      300
atggccattg tcatcaacgt ggactctcc taccctactc ttcccaactg gtttccttct       360
ctgctcttcc ccatctacat tcacaacatt cacaaggcca acatggttc cgactctgga       420 gtctacgata ccgaaggtcg atacgttcct gctaacattg agaacatctt ctccaagtat      480
gcacgaaccg ttcccgacaa gctcactctg ggtgagctct gggatcttac cgagggcaat      540
cgaaacgcct tcgacatctt cggttggctg cagccaagt tcgagtgggg agtgctctac       600
attcttgctc gagacgagga aggctttctg tccaaggagg ccgtgcgacg ttgcttcgac      660
ggttcgctct tcgagtactg tgccaagatg cataccacat ctgatgccaa gatgtcctaa     720
```

<210> SEQ ID NO 36
<211> LENGTH: 738
<212> TYPE: DNA
<213> ORGANISM: Artificial sequence
<220> FEATURE:
<223> OTHER INFORMATION: Codon-optimized Sesamum indicum caleosin
      (Cal03s)

<400> SEQUENCE: 36

```
atggccaccc acgtcctggc tgccgctgcc gagcgaaacg ctgccctcgc tcccgacgct      60
cctctggctc ccgtcactat ggagcgacct gtgcgaaccg atctcgaaac ctccattccc     120
aagccttaca tggctcgagg cctggttgct cccgacatgg atcatcccaa cggtactcct     180
ggacacgtgc acgacaacct ttccgttctg cagcaacact gcgccttctt tgaccaggat     240
gacaacggta tcatttaccc ctgggagacc tactctggac tcagacagat cggcttcaac     300
gtcattgctt cgcttatcat ggccattgtc atcaacgttg cactgtctta tcccacattg     360
cctggctgga ttccctctcc attctttcct atctacctgt acaacattca aaggccaag     420 catggttccg actctggaac ctacgacacc gagggtcgat acctcccat gaacttcgag      480 aatctgttta gcaaacacgc tcgaaccatg cccgatagac tgactctcgg tgaactgtgg     540
tctatgaccg aggccaaccg agaggcattc gacatcttcg gctggattgc ctccaagatg     600
gagtggaccc ttctctacat cctggctcga gatcaggacg gatttctgtc caaggaagcc     660
attcgacgtt gttacgacgg ctccctcttc gagtactgcg ccaagatgca gcgaggtgcc     720
gaggacaaga tgaagtaa                                                   738
```

<210> SEQ ID NO 37
<211> LENGTH: 954
<212> TYPE: DNA
<213> ORGANISM: Artificial sequence
<220> FEATURE:
<223> OTHER INFORMATION: Codon-optimized Coix lacryma caleosin (Cal04s)

<400> SEQUENCE: 37

```
atggagggtg ccactaccgc tgccggcaac aagcaacagg cacgatctgg tgaccgagga      60
gccgctaaga ccgccaccga tggcaagaag ggcgacgcag acgtggccaa gggagaccct     120
gctgccggtg ccaagcaggc tgccggcgac gctggcaagg gtggagccgc tgccactggt     180
aacaataagc aggctgccgg cggagccatg caccatcacg ttttttcctc tgctgttgag     240
gccaaagatt cccagaccat tgttgctctc caggctcccg tcactgtgac ccgacccgtc     300
agaggcgacc ttgaggaaca cgtgcccaag ccctaccttg ctcgagccct cgctgcccct     360
```

```
gacatttatc accccgaagg aaccoctgag gatgagcacc gacaccatca catgtctgtg    420
ctccaacagc acgtcgcctt ctttgacaga gatgacaacg gtatcattta cccctgggag    480
acttactcgg gttgccgagc tctcggcttc aacatggtcc tctcctttct gatcgccgtc    540
gttgtgaacg gtacaatgtc ttacgctacc ctgcctggat ggcttccctc ccctctcttt    600
cccatctatg tccataacat ccataagtct aaacacggtt ccgacttcgg cacctacgac    660
aacgagggtc ggttcatgcc agtgaacttc gagaacatgt tctctaagta cgcacgaact    720
tcgcctgaca gactcaccta tcgagaactg tggtccatga ccgagggatt ccgagatgcc    780
ctggacctct acggttgggt tgcagccaag ctggagtgga ccatcttata cgttcttgca    840
cgagacgatg agggctacct ggctcgagag gccatgcgaa gactgtacga tggatctctc    900
ttcgagtacg tcgaacgaca gcggatgcag cacgcccatg ccaagatgtc ctaa          954

<210> SEQ ID NO 38
<211> LENGTH: 317
<212> TYPE: PRT
<213> ORGANISM: Artificial sequence
<220> FEATURE:
<223> OTHER INFORMATION: Codon-optimized Coix lacryma caleosin (Cal04s)
      polypeptide

<400> SEQUENCE: 38

Met Glu Gly Ala Thr Thr Ala Ala Gly Asn Lys Gln Gln Ala Arg Ser
1               5                   10                  15

Gly Asp Arg Gly Ala Ala Lys Thr Ala Thr Asp Gly Lys Lys Gly Asp
                20                  25                  30

Ala Asp Val Ala Lys Gly Asp Pro Ala Ala Gly Ala Lys Gln Ala Ala
            35                  40                  45

Gly Asp Ala Gly Lys Gly Gly Ala Ala Ala Thr Gly Asn Asn Lys Gln
        50                  55                  60

Ala Ala Gly Gly Ala Met His His Gly Phe Ser Ser Ala Val Glu
65                  70                  75                  80

Ala Lys Asp Ser Gln Thr Ile Val Ala Leu Gln Ala Pro Val Thr Val
                85                  90                  95

Thr Arg Pro Val Arg Gly Asp Leu Glu His Val Pro Lys Pro Tyr
                100                 105                 110

Leu Ala Arg Ala Leu Ala Ala Pro Asp Ile Tyr His Pro Glu Gly Thr
            115                 120                 125

Pro Glu Asp Glu His Arg His His His Met Ser Val Leu Gln Gln His
        130                 135                 140

Val Ala Phe Phe Asp Arg Asp Asp Asn Gly Ile Ile Tyr Pro Trp Glu
145                 150                 155                 160

Thr Tyr Ser Gly Cys Arg Ala Leu Gly Phe Asn Met Val Leu Ser Phe
                165                 170                 175

Leu Ile Ala Val Val Asn Gly Thr Met Ser Tyr Ala Thr Leu Pro
            180                 185                 190

Gly Trp Leu Pro Ser Pro Leu Phe Pro Ile Tyr Val His Asn Ile His
        195                 200                 205

Lys Ser Lys His Gly Ser Asp Phe Gly Thr Tyr Asp Asn Glu Gly Arg
    210                 215                 220

Phe Met Pro Val Asn Phe Glu Asn Met Phe Ser Lys Tyr Ala Arg Thr
225                 230                 235                 240

Ser Pro Asp Arg Leu Thr Tyr Arg Glu Leu Trp Ser Met Thr Glu Gly
                245                 250                 255
```

```
Phe Arg Asp Ala Leu Asp Leu Tyr Gly Trp Val Ala Ala Lys Leu Glu
            260                 265                 270

Trp Thr Ile Leu Tyr Val Leu Ala Arg Asp Asp Glu Gly Tyr Leu Ala
        275                 280                 285

Arg Glu Ala Met Arg Leu Tyr Asp Gly Ser Leu Phe Glu Tyr Val
290                 295                 300

Glu Arg Gln Arg Met Gln His Ala His Ala Lys Met Ser
305                 310                 315

<210> SEQ ID NO 39
<211> LENGTH: 849
<212> TYPE: DNA
<213> ORGANISM: Artificial sequence
<220> FEATURE:
<223> OTHER INFORMATION: Codon-optimized Aspergillus niger caleosin
      (Cal05s)

<400> SEQUENCE: 39
atggctcgaa aggtctcgtt ttccgagacc cagcttccca acttcgacaa gcccatccga      60
cctccctcca tttctgtgga tttctccacc actgctcccg agtgtcctgt caccgctgcc     120
cgagagcctg ctcgatacac caacgactat atcgagaagc tggtgttcc cagagccaac     180 accacagcct ctattgaccg acccgatggc gacgaatcct acaccaagca gttttcggac     240
ttcactcccc tccagcaaca cgtgctgttt tgggacagag atcgagacgg acagatctat     300
ccctgggaca cttacattgg cttcagagag cttggtttca acatgctgtt tcgttcctc      360 gccgttctga ttatcaatct caacttttcc taccccactc gactcgcaca ctcttttcctg    420 cccgacccctt ggtttcgagt gtacgtcgac gctgttcaca aggccaaaca cggatccgac    480
tcgaacacct acgaccccga gggacgattc gtccctcagt cttttgagaa catgttcgca    540
aagtacgaca gagatggtga cggagccctc accctgcgag agctgttcga tatgatgcat    600
ggcaaccgat cgctgccga tcccttggc tggggtgccg ctatctgcga gtggggcacc      660
acatggcttc tgatcgagaa agacggaaag gtgtggaagg aggacgttcg aggtgtctac    720
gatggttctc tcttctggaa ggtgcgagaa gccaactact ctggacgagg ctggtcccag    780
ggtttccgac ctggtctctg gatcaagcga accgtcaagg gcgtgctgaa cgcctacctg    840
gacggataa                                                             849

<210> SEQ ID NO 40
<211> LENGTH: 282
<212> TYPE: PRT
<213> ORGANISM: Artificial sequence
<220> FEATURE:
<223> OTHER INFORMATION: Codon-optimized Aspergillus niger caleosin
      (Cal05s) polypeptide

<400> SEQUENCE: 40

Met Ala Arg Lys Val Ser Phe Ser Glu Thr Gln Leu Pro Asn Phe Asp
1               5                   10                  15

Lys Pro Ile Arg Pro Pro Ser Ile Ser Val Asp Phe Ser Thr Thr Ala
            20                  25                  30

Pro Glu Cys Pro Val Thr Ala Ala Arg Glu Pro Ala Arg Tyr Thr Asn
        35                  40                  45

Asp Tyr Ile Glu Lys Pro Gly Val Pro Arg Ala Asn Thr Thr Ala Ser
    50                  55                  60

Ile Asp Arg Pro Asp Gly Asp Glu Ser Tyr Thr Lys Gln Phe Ser Asp
65                  70                  75                  80
```

```
Phe Thr Pro Leu Gln Gln His Val Leu Phe Trp Asp Arg Asp Arg Asp
                85                  90                  95
Gly Gln Ile Tyr Pro Trp Asp Thr Tyr Ile Gly Phe Arg Glu Leu Gly
            100                 105                 110
Phe Asn Met Leu Phe Ser Phe Leu Ala Val Leu Ile Ile Asn Leu Asn
        115                 120                 125
Phe Ser Tyr Pro Thr Arg Leu Ala His Ser Phe Leu Pro Asp Pro Trp
    130                 135                 140
Phe Arg Val Tyr Val Asp Ala Val His Lys Ala Lys His Gly Ser Asp
145                 150                 155                 160
Ser Asn Thr Tyr Asp Pro Glu Gly Arg Phe Val Pro Gln Ser Phe Glu
                165                 170                 175
Asn Met Phe Ala Lys Tyr Asp Arg Asp Gly Asp Gly Ala Leu Thr Leu
            180                 185                 190
Arg Glu Leu Phe Asp Met Met His Gly Asn Arg Cys Ala Ala Asp Pro
        195                 200                 205
Phe Gly Trp Gly Ala Ala Ile Cys Glu Trp Gly Thr Thr Trp Leu Leu
    210                 215                 220
Ile Glu Lys Asp Gly Lys Val Trp Lys Glu Asp Val Arg Gly Val Tyr
225                 230                 235                 240
Asp Gly Ser Leu Phe Trp Lys Val Arg Glu Ala Asn Tyr Ser Gly Arg
                245                 250                 255
Gly Trp Ser Gln Gly Phe Arg Pro Gly Leu Trp Ile Lys Arg Thr Val
            260                 265                 270
Lys Gly Val Leu Asn Ala Tyr Leu Asp Gly
        275                 280

<210> SEQ ID NO 41
<211> LENGTH: 900
<212> TYPE: DNA
<213> ORGANISM: Artificial sequence
<220> FEATURE:
<223> OTHER INFORMATION: Codon-optimized Neurospora crassa caleosin
      (Cal06s)

<400> SEQUENCE: 41
atggccgtcc gagtcgttcc tcgagaggac gagcaggtgg acgacgaacg acagggcgtt      60
gattttgcca ccgctgtgtc caactgtcct cccactgccg agcgaccaca ggccatcgac     120
attgatgtgg acatctataa gccctctatt gccagagcca acgttgctcc ctcgaccgaa     180
cagcccgaag gctccgctga gtacgtggac gccctcgatc tgaaggacta caccgttctt     240
cagcaacact gtatgttctg ggacagagat cgagatggag tcatctggcc tcaggacact     300
ttcattggct tttacgagtt aggtttcaac ctcttttttct gctttctggc cactctcgtc     360
atcaatctga acttctctta ccccactcga ctgggcgtgt cctacattcc cgacccatac     420
tttcgactct acctgccctc tatgcacaag gccaagcatg gctccgactc aggtaccctat     480 gacaaggaag acgattcgt tccccaggct ttcgaggaca tgttctcgaa gtgggatcga     540
ggagacaagg gtgctctttc cgctggcgag ctgtggaaca tgattgctgc caaccgactc     600
gcagccgacc ctttcggttg gctgccggaa atcttcgagt ttggtgtcac ctggctgctc     660
gtgcaacagg acggcatggt cgacaaggag gaccttcgac ggatctacga tggttctatg     720
ttctttaaga tcagagaggc ataccgaaca gagaagggat ggaacaaggg tttcggtctc     780
tgcgagttct ttaacttagg tcgagagcag tgggccaaga acaaggacg aatccctccc     840
```
ctgaacggca ttgtctccaa ggtggagcga tctgtcaccc agaagcttca ccgagcttaa    900

<210> SEQ ID NO 42
<211> LENGTH: 299
<212> TYPE: PRT
<213> ORGANISM: Artificial sequence
<220> FEATURE:
<223> OTHER INFORMATION: Codon-optimized Neurospora crassa caleosin
      (Cal06s) polypeptide

<400> SEQUENCE: 42

Met Ala Val Arg Val Pro Arg Glu Asp Glu Gln Val Asp Asp Glu
1               5                   10                  15

Arg Gln Gly Val Asp Phe Ala Thr Ala Val Ser Asn Cys Pro Pro Thr
            20                  25                  30

Ala Glu Arg Pro Gln Ala Ile Asp Ile Asp Val Asp Ile Tyr Lys Pro
        35                  40                  45

Ser Ile Ala Arg Ala Asn Val Ala Pro Ser Thr Glu Gln Pro Glu Gly
    50                  55                  60

Ser Ala Glu Tyr Val Asp Ala Leu Asp Leu Lys Asp Tyr Thr Val Leu
65                  70                  75                  80

Gln Gln His Cys Met Phe Trp Asp Arg Asp Arg Asp Gly Val Ile Trp
                85                  90                  95

Pro Gln Asp Thr Phe Ile Gly Phe Tyr Glu Leu Gly Phe Asn Leu Phe
            100                 105                 110

Phe Cys Phe Leu Ala Thr Leu Val Ile Asn Leu Asn Phe Ser Tyr Pro
        115                 120                 125

Thr Arg Leu Gly Val Ser Tyr Ile Pro Asp Pro Tyr Phe Arg Leu Tyr
    130                 135                 140

Leu Pro Ser Met His Lys Ala Lys His Gly Ser Asp Ser Gly Thr Tyr
145                 150                 155                 160

Asp Lys Glu Gly Arg Phe Val Pro Gln Ala Phe Glu Asp Met Phe Ser
                165                 170                 175

Lys Trp Asp Arg Gly Asp Lys Gly Ala Leu Ser Ala Gly Glu Leu Trp
            180                 185                 190

Asn Met Ile Ala Ala Asn Arg Leu Ala Ala Asp Pro Phe Gly Trp Ala
        195                 200                 205

Ala Gly Ile Phe Glu Phe Gly Val Thr Trp Leu Leu Val Gln Gln Asp
    210                 215                 220

Gly Met Val Asp Lys Glu Asp Leu Arg Arg Ile Tyr Asp Gly Ser Met
225                 230                 235                 240

Phe Phe Lys Ile Arg Glu Ala Tyr Arg Thr Glu Lys Gly Trp Asn Lys
                245                 250                 255

Gly Phe Gly Leu Cys Glu Phe Phe Asn Leu Gly Arg Gly Gln Trp Ala
            260                 265                 270

Lys Asn Lys Gly Arg Ile Pro Pro Leu Asn Gly Ile Val Ser Lys Val
        275                 280                 285

Glu Arg Ser Val Thr Gln Lys Leu His Arg Ala
    290                 295

<210> SEQ ID NO 43
<211> LENGTH: 7882
<212> TYPE: DNA
<213> ORGANISM: Artificial sequence
<220> FEATURE:
<223> OTHER INFORMATION: Plasmid pYRH55

<400> SEQUENCE: 43

-continued

```
ggccgcaagt gtggatgggg aagtgagtgc ccggttctgt gtgcacaatt ggcaatccaa        60
gatggatgga ttcaacacag ggatatagcg agctacgtgg tggtgcgagg atatagcaac       120
ggatatttat gtttgacact tgagaatgta cgatacaagc actgtccaag tacaatacta       180
aacatactgt acatactcat actcgtaccc gggcaacgtt ttcacttgag tgcagtggct       240
agtgctctta ctcgtacagt gtgcaatact gcgtatcata gtctttgatg tatatcgtat       300
tcattcatgt tagttgcgta cgttgattga ggtggagcca gatgggctat tgtttcatat       360
atagactggc agccacctct ttggcccagc atgtttgtat acctggaagg gaaaactaaa       420
gaagctggct agtttagttt gattattata gtagatgtcc taatcactag agattagaat       480
gtcttggcga tgattagtcg tcgtccoctg tatcatgtct agaccaactg tgtcatgaag       540
ttggtgctgg tgttttacct gtgtactaca agtaggtgtc ctagatctag tgtacagagc       600
cgtttagacc catgtggact tcaccattaa cgatggaaaa tgttcattat atgacagtat       660
attacaatgg acttgctcca tttcttcctt gcatcacatg ttctccacct ccatagttga       720
tcaacacatc atagtagcta aggctgctgc tctcccacta cagtccacca caagttaagt       780
agcaccgtca gtacagctaa aagtacacgt ctagtacgtt tcataactag tcaagtagcc       840
cctattacag atatcagcac tatcacgcac gagttttttct ctgtgctatc taatcaactt       900
gccaagtatt cggagaagat acactttctt ggcatcaggt atacgaggga gcctatcaga       960
tgaaaaaggg tatattggat ccattcatat ccacctacac gttgtcataa tctcctcatt      1020
cacgtgattc atttcgtgac actagttttct cactttcccc cccgcaccta tagtcaactt      1080
ggcggacacg ctacttgtag ctgacgttga tttatagacc caatcaaagc gggttatcgg      1140
tcaggtagca cttatcattc atcgttcata ctacgatgag caatctcggg catgtccgga      1200
aaagtgtcgg gcgcgccagc tgcattaatg aatcggccaa cgcgcgggga gaggcggttt      1260
gcgtattggg cgctcttccg cttcctcgct cactgactcg ctgcgctcgg tcgttcggct      1320
gcggcgagcg gtatcagctc actcaaaggc ggtaatacgg ttatccacag aatcagggga      1380
taacgcagga agaacatgt gagcaaaagg ccagcaaaag gccaggaacc gtaaaaaggc       1440
cgcgttgctg gcgttttttcc ataggctccg ccccccctgac gagcatcaca aaaatcgacg      1500
ctcaagtcag aggtggcgaa acccgacagg actataaaga taccaggcgt ttccccctgg      1560
aagctccctc gtgcgctctc ctgttccgac cctgccgctt accggatacc tgtccgcctt      1620
tctcccttcg ggaagcgtgg cgctttctca tagctcacgc tgtaggtatc tcagttcggt      1680
gtaggtcgtt cgctccaagc tgggctgtgt gcacgaaccc cccgttcagc ccgaccgctg      1740
cgccttatcc ggtaactatc gtcttgagtc caacccggta agacacgact tatcgccact      1800
ggcagcagcc actggtaaca ggattagcag agcgaggtat gtaggcggtg ctacagagtt      1860
cttgaagtgg tggcctaact acggctacac tagaagaaca gtatttggta tctgcgctct      1920
gctgaagcca gttaccttcg gaaaaagagt tggtagctct tgatccggca aacaaaccac      1980
cgctggtagc ggtggttttt ttgtttgcaa gcagcagatt acgcgcagaa aaaaggatc      2040
tcaagaagat cctttgatct tttctacggg gtctgacgct cagtggaacg aaaactcacg      2100
ttaagggatt ttggtcatga gattatcaaa aaggatcttc acctagatcc ttttaaatta      2160
aaaatgaagt tttaaatcaa tctaaagtat atatgagtaa acttggtctg acagttacca      2220
atgcttaatc agtgaggcac ctatctcagc gatctgtcta tttcgttcat ccatagttgc      2280
ctgactcccc gtcgtgtaga taactacgat acgggagggc ttaccatctg gccccagtgc      2340
```

```
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcgggc gaaaactctc aaggatctta ccgctgttga tccagttc     2940 gatgtaaccc actcgtgcac ccaactgatc ttcagcatct tttactttca ccagcgtttc    3000
tgggtgagca aaaacaggaa ggcaaaatgc cgcaaaaaag gaataagggc gacacggaa    3060 atgttgaata ctcatactct ccttttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagttttttt ggggtcgagg tgccgtaaag cactaaatcg    3540
gaaccctaaa gggagccccc gatttagagc ttgacgggga agccggcga acgtggcgag    3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aaggggggatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaacccta ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaagaatt gatttgtgcg agcaggttaa    4680
ttaagtcata cacaagtcag ctttcttcga gcctcatata agtataagta gttcaacgta    4740
```

```
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggggagca   5580 cagtgccggc gtaggtgaag tcgtcaatga tgtcgatatg ggttttgatc atgcacacat    5640
aaggtccgac cttatcggca agctcaatga gctccttggt ggtggtaaca tccagagaag    5700
cacacaggtt ggttttcttg gctgccacga gcttgagcac tcgagcggca aaggcggact    5760
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300 gggggggcctt tttatatggc caagccaagc tctccacgtc ggttgggctg cacccaacaa    6360
taaatgggta gggttgcacc aacaagggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctgga    6780 tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcggggggct tgtctagggt atatataaac agtggctctc ccaatcggtt    6960
gccagtctct ttttcctttt ctttccccac agattcgaaa tctaaactac acatcacaga    7020
attccgagcc gtgagtatcc acgacaagat cagtgtcgag acgacgcgtt ttgtgtaatg    7080
```

```
acacaatccg aaagtcgcta gcaacacaca ctctctacac aaactaaccc agctctggta    7140
ccatgggctc caagaccgag atgatggagc gagacgctat ggccaccgtc gctccttacg    7200
cacccgttac ctaccaccga agagcccgag tcgacctgga cgatcgactt cccaaacctt    7260
acatgcctcg agccctgcag gctcctgacc gagagcatcc ctacggaact cctggtcaca    7320
agaactacgg cctctccgtg ctgcagcagc atgtctcttt ctttgacatt gatgacaacg    7380
gaatcattta cccctgggag acctactccg gtctgcggat gctcggcttc aacatcattg    7440
gatctctgat cattgccgct gtcatcaacc ttacactcag ctacgccacc ctgcctggtt    7500
ggcttccctc tcccttcttt cccatctaca ttcacaacat tcataagtcc aagcacggct    7560
ccgacagcaa gacttacgac aatgaaggac gattcatgcc cgtcaacctc gagctgatct    7620
tctcgaagta cgccaagacc ctgcccgaca agctctcctt gggagagctg tgggagatga    7680
ccgaaggcaa ccgagatgct tgggacatct ttggatggat tgccggcaag atcgagtggg    7740
gtctgctcta cctgctcgct cgagacgagg aaggcttctt gtccaaggag gccattcgaa    7800
gatgctttga cggttctctg ttcgagtact gtgccaagat ctatgctggt atcagcgagg    7860
ataagaccgc atactattaa gc                                              7882

<210> SEQ ID NO 44
<211> LENGTH: 7846
<212> TYPE: DNA
<213> ORGANISM: Artificial sequence
<220> FEATURE:
<223> OTHER INFORMATION: Construct pYRH84

<400> SEQUENCE: 44
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag     540
ttggtgctgg tgttttacct gtgtactaca agtaggtgtc ctagatctag tgtacagagc     600
cgtttagacc catgtggact tcaccattaa cgatggaaaa tgttcattat atgacagtat     660
attacaatgg acttgctcca tttcttcctt gcatcacatg ttctccacct ccatagttga     720
tcaacacatc atagtagcta aggctgctgc tctcccacta cagtccacca caagttaagt     780
agcaccgtca gtacagctaa aagtacacgt ctagtacgtt tcataactag tcaagtagcc     840
cctattacag atatcagcac tatcacgcac gagttttttct ctgtgctatc taatcaactt     900
gccaagtatt cggagaagat acactttctt ggcatcaggt atacgaggga gcctatcaga     960
tgaaaaaggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
```

```
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga agaacatgt gagcaaaagg ccagcaaaag gccaggaacc gtaaaaaggc    1440
cgcgttgctg gcgttttcc ataggctccg ccccctgac gagcatcaca aaatcgacg    1500 ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc caacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca acaaaccac    1980 cgctggtagc ggtggttttt ttgtttgcaa gcagcagatt acgcgcagaa aaaaggatc    2040 tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atccccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcggggc gaaaactctc aaggatctta ccgctgttga tccagttc    2940 gatgtaaccc actcgtgcac ccaactgatc ttcagcatct tttactttca ccagcgtttc    3000
tgggtgagca aaaacaggaa ggcaaaatgc cgcaaaaaag gaataagggc gacacggaa    3060 atgttgaata ctcatactct tccttttca atattattga gcatttatc agggttattg    3120 tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagttttt ggggtcgagg tgccgtaaag cactaaatcg    3540
gaaccctaaa gggagccccc gatttagagc ttgacgggga agccggcgaa acgtggcgag    3600
```

```
aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aaggggggatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaaccctc tttcatcaa gtgcaagaac     4020 ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaagatt gatttgtgcg agcaggttaa     4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctcccct gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580 cagtgccggc gtaggtgaag tcgtcaatga tgtcgatatg ggttttgatc atgcacacat    5640
aaggtccgac cttatcggca agctcaatga gctccttggt ggtggtaaca tccagagaag    5700
cacacaggtt ggttttcttg gctgccacga gcttgagcac tcgagcggca aggcggact     5760 tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
```

```
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300
ggggggcctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gccccctgga    6780
tatagccccg acataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggct tgtctagggt atatataaac agtggctctc ccaatcggtt    6960
gccagtctct ttttcctttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatgggctc cgagatcgac gattccctgg cccaggctgc accctacgct cctgtcacct    7200
tcgagcgacc cgtccgagac gatctcgaaa ctaccctgcc caagccttac atggctagag    7260
ccctcgtggc tcccgacacc gagcatccca ccggaactcc tggccacaag aaccacggac    7320
tgtccgttct tcagcagcac gtcgcctttt tcgaccagga tgacaacggc attgtctatc    7380
cctgggagac ctacatcggt ctgcgagcta ttggcttcaa catcattgca tctctggtca    7440
tggccatcgt catcaatgtt tcgctctcct atcctacact tccaggctgg tttccctctc    7500
ctctgtttcc catctacatt ggcaacatcc acaaggccaa gcacggttct gactccggaa    7560
cttacgatac cgagggtcga cacatgcccg tcaacctcga gaacatcttt tccaagtact    7620
cgaataccgt gcccgacaag cttactttcg gcgaactctg ggacatgacc gagggtcaac    7680
gtctggcctt cgacatcttt ggatggattg ctgccaaact cgagtgggga ctgctctaca    7740
ttctggctcg agacgaggaa ggtttcttgt ctaaggaggc cgtcagacga tgcttcgatg    7800
gttccctgtt cgagtactgt gccaagatga acatgggacg ataagc    7846
```

<210> SEQ ID NO 45
<211> LENGTH: 7864
<212> TYPE: DNA
<213> ORGANISM: Artificial sequence
<220> FEATURE:
<223> OTHER INFORMATION: Construct pYRH85

<400> SEQUENCE: 45

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
```

```
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgttgattga ggtggagcca gatgggctat tgtttcatat    360
atagactggc agccacctct ttggcccagc atgtttgtat acctggaagg gaaaactaaa    420
gaagctggct agtttagttt gattattata gtagatgtcc taatcactag agattagaat    480
gtcttggcga tgattagtcg tcgtcccctg tatcatgtct agaccaactg tgtcatgaag    540
ttggtgctgg tgtttacct gtgtactaca agtaggtgtc ctagatctag tgtacagagc    600
cgtttagacc catgtggact tcaccattaa cgatggaaaa tgttcattat atgacagtat    660
attacaatgg acttgctcca tttcttcctt gcatcacatg ttctccacct ccatagttga    720
tcaacacatc atagtagcta aggctgctgc tctcccacta cagtccacca caagttaagt    780
agcaccgtca gtacagctaa aagtacacgt ctagtacgtt tcataactag tcaagtagcc    840
cctattacag atatcagcac tatcacgcac gagttttttct ctgtgctatc taatcaactt    900
gccaagtatt cggagaagat acactttctt ggcatcaggt atacgaggga gcctatcaga    960
tgaaaaaggg tatattggat ccattcatat ccacctacac gttgtcataa tctcctcatt   1020
cacgtgattc atttcgtgac actagtttct cactttcccc cccgcaccta tagtcaactt   1080
ggcggacacg ctacttgtag ctgacgttga tttatagacc caatcaaagc gggttatcgg   1140
tcaggtagca cttatcattc atcgttcata ctacgatgag caatctcggg catgtccgga   1200
aaagtgtcgg gcgcgccagc tgcattaatg aatcggccaa cgcgcgggga gaggcggttt   1260
gcgtattggg cgctcttccg cttcctcgct cactgactcg ctgcgctcgg tcgttcggct   1320
gcggcgagcg gtatcagctc actcaaaggc ggtaatacgg ttatccacag aatcagggga   1380
taacgcagga aagaacatgt gagcaaaagg ccagcaaaag gccaggaacc gtaaaaaggc   1440
cgcgttgctg gcgtttttcc ataggctccg ccccctgac gagcatcaca aaaatcgacg   1500
ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgcttttctca tagctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca acaaaccac   1980
cgctggtagc ggtggttttt tgtttgcaa gcagcagatt acgcgcagaa aaaaaggatc   2040
tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
```

```
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcgggGC gaaaactctc aaggatctta ccgctgttga gatccagttc    2940
gatgtaaccc actcgtgcac ccaactgatc ttcagcatct tttactttca ccagcgtttc    3000
tgggtgagca aaaacaggaa ggcaaaatgc cgcaaaaaag gaataagggg cgacacggaa    3060
atgttgaata ctcatactct ccttttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagtttttt gggGtcgagg tgccgtaaag cactaaatcg    3540
gaaccctaaa gggagccccc gatttagagc ttgacgggga agccggcga acgtggcgag    3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aggggGatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaaccccta ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagacccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
```

```
catatccata gtctaacctc taacagttaa tcttctggta agcctcccag ccagccttct   4980
ggtatcgctt ggcctcctca ataggatctc ggttctggcc gtacagacct cggccgacaa   5040
ttatgatatc cgttccggta gacatgacat cctcaacagt tcggtactgc tgtccgagag   5100
cgtctccctt gtcgtcaaga cccaccccgg gggtcagaat aagccagtcc tcagagtcgc   5160
ccttaggtcg gttctgggca atgaagccaa ccacaaactc ggggtcggat cgggcaagct   5220
caatggtctg cttggagtac tcgccagtgg ccagagagcc cttgcaagac agctcggcca   5280
gcatgagcag acctctggcc agcttctcgt tgggagaggg gactaggaac tccttgtact   5340
gggagttctc gtagtcagag acgtcctcct tcttctgttc agagacagtt tcctcggcac   5400
cagctcgcag gccagcaatg attccggttc cgggtacacc gtgggcgttg gtgatatcgg   5460
accactcggc gattcggtga caccggtact ggtgcttgac agtgttgcca atatctgcga   5520
actttctgtc ctcgaacagg aagaaaccgt gcttaagagc aagttccttg aggggagca   5580
cagtgccggc gtaggtgaag tcgtcaatga tgtcgatatg ggttttgatc atgcacacat   5640
aaggtccgac cttatcggca agctcaatga gctccttggt ggtggtaaca tccagagaag   5700
cacacaggtt ggttttcttg gctgccacga gcttgagcac tcgagcggca aaggcggact   5760
tgtggacgtt agctcgagct tcgtaggagg gcattttggt ggtgaagagg agactgaaat   5820
aaatttagtc tgcagaactt tttatcggaa ccttatctgg ggcagtgaag tatatgttat   5880
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
cagctgtcag acccacagcc tccaacgaag aatgtatcgt caaagtgatc caagcacact   6120
catagttgga gtcgtactcc aaaggcggca atgacgagtc agacagatac tcgtcgacgt   6180
ttaaacagtg tacgcagatc tactatagag gaacatttaa attgccccgg agaagacggc   6240
caggccgcct agatgacaaa ttcaacaact cacagctgac tttctgccat tgccactagg   6300
gggggggcctt tttatatggc caagccaagc tctccacgtc ggttgggctg cacccaacaa   6360
taaatgggta gggttgcacc aacaaaggga tgggatgggg ggtagaagat acgaggataa   6420
cggggctcaa tggcacaaat aagaacgaat actgccatta agactcgtga tccagcgact   6480
gacaccattg catcatctaa gggcctcaaa actacctcgg aactgctgcg ctgatctgga   6540
caccacagag gttccgagca ctttaggttg caccaaatgt cccaccaggt gcaggcagaa   6600
aacgctggaa cagcgtgtac agtttgtctt aacaaaaagt gagggcgctg aggtcgagca   6660
gggtggtgtg acttgttata gcctttagag ctgcgaaagc gcgtatggat ttggctcatc   6720
aggccagatt gagggtctgt ggacacatgt catgttagtg tacttcaatc gcccctgga   6780
tatagccccg acaataggcc gtggcctcat ttttttgcct tccgcacatt tccattgctc   6840
gatacccaca ccttgcttct cctgcacttg ccaaccttaa tactggttta cattgaccaa   6900
catcttacaa gcgggggct tgtctagggt atatataaac agtggctctc ccaatcggtt   6960
gccagtctct tttttccttt ctttcccac agattcgaaa tctaaactac acatcacaga   7020
attccgagcc gtgagtatcc acgacaagat cagtgtcgag acgacgcgtt ttgtgtaatg   7080
acacaatccg aaagtcgcta gcaacacaca ctctctacac aaactaaccc agctctggta   7140
ccatggctgc cgagatggaa cgagaatccc tgatcaccga ggctcccaac gctcctgtca   7200
ctgcccagcg aagagtgcga aacgacctcg agaactctct tcccaagcct tacctgccac   7260
gagccctcaa ggctcccgac accggacacc ccaacggcac cgctggtcac cgacatcaca   7320
```

-continued

```
atctgtccgt cctccagcaa cactgtgcct ttttcgatca ggacgataac ggcatcattt    7380
acccctggga aacctacatg ggactgagat ccattggctt caacgtcgtg gcctcggtca    7440
tcatggccat tgtcatcaac gttggactct cctaccctac tcttcccaac tggtttcctt    7500
ctctgctctt cccatctac attcacaaca ttcacaaggc caaacatggt tccgactctg     7560
gagtctacga taccgaaggt cgatacgttc ctgctaacat tgagaacatc ttctccaagt    7620
atgcacgaac cgttcccgac aagctcactc tgggtgagct ctgggatctt accgagggca    7680
atcgaaacgc cttcgacatc ttcggttggc tggcagccaa gttcgagtgg ggagtgctct    7740
acattcttgc tcgagacgag gaaggctttc tgtccaagga ggccgtgcga cgttgcttcg    7800
acggttcgct cttcgagtac tgtgccaaga tgcataccac atctgatgcc aagatgtcct    7860
aagc                                                                 7864
```

<210> SEQ ID NO 46
<211> LENGTH: 7882
<212> TYPE: DNA
<213> ORGANISM: Artificial sequence
<220> FEATURE:
<223> OTHER INFORMATION: Construct pYRH86

<400> SEQUENCE: 46

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag     540
ttggtgctgg tgttttacct gtgtactaca agtaggtgtc ctagatctag tgtacagagc     600
cgtttagacc catgtggact tcaccattaa cgatggaaaa tgttcattat atgacagtat     660
attacaatgg acttgctcca tttcttcctt gcatcacatg ttctccacct ccatagttga     720
tcaacacatc atagtagcta aggctgctgc tctcccacta cagtccacca caagttaagt     780
agcaccgtca gtacagctaa aagtacacgt ctagtacgtt tcataactag tcaagtagcc     840
cctattacag atatcagcac tatcacgcac gagtttttct ctgtgctatc taatcaactt     900
gccaagtatt cggagaagat acactttctt ggcatcaggt atacgaggga gcctatcaga     960
tgaaaaaggg tatattggat ccattcatat ccacctacac gttgtcataa tctcctcatt    1020
cacgtgattc atttcgtgac actagttcct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga aagaacatgt gagcaaaagg ccagcaaaag gccaggaacc gtaaaaaggc    1440
```

```
cgcgttgctg gcgtttttcc ataggctccg cccccctgac gagcatcaca aaaatcgacg   1500
ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgctttctca tagctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca aacaaaccac   1980
cgctggtagc ggtggttttt ttgtttgcaa gcagcagatt acgcgcagaa aaaaaggatc   2040
tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
cggttcccaa cgatcaaggc gagttacatg atccccccatg ttgtgcaaaa agcggttag   2640 ctccttcggt cctccgatcg ttgtcagaag taagttggcc gcagtgttat cactcatggt   2700
tatggcagca ctgcataatt ctcttactgt catgccatcc gtaagatgct tttctgtgac   2760
tggtgagtac tcaaccaagt cattctgaga atagtgtatg cggcgaccga gttgctcttg   2820
cccggcgtca atacgggata ataccgcgcc acatagcaga actttaaaag tgctcatcat   2880
tggaaaacgt tcttcggggc gaaaactctc aaggatctta ccgctgttga tccagttc   2940 gatgtaaccc actcgtgcac ccaactgatc ttcagcatct tttactttca ccagcgtttc   3000
tgggtgagca aaaacaggaa ggcaaaatgc cgcaaaaaag gaataagggc gacacggaa    3060 atgttgaata ctcatactct tcctttttca atattattga agcatttatc agggttattg   3120
tctcatgagc ggatacatat ttgaatgtat ttagaaaaat aaacaaatag gggttccgcg   3180
cacatttccc cgaaaagtgc cacctgatgc ggtgtgaaat accgcacaga tgcgtaagga   3240
gaaaataccg catcaggaaa ttgtaagcgt taatattttg ttaaaattcg cgttaaattt   3300
ttgttaaatc agctcatttt ttaaccaata ggccgaaatc ggcaaaatcc cttataaatc   3360
aaaagaatag accgagatag ggttgagtgt tgttccagtt tggaacaaga gtccactatt   3420
aaagaacgtg gactccaacg tcaaagggcg aaaaaccgtc tatcagggcg atggcccact   3480
acgtgaacca tcaccctaat caagttttt ggggtcgagg tgccgtaaag cactaaatcg   3540
gaaccctaaa gggagccccc gatttagagc ttgacgggga agccggcga acgtggcgag   3600 aaaggaaggg aagaaagcga aggagcggg cgctagggcg ctggcaagtg tagcggtcac   3660
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
cagctggcga aaggggatg tgctgcaagg cgattaagtt gggtaacgcc agggttttcc   3840
```

```
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaaccctc ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580
cagtgccggc gtaggtgaag tcgtcaatga tgtcgatatg gttttgatc atgcacacat    5640
aaggtccgac cttatcggca agctcaatga gctccttggt ggtggtaaca tccagagaag    5700
cacacaggtt ggttttcttg gctgccacga gcttgagcac tcgagcggca aggcggact    5760
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
```

-continued

```
ttaaacagtg tacgcagatc tactatagag gaacatttaa attgccccgg agaagacggc    6240
caggccgcct agatgacaaa ttcaacaact cacagctgac tttctgccat tgccactagg    6300 gggggggcctt tttatatggc caagccaagc tctccacgtc ggttgggctg cacccaacaa    6360
taaatgggta gggttgcacc aacaagggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctgga    6780 tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggggct tgtctagggt atatataaac agtggctctc ccaatcggtt    6960
gccagtctct ttttttccttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatggccac ccacgtcctg gctgccgctg ccgagcgaaa cgctgccctc gctcccgacg    7200
ctcctctggc tcccgtcact atggagcgac ctgtgcgaac cgatctcgaa acctccattc    7260
ccaagcctta catggctcga ggcctggttg ctcccgacat ggatcatccc aacggtactc    7320
ctggacacgt gcacgacaac ctttccgttc tgcagcaaca ctgcgccttc tttgaccagg    7380
atgacaacgg tatcatttac ccctgggaga cctactctgg actcagacag atcggcttca    7440
acgtcattgc ttcgcttatc atggccattg tcatcaacgt tgcactgtct tatcccacat    7500
tgcctggctg gattccctct ccattctttc ctatctacct gtacaacatt cacaaggcca    7560
agcatggttc cgactctgga acctacgaca ccgagggtcg atacctcccc atgaacttcg    7620
agaatctgtt tagcaaacac gctcgaacca tgcccgatag actgactctc ggtgaactgt    7680
ggtctatgac cgaggccaac cgagaggcat tcgacatctt cggctggatt gcctccaaga    7740
tggagtggac ccttctctac atcctggctc gagatcagga cggatttctg tccaaggaag    7800
ccattcgacg ttgttacgac ggctccctct tcgagtactg cgccaagatg cagcgaggtg    7860
ccgaggacaa gatgaagtaa gc    7882
```

<210> SEQ ID NO 47
<211> LENGTH: 8098
<212> TYPE: DNA
<213> ORGANISM: Artificial sequence
<220> FEATURE:
<223> OTHER INFORMATION: Construct pYRH88

<400> SEQUENCE: 47

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgttgattga ggtggagcca gatgggctat tgtttcatat     360
```

```
atagactggc agccacctct ttggcccagc atgtttgtat acctggaagg gaaaactaaa    420
gaagctggct agtttagttt gattattata gtagatgtcc taatcactag agattagaat    480
gtcttggcga tgattagtcg tcgtcccctg tatcatgtct agaccaactg tgtcatgaag    540
ttggtgctgg tgttttacct gtgtactaca agtaggtgtc ctagatctag tgtacagagc    600
cgtttagacc catgtggact tcaccattaa cgatggaaaa tgttcattat atgacagtat    660
attacaatgg acttgctcca tttcttcctt gcatcacatg ttctccacct ccatagttga    720
tcaacacatc atagtagcta aggctgctgc tctcccacta cagtccacca caagttaagt    780
agcaccgtca gtacagctaa aagtacacgt ctagtacgtt tcataactag tcaagtagcc    840
cctattacag atatcagcac tatcacgcac gagttttcct ctgtgctatc taatcaactt    900
gccaagtatt cggagaagat acactttctt ggcatcaggt atacgaggga gcctatcaga    960
tgaaaaggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga aagaacatgt gagcaaaagg ccagcaaaag gccaggaacc gtaaaaaggc    1440
cgcgttgctg gcgttttttcc ataggctccg ccccctgac gagcatcaca aaaatcgacg    1500
ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc caacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaagagt tggtagctct tgatccggca acaaaccac    1980
cgctggtagc ggtggttttt ttgtttgcaa gcagcagatt acgcgcagaa aaaaggatc    2040
tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atccccatg ttgtgcaaaa aagcggttag    2640
ctccttcggt cctccgatcg ttgtcagaag taagttggcc gcagtgttat cactcatggt    2700
```

-continued

```
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcgggc gaaaactctc aaggatctta ccgctgttga gatccagttc     2940
gatgtaaccc actcgtgcac ccaactgatc ttcagcatct tttactttca ccagcgtttc    3000
tgggtgagca aaaacaggaa ggcaaaatgc cgcaaaaaag gaataagggg cgacacggaa    3060
atgttgaata ctcatactct ccttttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360 aaagaatag accgagatag ggttgagtgt tgttccagtt tggaacaaga gtccactatt      3420
aaagaacgtg gactccaacg tcaaagggcg aaaaaccgtc tatcagggcg atggcccact    3480
acgtgaacca tcaccctaat caagttttt ggggtcgagg tgccgtaaag cactaaatcg      3540
gaaccctaaa gggagccccc gatttagagc ttgacgggga agccggcga acgtggcgag     3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aggggggatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaacccta cttcatcaa gtgcaagaac     4020 ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
```

```
cgtctcccct gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggggagca   5580 cagtgccggc gtaggtgaag tcgtcaatga tgtcgatatg ggttttgatc atgcacacat    5640
aaggtccgac cttatcggca agctcaatga gctccttggt ggtggtaaca tccagagaag    5700
cacacaggtt ggttttcttg gctgccacga gcttgagcac tcgagcggca aaggcggact    5760
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300 gggggggcctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca cttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctgga    6780 tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcggggggct tgtctagggt atatataaac agtggctctc ccaatcggtt    6960
gccagtctct tttttccttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatggaggg tgccactacc gctgccggca acaagcaaca ggcacgatct ggtgaccgag    7200
gagccgctaa gaccgccacc gatggcaaga agggcgacgc agacgtggcc aagggagacc    7260
ctgctgccgg tgccaagcag gctgccggcg acgctggcaa gggtggagcc gctgccactg    7320
gtaacaataa gcaggctgcc ggcggagcca tgcaccatca cggttttttcc tctgctgttg    7380 aggccaaaga ttcccagacc attgttgctc tccaggctcc cgtcactgtg acccgacccg    7440
```

```
tcagaggcga ccttgaggaa cacgtgccca agccctacct tgctcgagcc ctcgctgccc    7500
ctgacattta tcaccccgaa ggaacccctg aggatgagca ccgacaccat cacatgtctg    7560
tgctccaaca gcacgtcgcc ttctttgaca gagatgacaa cggtatcatt taccccctggg   7620 agacttactc gggttgccga gctctcggct tcaacatggt cctctccttt ctgatcgccg    7680
tcgttgtgaa cggtacaatg tcttacgcta ccctgcctgg atggcttccc tcccctctct    7740
ttcccatcta tgtccataac atccataagt ctaaacacgg ttccgacttc ggcacctacg    7800
acaacgaggg tcggttcatg ccagtgaact tcgagaacat gttctctaag tacgcacgaa    7860
cttcgcctga cagactcacc tatcgagaac tgtggtccat gaccgaggga ttccgagatg    7920
ccctggacct ctacggttgg gttgcagcca agctggagtg gaccatctta tacgttcttg    7980
cacgagacga tgagggctac ctggctcgag aggccatgcg aagactgtac gatggatctc    8040
tcttcgagta cgtcgaacga cagcggatgc agcacgccca tgccaagatg tcctaagc     8098
```

<210> SEQ ID NO 48
<211> LENGTH: 7993
<212> TYPE: DNA
<213> ORGANISM: Artificial sequence
<220> FEATURE:
<223> OTHER INFORMATION: Construct pYRH89

<400> SEQUENCE: 48

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag     540
ttggtgctgg tgttttacct gtgtactaca agtaggtgtc ctagatctag tgtacagagc     600
cgtttagacc catgtggact tcaccattaa cgatggaaaa tgttcattat atgcacgtat     660
attacaatgg acttgctcca tttcttcctt gcatcacatg ttctccacct ccatagttga     720
tcaacacatc atagtagcta aggctgctgc tctcccacta cagtccacca caagttaagt     780
agcaccgtca gtacagctaa agtacacgt ctagtacgtt tcataactag tcaagtagcc     840
cctattacag atatcagcac tatcacgcac gagtttttct ctgtgctatc taatcaactt     900
gccaagtatt cggagaagat acactttctt ggcatcaggt atacgaggga gcctatcaga     960
tgaaaagggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga aagaacatgt gagcaaaagg ccagcaaaag gccaggaacc gtaaaaaggc    1440
```

```
cgcgttgctg gcgttttcc ataggctccg ccccctgac gagcatcaca aaaatcgacg    1500
ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgcttttctca tagctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca aacaaaccac   1980
cgctggtagc ggtggttttt ttgtttgcaa gcagcagatt acgcgcagaa aaaaaggatc   2040
tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
cggttcccaa cgatcaaggc gagttacatg atcccccatg ttgtgcaaaa aagcggttag   2640
ctccttcggt cctccgatcg ttgtcagaag taagttggcc gcagtgttat cactcatggt   2700
tatggcagca ctgcataatt ctcttactgt catgccatcc gtaagatgct tttctgtgac   2760
tggtgagtac tcaaccaagt cattctgaga atagtgtatg cggcgaccga gttgctcttg   2820
cccggcgtca atacgggata ataccgcgcc acatagcaga actttaaaag tgctcatcat   2880
tggaaaacgt tcttcggggc gaaaactctc aaggatctta ccgctgttga tccagttc    2940 gatgtaaccc actcgtgcac ccaactgatc ttcagcatct tttactttca ccagcgtttc   3000
tgggtgagca aaaacaggaa ggcaaaatgc cgcaaaaaag gaataagggc gacacggaa   3060 atgttgaata ctcatactct tccttttca atattattga agcatttatc agggttattg   3120
tctcatgagc ggatacatat ttgaatgtat ttagaaaaat aaacaaatag gggttccgcg   3180
cacatttccc cgaaaagtgc cacctgatgc ggtgtgaaat accgcacaga tgcgtaagga   3240
gaaaataccg catcaggaaa ttgtaagcgt taatattttg ttaaaattcg cgttaaattt   3300
ttgttaaatc agctcatttt ttaaccaata ggccgaaatc ggcaaaatcc cttataaatc   3360
aaaagaatag accgagatag ggttgagtgt tgttccagtt tggaacaaga gtccactatt   3420
aaagaacgtg gactccaacg tcaaagggcg aaaaaccgtc tatcagggcg atggcccact   3480
acgtgaacca tcaccctaat caagtttttt ggggtcgagg tgccgtaaag cactaaatcg   3540
gaaccctaaa gggagccccc gatttagagc ttgacgggga agccggcga acgtggcgag   3600 aaaggaaggg aagaaagcga aaggagcggg cgctagggcg ctggcaagtg tagcggtcac   3660
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
```

```
cagctggcga aaggggatg tgctgcaagg cgattaagtt gggtaacgcc agggttttcc      3840
cagtcacgac gttgtaaaac gacggccagt gaattgtaat acgactcact atagggcgaa      3900
ttgggcccga cgtcgcatgc attccgacag cagcgactgg gcaccatgat caagcgaaac      3960
accttccccc agctgccctg gcaaaccatc aagaaccta ctttcatcaa gtgcaagaac       4020
ggttctactc ttctcacctc cggtgtctac ggctggtgcc gaaagcctaa ctacaccgct      4080
gatttcatca tgtgcctcac ctgggctctc atgtgcggtg ttgcttctcc cctgccttac     4140
ttctacccgg tcttcttctt cctggtgctc atccaccgag cttaccgaga ctttgagcga     4200
ctggagcgaa agtacggtga ggactaccag gagttcaagc gacaggtccc ttggatcttc     4260
atcccttatg ttttctaaac gataagctta gtgagcgaat ggtgaggtta cttaattgag     4320
tggccagcct atgggattgt ataacagaca gtcaatatat tactgaaaag actgaacagc     4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag cttttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccacccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg tgatatcgg     5460
accactcggc gattcggtga caccggtact ggtgcttgac agtgttgcca atatctgcga    5520
actttctgtc ctcgaacagg aagaaaccgt gcttaagagc aagttccttg aggggagca     5580
cagtgccggc gtaggtgaag tcgtcaatga tgtcgatatg ggttttgatc atgcacacat    5640
aaggtccgac cttatcggca agctcaatga gctccttggt ggtggtaaca tccagagaag    5700
cacacaggtt ggttttcttg gctgccacga gcttgagcac tcgagcggca aaggcggact    5760
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
```

```
ttaaacagtg tacgcagatc tactatagag gaacatttaa attgccccgg agaagacggc    6240
caggccgcct agatgacaaa ttcaacaact cacagctgac tttctgccat tgccactagg    6300
ggggggcctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctgga    6780 tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggct tgtctagggt atatataaac agtggctctc ccaatcggtt    6960
gccagtctct tttttccttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatggctcg aaaggtctcg ttttccgaga cccagcttcc caacttcgac aagcccatcc    7200
gacctccctc catttctgtg gatttctcca ccactgctcc cgagtgtcct gtcaccgctg    7260
cccgagagcc tgctcgatac accaacgact atatcgagaa gcctggtgtt cccagagcca    7320
acaccacagc ctctattgac cgacccgatg gcgacgaatc ctacaccaag cagttttcgg    7380
acttcactcc cctccagcaa cacgtgctgt tttgggacag agatcgagac ggacagatct    7440
atccctggga cacttacatt ggcttcagag agcttggttt caacatgctg ttttcgttcc    7500
tcgccgttct gattatcaat ctcaactttt cctaccccac tcgactcgca cactctttcc    7560
tgcccgaccc ttggtttcga gtgtacgtcg acgctgttca caaggccaaa cacggatccg    7620
actcgaacac ctacgacccc gagggacgat tcgtccctca gtcttttgag aacatgttcg    7680
caaagtacga cagagatggt gacggagccc tcaccctgcg agagctgttc gatatgatgc    7740
atggcaaccg atgcgctgcc gatcccttg gctggggtgc cgctatctgc gagtggggca    7800
ccacatggct tctgatcgag aaagacggaa aggtgtggaa ggaggacgtt cgaggtgtct    7860
acgatggttc tctcttctgg aaggtgcgag aagccaacta ctctggacga ggctggtccc    7920
agggtttccg acctggtctc tggatcaagc gaaccgtcaa gggcgtgctg aacgcctacc    7980
tggacggata agc                                                       7993
```

<210> SEQ ID NO 49
<211> LENGTH: 8044
<212> TYPE: DNA
<213> ORGANISM: Artificial sequence
<220> FEATURE:
<223> OTHER INFORMATION: Construct pYRH90

<400> SEQUENCE: 49

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
```

```
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgttgattga ggtggagcca gatgggctat tgtttcatat    360
atagactggc agccacctct ttggcccagc atgtttgtat acctggaagg gaaaactaaa    420
gaagctggct agtttagttt gattattata gtagatgtcc taatcactag agattagaat    480
gtcttggcga tgattagtcg tcgtcccctg tatcatgtct agaccaactg tgtcatgaag    540
ttggtgctgg tgtttacct gtgtactaca agtaggtgtc ctagatctag tgtacagagc    600
cgtttagacc catgtggact tcaccattaa cgatggaaaa tgttcattat atgacagtat    660
attacaatgg acttgctcca tttcttcctt gcatcacatg ttctccacct ccatagttga    720
tcaacacatc atagtagcta aggctgctgc tctcccacta cagtccacca caagttaagt    780
agcaccgtca gtacagctaa aagtacacgt ctagtacgtt tcataactag tcaagtagcc    840
cctattacag atatcagcac tatcacgcac gagtttttct ctgtgctatc taatcaactt    900
gccaagtatt cggagaagat acactttctt ggcatcaggt atacgaggga gcctatcaga    960 tgaaaaggg tatattggat ccattcatat ccacctacac gttgtcataa tctcctcatt    1020
cacgtgattc atttcgtgac actagtttct cactttcccc cccgcaccta tagtcaactt    1080
ggcggacacg ctacttgtag ctgacgttga tttatagacc caatcaaagc gggttatcgg    1140
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga aagaacatgt gagcaaaagg ccagcaaaag gccaggaacc gtaaaaaggc    1440
cgcgttgctg gcgtttttcc ataggctccg cccccctgac gagcatcaca aaaatcgacg    1500
ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc caacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca aacaaaccac    1980
cgctggtagc ggtggttttt ttgtttgcaa gcagcagatt acgcgcagaa aaaaaggatc    2040
tcaagaagat cctttgatct ttctacgggg tctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
```

```
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcgggc gaaaactctc aaggatctta ccgctgttga gatccagttc    2940
gatgtaaccc actcgtgcac ccaactgatc ttcagcatct tttactttca ccagcgtttc    3000
tgggtgagca aaaacaggaa ggcaaaatgc cgcaaaaaag gaataagggc gacacggaaa    3060
atgttgaata ctcatactct tcctttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagttttt ggggtcgagg tgccgtaaag cactaaatcg    3540
gaaccctaaa gggagcccc gatttagagc ttgacgggga agccggcga acgtggcgag    3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aggggatg tgctgcaagg cgattaagtt gggtaacgcc agggttttcc    3840
cagtcacgac gttgtaaaac gacggccagt gaattgtaat acgactcact ataggcgaa    3900 ttgggcccga cgtcgcatgc attccgacag cagcgactgg gcaccatgat caagcgaaac    3960
accttccccc agctgccctg gcaaaccatc aagaaccta ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagacccctcg cgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
```

```
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctcccct gtcgtcaaga cccacccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580
cagtgccggc gtaggtgaag tcgtcaatga tgtcgatatg gttttgatc atgcacacat    5640
aaggtccgac cttatcggca agctcaatga gctccttggt ggtggtaaca tccagagaag    5700
cacacaggtt ggttttcttg gctgccacga gcttgagcac tcgagcggca aggcggact    5760
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300
gggggggcctt tttatatggc caagccaagc tctccacgtc ggttgggctg cacccaacaa    6360
taaatgggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
gggtggtgtg acttgttata gcctttagag ctgcgaaagc gcgtatggat ttggctcatc    6720
aggccagatt gagggtctgt ggacacatgt catgttagtg tacttcaatc gcccctgga    6780
tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggggct tgtctagggt atatataaac agtggctctc ccaatcggtt    6960
gccagtctct tttttccttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatggccgt ccgagtcgtt cctcgagagg acgagcaggt ggacgacgaa cgacagggcg    7200
ttgattttgc caccgctgtg tccaactgtc ctcccactgc cgagcgacca caggccatcg    7260
acattgatgt ggacatctat aagccctcta ttgccagagc caacgttgct ccctcgaccg    7320
```

-continued

| | |
|---|---|
| aacagcccga aggctccgct gagtacgtgg acgccctcga tctgaaggac tacaccgttc | 7380 |
| ttcagcaaca ctgtatgttc tgggacagag atcgagatgg agtcatctgg cctcaggaca | 7440 |
| ctttcattgg cttttacgag ttaggtttca acctctttt ctgctttctg gccactctcg | 7500 |
| tcatcaatct gaacttctct tacccactc gactgggcgt gtcctacatt cccgacccat | 7560 |
| actttcgact ctacctgccc tctatgcaca aggccaagca tggctccgac tcaggtacct | 7620 |
| atgacaagga aggacgattc gttccccagg ctttcgagga catgttctcg aagtgggatc | 7680 |
| gaggagacaa gggtgctctt tccgctggcg agctgtggaa catgattgct gccaaccgac | 7740 |
| tcgcagccga cccttcggt tgggctgccg aatcttcga gtttggtgtc acctggctgc | 7800 |
| tcgtgcaaca ggacggcatg gtcgacaagg aggaccttcg acggatctac gatggttcta | 7860 |
| tgttctttaa gatcagagag gcataccgaa cagagaaggg atggaacaag ggtttcggtc | 7920 |
| tctgcgagtt ctttaactta ggtcgagagc agtgggccaa gaacaaagga cgaatccctc | 7980 |
| ccctgaacgg cattgtctcc aaggtggagc gatctgtcac ccagaagctt caccgagctt | 8040 |
| aagc | 8044 |

<210> SEQ ID NO 50
<211> LENGTH: 741
<212> TYPE: DNA
<213> ORGANISM: Artificial sequence
<220> FEATURE:
<223> OTHER INFORMATION: cys-AtClo1s (AtClo1s modified to contain added cysteine residues in the N-and C-terminal regions of the AtClo1s polypeptide)

<400> SEQUENCE: 50

| | |
|---|---|
| atgggctgct ccaagaccga gatgatggag cgatgcgcta tggccaccgt cgctccttac | 60 |
| gcacccgtta cctactgccg aagagcccga gtcgacctgg acgattgtct tcccaaacct | 120 |
| tacatgcctc gagccctgtg tgctcctgac cgagagcatc cctacggaac tcctggtcac | 180 |
| aagaactacg gcctctccgt gctgcagcag catgtctctt tctttgacat tgatgacaac | 240 |
| ggaatcattt accctggga gacctactcc ggtctgcgga tgctcggctt caacatcatt | 300 |
| ggatctctga tcattgccgc tgtcatcaac cttacactca gctacgccac cctgcctggt | 360 |
| tggcttccct ctccttctt tcccatctac attcacaaca ttcataagtc caagcacggc | 420 |
| tccgacagca gacttacga caatgaagga cgattcatgc ccgtcaacct cgagctgatc | 480 |
| ttctcgaagt acgccaagac cctgcccgac aagctctcct gggagagct gtgggagatg | 540 |
| accgaaggca accgagatgc ttgggacatc tttggatgga ttgccggcaa gatcgagtgg | 600 |
| tgtctgctct acctgctcgc ttgcgacgag gaaggcttct tgtccaagga ggccattcga | 660 |
| agatgctttg acggttctct gttcgagtac tgtgccaaga tctatgctgg tatcagcgag | 720 |
| tgtaagaccg catactatta a | 741 |

<210> SEQ ID NO 51
<211> LENGTH: 246
<212> TYPE: PRT
<213> ORGANISM: Artificial sequence
<220> FEATURE:
<223> OTHER INFORMATION: cys-AtClo1s polypeptide (AtClo1s modified to contain added cysteine residues in the N-and C-terminal regions of the AtClo1s polypeptide)

<400> SEQUENCE: 51

Met Gly Cys Ser Lys Thr Glu Met Met Glu Arg Cys Ala Met Ala Thr
1               5                   10                  15

Val Ala Pro Tyr Ala Pro Val Thr Tyr Cys Arg Arg Ala Arg Val Asp
            20                  25                  30

Leu Asp Asp Cys Leu Pro Lys Pro Tyr Met Pro Arg Ala Leu Cys Ala
         35                  40                  45

Pro Asp Arg Glu His Pro Tyr Gly Thr Pro Gly His Lys Asn Tyr Gly
     50                  55                  60

Leu Ser Val Leu Gln Gln His Val Ser Phe Phe Asp Ile Asp Asp Asn
65                  70                  75                  80

Gly Ile Ile Tyr Pro Trp Glu Thr Tyr Ser Gly Leu Arg Met Leu Gly
                 85                  90                  95

Phe Asn Ile Ile Gly Ser Leu Ile Ile Ala Ala Val Ile Asn Leu Thr
            100                 105                 110

Leu Ser Tyr Ala Thr Leu Pro Gly Trp Leu Pro Ser Pro Phe Phe Pro
            115                 120                 125

Ile Tyr Ile His Asn Ile His Lys Ser Lys His Gly Ser Asp Ser Lys
    130                 135                 140

Thr Tyr Asp Asn Glu Gly Arg Phe Met Pro Val Asn Leu Glu Leu Ile
145                 150                 155                 160

Phe Ser Lys Tyr Ala Lys Thr Leu Pro Asp Lys Leu Ser Leu Gly Glu
                165                 170                 175

Leu Trp Glu Met Thr Glu Gly Asn Arg Asp Ala Trp Asp Ile Phe Gly
            180                 185                 190

Trp Ile Ala Gly Lys Ile Glu Trp Cys Leu Leu Tyr Leu Leu Ala Cys
        195                 200                 205

Asp Glu Glu Gly Phe Leu Ser Lys Glu Ala Ile Arg Arg Cys Phe Asp
    210                 215                 220

Gly Ser Leu Phe Glu Tyr Cys Ala Lys Ile Tyr Ala Gly Ile Ser Glu
225                 230                 235                 240

Cys Lys Thr Ala Tyr Tyr
                245

<210> SEQ ID NO 52
<211> LENGTH: 2757
<212> TYPE: DNA
<213> ORGANISM: Artificial sequence
<220> FEATURE:
<223> OTHER INFORMATION: cys-AtClo1s::PDAT fusion protein

<400> SEQUENCE: 52

| | | | | | |
|---|---|---|---|---|---|
| atgggctgct | ccaagaccga | gatgatggag | cgatgcgcta | tggccaccgt | cgctccttac | 60 |
| gcaccgtta | cctactgccg | aagagcccga | gtcgacctgg | acgattgtct | tcccaaacct | 120 |
| tacatgcctc | gagccctgtg | tgctcctgac | cgagagcatc | cctacggaac | tcctggtcac | 180 |
| aagaactacg | gcctctccgt | gctgcagcag | catgtctctt | tctttgacat | tgatgacaac | 240 |
| ggaatcattt | accctgggga | gacctactcc | ggtctgcgga | tgctcggctt | caacatcatt | 300 |
| ggatctctga | tcattgccgc | tgtcatcaac | cttacactca | gctacgccac | cctgcctggt | 360 |
| tggcttccct | ctcccttctt | tcccatctac | attcacaaca | ttcataagtc | caagcacggc | 420 |
| tccgacagca | agacttacga | caatgaagga | cgattcatgc | ccgtcaacct | cgagctgatc | 480 |
| ttctcgaagt | acgccaagac | cctgcccgac | aagctctcct | gggagagct | gtgggagatg | 540 |
| accgaaggca | accgagatgc | ttgggacatc | tttggatgga | ttgccggcaa | gatcgagtgg | 600 |
| tgtctgctct | acctgctcgc | ttgcgacgag | gaaggcttct | tgtccaagga | ggccattcga | 660 |
| agatgctttg | acggttctct | gttcgagtac | tgtgccaaga | tctatgctgg | tatcagcgag | 720 |

```
tgtaagaccg catactatgg cgccggtccc gctcgacctg ccggacttcc tcccgctacc    780
tactacgact ctctggccgt catgggatcc atgacacaac ctgtgaatcg aaggcgact     840 gtcgagcggg tcgagccagc agtggaggtg gctgactccg agtccgaggc caagaccgac    900
gtccacgttc accaccatca tcaccaccac aagcgaaaat ccgtcaaggg caagattctc    960
aacttcttca cccgaagtcg acgtatcacc ttcgtcctcg agccgtggt cggtgtgata    1020 gccgcgggat actacgctgc gccaccggag ctcagcattg atatcgacgc tcttctcggc   1080
gacttgccct cgttcgactt tgacgctcta tctctcgaca acttgtcgat ggacagtgtg   1140
tcggactttg tacaagacat gaaatcgcgg tttccgacca agattctgca ggaggcggcc   1200
aagatcgaga agcaccagaa aagcgaacag aaggctgccc ttttgctgt gggcaaggct    1260 atgaagagcg agggactcaa cgccaagtac cggtggtgc tggtgcccgg cgtcatctcc    1320
acgggactgg agagctggtc cctggaggga accgaggagt gtcccaccga gtcgcacttc   1380
agaaagcgaa tgtggggctc ctggtacatg atccgagtca tgctgctgga caagtactgc   1440
tggctgcaga acctgatgct ggacacagag accggtctag accctcccca tttcaagctg   1500
cgagccgccc agggatttgc ctccgccgac ttctttatgg caggctactg gctgtggaac   1560
aagctgctcg agaacctggc tgttattgga tacgatacgg atacaatgtc tgctgccgcg   1620
tacgactgga gactgtccta ccctgatttg gagcaccgag acggatactt ctccaagctc   1680
aaagcttcaa tcgaagagac taagcgtatg acaggtgaga agacagttct gacgggccat   1740
tctatgggct cccaggtcat cttctacttc atgaagtggg ctgaggccga gggatatgga   1800
ggaggaggtc ccaactgggt caatgaccat attgaatcct ttgtcgacat ttccggctcc   1860
atgctgggta ctcccaagac cctggttgct cttctgtctg gagaaatgaa ggataccgtg   1920
cagctgaacg cgatggctgt gtatggactg gagcagttct tctctcgacg agagcgagcc   1980
gatctgctgc gaacatgggg aggaattgct tccatgattc ccaagggtgg taaggctatc   2040
tggggtgatc attctggagc ccctgatgac gagcccggcc agaatgtcac ctttggcaac   2100
ttcatcaagt tcaaggagtc cttgaccgag tactctgcta agaacctcac tatggatgaa   2160
accgttgact tcctgtattc tcagtctccc gagtggtttg tgaaccgaac cgagggtgct   2220
tactcctttg gaattgccaa gactcgaaag caggttgagc agaatgagaa gcgaccttct   2280
acctggagca cccctctgga agctgctctc cccaatgccc ccgatctcaa gatctactgc   2340
ttctatggag tcggtaagga taccgagcga gcctactact accaggatga gcccaatccc   2400
gagcagacca acttgaacgt cagtatcgct ggaaacgacc ctgatggtgt gcttatgggt   2460
cagggcgatg gaaccgtctc ccttgtgacc cataccatgt gtcaccgatg gaaggacgag   2520
aactccaagt tcaaccctgg taacgcccag gtcaaggttg tggagatgtt gcaccagcct   2580
gatcgacttg atattcgagg cggtgctcag actgccgagc atgtggacat tctgggcgt    2640 tctgagttga acgagatggt tctgaaggtg gctagtggaa agggaaatga gattgaagag   2700
agagtcatct ccaacattga tgagtgggtg tggaagattg atctcggcag caattag      2757
```

<210> SEQ ID NO 53
<211> LENGTH: 918
<212> TYPE: PRT
<213> ORGANISM: Artificial sequence
<220> FEATURE:
<223> OTHER INFORMATION: cys-AtClo1s::PDAT fusion protein

<400> SEQUENCE: 53

Met Gly Cys Ser Lys Thr Glu Met Met Glu Arg Cys Ala Met Ala Thr
1               5                   10                  15

Val Ala Pro Tyr Ala Pro Val Thr Tyr Cys Arg Arg Ala Arg Val Asp
            20                  25                  30

Leu Asp Asp Cys Leu Pro Lys Pro Tyr Met Pro Arg Ala Leu Cys Ala
        35                  40                  45

Pro Asp Arg Glu His Pro Tyr Gly Thr Pro Gly His Lys Asn Tyr Gly
50                  55                  60

Leu Ser Val Leu Gln Gln His Val Ser Phe Phe Asp Ile Asp Asp Asn
65                  70                  75                  80

Gly Ile Ile Tyr Pro Trp Glu Thr Tyr Ser Gly Leu Arg Met Leu Gly
                85                  90                  95

Phe Asn Ile Ile Gly Ser Leu Ile Ile Ala Ala Val Ile Asn Leu Thr
            100                 105                 110

Leu Ser Tyr Ala Thr Leu Pro Gly Trp Leu Pro Ser Pro Phe Phe Pro
        115                 120                 125

Ile Tyr Ile His Asn Ile His Lys Ser Lys His Gly Ser Asp Ser Lys
130                 135                 140

Thr Tyr Asp Asn Glu Gly Arg Phe Met Pro Val Asn Leu Glu Leu Ile
145                 150                 155                 160

Phe Ser Lys Tyr Ala Lys Thr Leu Pro Asp Lys Leu Ser Leu Gly Glu
                165                 170                 175

Leu Trp Glu Met Thr Glu Gly Asn Arg Asp Ala Trp Asp Ile Phe Gly
            180                 185                 190

Trp Ile Ala Gly Lys Ile Glu Trp Cys Leu Leu Tyr Leu Leu Ala Cys
        195                 200                 205

Asp Glu Glu Gly Phe Leu Ser Lys Glu Ala Ile Arg Arg Cys Phe Asp
210                 215                 220

Gly Ser Leu Phe Glu Tyr Cys Ala Lys Ile Tyr Ala Gly Ile Ser Glu
225                 230                 235                 240

Cys Lys Thr Ala Tyr Tyr Gly Ala Gly Pro Ala Arg Pro Ala Gly Leu
                245                 250                 255

Pro Pro Ala Thr Tyr Tyr Asp Ser Leu Ala Val Met Gly Ser Met Thr
            260                 265                 270

Gln Pro Val Asn Arg Lys Ala Thr Val Glu Arg Val Glu Pro Ala Val
        275                 280                 285

Glu Val Ala Asp Ser Glu Ser Glu Ala Lys Thr Asp Val His Val His
290                 295                 300

His His His His His Lys Arg Lys Ser Val Lys Gly Lys Ile Leu
305                 310                 315                 320

Asn Phe Phe Thr Arg Ser Arg Arg Ile Thr Phe Val Leu Gly Ala Val
                325                 330                 335

Val Gly Val Ile Ala Ala Gly Tyr Tyr Ala Ala Pro Pro Glu Leu Ser
            340                 345                 350

Ile Asp Ile Asp Ala Leu Leu Gly Asp Leu Pro Ser Phe Asp Phe Asp
        355                 360                 365

Ala Leu Ser Leu Asp Asn Leu Ser Met Asp Ser Val Ser Asp Phe Val
370                 375                 380

Gln Asp Met Lys Ser Arg Phe Pro Thr Lys Ile Leu Gln Glu Ala Ala
385                 390                 395                 400

Lys Ile Glu Lys His Gln Lys Ser Glu Gln Lys Ala Ala Pro Phe Ala
                405                 410                 415

Val Gly Lys Ala Met Lys Ser Glu Gly Leu Asn Ala Lys Tyr Pro Val

```
            420             425             430
Val Leu Val Pro Gly Val Ile Ser Thr Gly Leu Glu Ser Trp Ser Leu
            435             440             445

Glu Gly Thr Glu Glu Cys Pro Thr Glu Ser His Phe Arg Lys Arg Met
            450             455             460

Trp Gly Ser Trp Tyr Met Ile Arg Val Met Leu Leu Asp Lys Tyr Cys
465             470             475             480

Trp Leu Gln Asn Leu Met Leu Asp Thr Glu Thr Gly Leu Asp Pro Pro
            485             490             495

His Phe Lys Leu Arg Ala Ala Gln Gly Phe Ala Ser Ala Asp Phe Phe
            500             505             510

Met Ala Gly Tyr Trp Leu Trp Asn Lys Leu Leu Glu Asn Leu Ala Val
            515             520             525

Ile Gly Tyr Asp Thr Asp Thr Met Ser Ala Ala Tyr Asp Trp Arg
            530             535             540

Leu Ser Tyr Pro Asp Leu Glu His Arg Asp Gly Tyr Phe Ser Lys Leu
545             550             555             560

Lys Ala Ser Ile Glu Glu Thr Lys Arg Met Thr Gly Glu Lys Thr Val
            565             570             575

Leu Thr Gly His Ser Met Gly Ser Gln Val Ile Phe Tyr Phe Met Lys
            580             585             590

Trp Ala Glu Ala Glu Gly Tyr Gly Gly Gly Pro Asn Trp Val Asn
            595             600             605

Asp His Ile Glu Ser Phe Val Asp Ile Ser Gly Ser Met Leu Gly Thr
            610             615             620

Pro Lys Thr Leu Val Ala Leu Leu Ser Gly Glu Met Lys Asp Thr Val
625             630             635             640

Gln Leu Asn Ala Met Ala Val Tyr Gly Leu Glu Gln Phe Phe Ser Arg
            645             650             655

Arg Glu Arg Ala Asp Leu Leu Arg Thr Trp Gly Gly Ile Ala Ser Met
            660             665             670

Ile Pro Lys Gly Gly Lys Ala Ile Trp Gly Asp His Ser Gly Ala Pro
            675             680             685

Asp Asp Glu Pro Gly Gln Asn Val Thr Phe Gly Asn Phe Ile Lys Phe
            690             695             700

Lys Glu Ser Leu Thr Glu Tyr Ser Ala Lys Asn Leu Thr Met Asp Glu
705             710             715             720

Thr Val Asp Phe Leu Tyr Ser Gln Ser Pro Glu Trp Phe Val Asn Arg
            725             730             735

Thr Glu Gly Ala Tyr Ser Phe Gly Ile Ala Lys Thr Arg Lys Gln Val
            740             745             750

Glu Gln Asn Glu Lys Arg Pro Ser Thr Trp Ser Asn Pro Leu Glu Ala
            755             760             765

Ala Leu Pro Asn Ala Pro Asp Leu Lys Ile Tyr Cys Phe Tyr Gly Val
            770             775             780

Gly Lys Asp Thr Glu Arg Ala Tyr Tyr Tyr Gln Asp Glu Pro Asn Pro
785             790             795             800

Glu Gln Thr Asn Leu Asn Val Ser Ile Ala Gly Asn Asp Pro Asp Gly
            805             810             815

Val Leu Met Gly Gln Gly Asp Gly Thr Val Ser Leu Val Thr His Thr
            820             825             830

Met Cys His Arg Trp Lys Asp Glu Asn Ser Lys Phe Asn Pro Gly Asn
            835             840             845
```

```
Ala Gln Val Lys Val Val Glu Met Leu His Gln Pro Asp Arg Leu Asp
    850                 855                 860

Ile Arg Gly Gly Ala Gln Thr Ala Glu His Val Asp Ile Leu Gly Arg
865                 870                 875                 880

Ser Glu Leu Asn Glu Met Val Leu Lys Val Ala Ser Gly Lys Gly Asn
                885                 890                 895

Glu Ile Glu Glu Arg Val Ile Ser Asn Ile Asp Glu Trp Val Trp Lys
                900                 905                 910

Ile Asp Leu Gly Ser Asn
        915

<210> SEQ ID NO 54
<211> LENGTH: 2757
<212> TYPE: DNA
<213> ORGANISM: Artificial sequence
<220> FEATURE:
<223> OTHER INFORMATION: PDAT::cys-AtClo1s fusion protein

<400> SEQUENCE: 54
```

| | |
|---|---|
| atggccacac aacctgtgaa tcggaaggcg actgtcgagc gggtcgagcc agcagtggag | 60 |
| gtggctgact ccgagtccga ggccaagacc gacgtccacg ttcaccacca tcatcaccac | 120 |
| cacaagcgaa atccgtcaa gggcaagatt ctcaacttct tcacccgaag tcgacgtatc | 180 |
| accttcgtcc tcggagccgt ggtcggtgtg atagccgcgg atactacgc tgccgccaccg | 240 |
| gagctcagca ttgatatcga cgctcttctc ggcgacttgc cctcgttcga ctttgacgct | 300 |
| ctatctctcg acaacttgtc gatggacagt gtgtcggact tgtacaaga catgaaatcg | 360 |
| cggtttccga ccaagattct gcaggaggcg gccaagatcg agaagcacca gaaaagcgaa | 420 |
| cagaaggctg ccccttttgc tgtgggcaag gctatgaaga gcgagggact caacgccaag | 480 |
| tacccggtgg tgctggtgcc cggcgtcatc tccacgggac tggagagctg gtccctggag | 540 |
| ggaaccgagg agtgtcccac cgagtcgcac ttcagaaagc gaatgtgggg ctcctggtac | 600 |
| atgatccgag tcatgctgct ggacaagtac tgctggctgc agaacctgat gctggacaca | 660 |
| gagaccggtc tagaccctcc ccatttcaag ctgcgagccg cccagggatt tgcctccgcc | 720 |
| gacttcttta tggcaggcta ctggctgtgg aacaagctgc tcgagaacct ggctgttatt | 780 |
| ggatacgata cggatacaat gtctgctgcc gcgtacgact ggagactgtc ctaccctgat | 840 |
| ttggagcacc gagacggata cttctccaag ctcaaagctt caatcgaaga gactaagcgt | 900 |
| atgacaggtg agaagacagt tctgacgggc cattctatgg gctcccaggt catcttctac | 960 |
| ttcatgaagt gggctgaggc cgagggatat ggaggaggag gtcccaactg ggtcaatgac | 1020 |
| catattgaat cctttgtcga catttccggc tccatgctgg gtactcccaa gaccctggtt | 1080 |
| gctcttctgt ctggagaaat gaaggatacc gtgcagctga acgcgatggc tgtgtatgga | 1140 |
| ctggagcagt tcttctctcg acgagagcga gccgatctgc tgcgaacatg ggaggaattt | 1200 |
| gcttccatga ttcccaaggg tggtaaggct atctggggtg atcattctgg agcccctgat | 1260 |
| gacgagcccg gccagaatgt caccttttggc aacttcatca agttcaagga gtccttgacc | 1320 |
| gagtactctg ctaagaacct cactatggat gaaaccgttg acttcctgta ttctcagtct | 1380 |
| cccgagtggt ttgtgaaccg aaccgagggt gcttactcct ttggaattgc caagactcga | 1440 |
| aagcaggttg agcagaatga gaagcgacct tctacctgga gcaaccctct ggaagctgct | 1500 |
| ctccccaatg cccccgatct caagatctac tgcttctatg gagtcggtaa ggataccgag | 1560 |
| cgagcctact actaccagga tgagcccaat cccgagcaga ccaacttgaa cgtcagtatc | 1620 |

-continued

```
gctggaaacg accctgatgg tgtgcttatg ggtcagggcg atggaaccgt ctcccttgtg    1680
acccatacca tgtgtcaccg atggaaggac gagaactcca agttcaaccc tggtaacgcc    1740
caggtcaagg ttgtggagat gttgcaccag cctgatcgac ttgatattcg aggcggtgct    1800
cagactgccg agcatgtgga cattctgggg cgttctgagt tgaacgagat ggttctgaag    1860
gtggctagtg aaagggaaa tgagattgaa gagagagtca tctccaacat tgatgagtgg     1920
gtgtggaaga ttgatctcgg cagcaatggc gccggtcccg ctcgacctgc cggacttcct    1980
cccgctacct actacgactc tctggccgtc atgggatcca tgtgctccaa gaccgagatg    2040
atggagcgat cgctatggc caccgtcgct ccttacgcac ccgttaccta ctgccgaaga     2100
gcccgagtcg acctggacga ttgtcttccc aaaccttaca tgcctcgagc cctgtgtgct    2160
cctgaccgag agcatcccta cggaactcct ggtcacaaga actacggcct ctccgtgctg    2220
cagcagcatg tctctttctt tgacattgat gacaacggaa tcatttaccc ctgggagacc    2280
tactccggtc tgcggatgct cggcttcaac atcattggat ctctgatcat tgccgctgtc    2340
atcaacctta cactcagcta cgccaccctg cctggttggc ttccctctcc cttctttccc    2400
atctacattc acaacattca taagtccaag cacggctccg acagcaagac ttacgacaat    2460
gaaggacgat tcatgcccgt caacctcgag ctgatcttct cgaagtacgc caagaccctg    2520
cccgacaagc tctccttggg agagctgtgg gagatgaccg aaggcaaccg agatgcttgg    2580
gacatctttg gatggattgc cggcaagatc gagtggtgtc tgctctacct gctcgcttgc    2640
gacgaggaag gcttcttgtc caaggaggcc attcgaagat gctttgacgg ttctctgttc    2700
gagtactgtg ccaagatcta tgctggtatc agcgagtgta agaccgcata ctattaa      2757
```

<210> SEQ ID NO 55
<211> LENGTH: 918
<212> TYPE: PRT
<213> ORGANISM: Artificial sequence
<220> FEATURE:
<223> OTHER INFORMATION: PDAT::cys-AtClo1s fusion protein

<400> SEQUENCE: 55

```
Met Ala Thr Gln Pro Val Asn Arg Lys Ala Thr Val Glu Arg Val Glu
1               5                   10                  15

Pro Ala Val Glu Val Ala Asp Ser Glu Ser Glu Ala Lys Thr Asp Val
            20                  25                  30

His Val His His His His His His Lys Arg Lys Ser Val Lys Gly
        35                  40                  45

Lys Ile Leu Asn Phe Phe Thr Arg Ser Arg Arg Ile Thr Phe Val Leu
    50                  55                  60

Gly Ala Val Val Gly Val Ile Ala Ala Gly Tyr Tyr Ala Ala Pro Pro
65                  70                  75                  80

Glu Leu Ser Ile Asp Ile Asp Ala Leu Leu Gly Asp Leu Pro Ser Phe
            85                  90                  95

Asp Phe Asp Ala Leu Ser Leu Asp Asn Leu Ser Met Asp Ser Val Ser
            100                 105                 110

Asp Phe Val Gln Asp Met Lys Ser Arg Phe Pro Thr Lys Ile Leu Gln
            115                 120                 125

Glu Ala Ala Lys Ile Glu Lys His Gln Lys Ser Glu Gln Lys Ala Ala
        130                 135                 140

Pro Phe Ala Val Gly Lys Ala Met Lys Ser Glu Gly Leu Asn Ala Lys
145                 150                 155                 160
```

```
Tyr Pro Val Val Leu Val Pro Gly Val Ile Ser Thr Gly Leu Glu Ser
            165                 170                 175

Trp Ser Leu Glu Gly Thr Glu Glu Cys Pro Thr Glu Ser His Phe Arg
        180                 185                 190

Lys Arg Met Trp Gly Ser Trp Tyr Met Ile Arg Val Met Leu Leu Asp
    195                 200                 205

Lys Tyr Cys Trp Leu Gln Asn Leu Met Leu Asp Thr Glu Thr Gly Leu
210                 215                 220

Asp Pro Pro His Phe Lys Leu Arg Ala Ala Gln Gly Phe Ala Ser Ala
225                 230                 235                 240

Asp Phe Phe Met Ala Gly Tyr Trp Leu Trp Asn Lys Leu Leu Glu Asn
            245                 250                 255

Leu Ala Val Ile Gly Tyr Asp Thr Asp Thr Met Ser Ala Ala Ala Tyr
            260                 265                 270

Asp Trp Arg Leu Ser Tyr Pro Asp Leu Glu His Arg Asp Gly Tyr Phe
        275                 280                 285

Ser Lys Leu Lys Ala Ser Ile Glu Glu Thr Lys Arg Met Thr Gly Glu
    290                 295                 300

Lys Thr Val Leu Thr Gly His Ser Met Gly Ser Gln Val Ile Phe Tyr
305                 310                 315                 320

Phe Met Lys Trp Ala Glu Ala Glu Gly Tyr Gly Gly Gly Pro Asn
            325                 330                 335

Trp Val Asn Asp His Ile Glu Ser Phe Val Asp Ile Ser Gly Ser Met
            340                 345                 350

Leu Gly Thr Pro Lys Thr Leu Val Ala Leu Leu Ser Gly Glu Met Lys
        355                 360                 365

Asp Thr Val Gln Leu Asn Ala Met Ala Val Tyr Gly Leu Glu Gln Phe
    370                 375                 380

Phe Ser Arg Arg Glu Arg Ala Asp Leu Leu Arg Thr Trp Gly Gly Ile
385                 390                 395                 400

Ala Ser Met Ile Pro Lys Gly Gly Lys Ala Ile Trp Gly Asp His Ser
            405                 410                 415

Gly Ala Pro Asp Asp Glu Pro Gly Gln Asn Val Thr Phe Gly Asn Phe
            420                 425                 430

Ile Lys Phe Lys Glu Ser Leu Thr Glu Tyr Ser Ala Lys Asn Leu Thr
        435                 440                 445

Met Asp Glu Thr Val Asp Phe Leu Tyr Ser Gln Ser Pro Glu Trp Phe
    450                 455                 460

Val Asn Arg Thr Glu Gly Ala Tyr Ser Phe Gly Ile Ala Lys Thr Arg
465                 470                 475                 480

Lys Gln Val Glu Gln Asn Glu Lys Arg Pro Ser Thr Trp Ser Asn Pro
            485                 490                 495

Leu Glu Ala Ala Leu Pro Asn Ala Pro Asp Leu Lys Ile Tyr Cys Phe
            500                 505                 510

Tyr Gly Val Gly Lys Asp Thr Glu Arg Ala Tyr Tyr Gln Asp Glu
        515                 520                 525

Pro Asn Pro Glu Gln Thr Asn Leu Asn Val Ser Ile Ala Gly Asn Asp
    530                 535                 540

Pro Asp Gly Val Leu Met Gly Gln Gly Asp Gly Thr Val Ser Leu Val
545                 550                 555                 560

Thr His Thr Met Cys His Arg Trp Lys Asp Glu Asn Ser Lys Phe Asn
            565                 570                 575

Pro Gly Asn Ala Gln Val Lys Val Val Glu Met Leu His Gln Pro Asp
```

```
            580                 585                 590
Arg Leu Asp Ile Arg Gly Gly Ala Gln Thr Ala Glu His Val Asp Ile
        595                 600                 605

Leu Gly Arg Ser Glu Leu Asn Glu Met Val Leu Lys Val Ala Ser Gly
        610                 615                 620

Lys Gly Asn Glu Ile Glu Arg Val Ile Ser Asn Ile Asp Glu Trp
625                 630                 635                 640

Val Trp Lys Ile Asp Leu Gly Ser Asn Gly Ala Gly Pro Ala Arg Pro
                645                 650                 655

Ala Gly Leu Pro Pro Ala Thr Tyr Tyr Asp Ser Leu Ala Val Met Gly
            660                 665                 670

Ser Met Cys Ser Lys Thr Glu Met Met Glu Arg Cys Ala Met Ala Thr
            675                 680                 685

Val Ala Pro Tyr Ala Pro Val Thr Tyr Cys Arg Arg Ala Arg Val Asp
            690                 695                 700

Leu Asp Asp Cys Leu Pro Lys Pro Tyr Met Pro Arg Ala Leu Cys Ala
705                 710                 715                 720

Pro Asp Arg Glu His Pro Tyr Gly Thr Pro Gly His Lys Asn Tyr Gly
                725                 730                 735

Leu Ser Val Leu Gln Gln His Val Ser Phe Phe Asp Ile Asp Asp Asn
                740                 745                 750

Gly Ile Ile Tyr Pro Trp Glu Thr Tyr Ser Gly Leu Arg Met Leu Gly
            755                 760                 765

Phe Asn Ile Ile Gly Ser Leu Ile Ile Ala Ala Val Ile Asn Leu Thr
        770                 775                 780

Leu Ser Tyr Ala Thr Leu Pro Gly Trp Leu Pro Ser Pro Phe Phe Pro
785                 790                 795                 800

Ile Tyr Ile His Asn Ile His Lys Ser Lys His Gly Ser Asp Ser Lys
                805                 810                 815

Thr Tyr Asp Asn Glu Gly Arg Phe Met Pro Val Asn Leu Glu Leu Ile
                820                 825                 830

Phe Ser Lys Tyr Ala Lys Thr Leu Pro Asp Lys Leu Ser Leu Gly Glu
        835                 840                 845

Leu Trp Glu Met Thr Glu Gly Asn Arg Asp Ala Trp Asp Ile Phe Gly
850                 855                 860

Trp Ile Ala Gly Lys Ile Glu Trp Cys Leu Leu Tyr Leu Leu Ala Cys
865                 870                 875                 880

Asp Glu Glu Gly Phe Leu Ser Lys Glu Ala Ile Arg Arg Cys Phe Asp
                885                 890                 895

Gly Ser Leu Phe Glu Tyr Cys Ala Lys Ile Tyr Ala Gly Ile Ser Glu
            900                 905                 910

Cys Lys Thr Ala Tyr Tyr
        915

<210> SEQ ID NO 56
<211> LENGTH: 2346
<212> TYPE: DNA
<213> ORGANISM: Artificial sequence
<220> FEATURE:
<223> OTHER INFORMATION: cys-AtClo1s::LPCAT fusion protein

<400> SEQUENCE: 56
atgggctgct ccaagaccga gatgatggag cgatgcgcta tggccaccgt cgctccttac    60
gcacccgtta cctactgccg aagagcccga gtcgacctgg acgattgtct tcccaaacct   120
```

```
tacatgcctc gagccctgtg tgctcctgac cgagagcatc cctacggaac tcctggtcac     180
aagaactacg gcctctccgt gctgcagcag catgtctctt tctttgacat tgatgacaac     240
ggaatcattt accccgggga gacctactcc ggtctgcgga tgctcggctt caacatcatt     300
ggatctctga tcattgccgc tgtcatcaac cttacactca gctacgccac cctgcctggt     360
tggcttccct ctcccttctt tcccatctac attcacaaca ttcataagtc caagcacggc     420
tccgacagca agacttacga caatgaagga cgattcatgc ccgtcaacct cgagctgatc     480
ttctcgaagt acgccaagac cctgcccgac aagctctcct gggagagct gtgggagatg     540 accgaaggca accgagatgc ttgggacatc tttggatgga ttgccggcaa gatcgagtgg     600
tgtctgctct acctgctcgc ttgcgacgag gaaggcttct tgtccaagga ggccattcga     660
agatgctttg acggttctct gttcgagtac tgtgccaaga tctatgctgg tatcagcgag     720
tgtaagaccg catactatgg cgccggtccc gctcgacctg ccggacttcc tcccgctacc     780
tactacgact ctctggccgt catgggatcc gccttcccct gggctgacaa gtgggctgcc     840
gacgcttccg cttctaccgg actgcctccc gatctgctca agattgcctt caccctggtt     900
atgtcgtacc ctctctcttc cctgatgaag cgacttcccg acgatgccaa gaacctgaag     960
atcatttaca tcatttccgt gtctatcttc tacatggtcg gtgtgttttc gctgtacggc    1020
ggagccgcta ctctgctctt ctcctctatg ggcaccttct ttatcactca gtggaagtct    1080
ccctacatgc cttgggtcaa cttcggattt gttatgactc acctcttcgt caaccacctg    1140
cgatcccagt tctttcccga gacctacgac cctaacgtca tcgacattac tggtgctcag    1200
atggttctct gtatgaagct gtcctcgttc ggctggaacg tctacgacgg atggcagatc    1260
gagaagggcg aacaactttc cgagttccag accaagcgag ccgtgctcaa gcatccctct    1320
ctcatggact ttctggcctt cgtcttttac tttccctcca ttctcactgg tccttcctac    1380
gactacatgg agtttcacaa ctggctggat ctttctctct tcaaggaact ggagaaagac    1440
aaggatccca gcgagccgc tcgacggaag cgacacaaga ttcctcgatc tggcatcgca    1500
gcttcgaaaa agctcgctgc cggaatcttc tggattgtgc tgtggaccca ggtcgactct    1560
cgaatttcca ctgcctatgc ttactcggat gccttcacca aggagcacaa catcttcgga    1620
cgaattgtct atttgtacat gctgggcttc atgtaccgac tcaagtacta tggtgcttgg    1680
tccatctcgg aaggagcctg cattctctcc ggtctgggct ttcatggtgt tgatcccaag    1740
accggaaagt acaagtggga ccgagttcag aacgtcgatc cttggggctt cgagaccggt    1800
cagaacacca aggctctgct cgaggcctgg aaccagaaca ccaacaagtg gcttcgaaac    1860
tacgtctatc tgcgagtggt ccccaagggc cagaagcctg gatttcgagc taccatcttc    1920
acttttgtcg tgtctgcctt ctggcacggt acccgacccg gctactatct caccttttgtt    1980 acagccgcta tgtaccagag cgtcggcaag ttctttagac gatacctgcg accttctttt    2040
atggagtccg acggaaagac cgcaggtcct acaagatct attcgacat tgtctgttgg    2100 atcgtggttc aaaccgcttt cggctacgcc actcagtcct tcatgattct cgacttctgg    2160
ctgtctctca gtgctggaa gaactcgtgg tttctctacc atatcgcctt gggagctatc    2220
tttgccattt cctctcccta caaggcctgg gctatcccta agatcaagaa aaagcaggcc    2280
ggtgctgtta ccgacaaaaa ggatgccaag gaggaggtca aaaaggacac tatcaaaacc    2340
aagtaa                                                               2346

<210> SEQ ID NO 57
<211> LENGTH: 781
```

<212> TYPE: PRT
<213> ORGANISM: Artificial sequence
<220> FEATURE:
<223> OTHER INFORMATION: cys-AtClo1s::LPCAT fusion protein

<400> SEQUENCE: 57

Met Gly Cys Ser Lys Thr Glu Met Met Glu Arg Cys Ala Met Ala Thr
1               5                   10                  15

Val Ala Pro Tyr Ala Pro Val Thr Tyr Cys Arg Arg Ala Arg Val Asp
            20                  25                  30

Leu Asp Asp Cys Leu Pro Lys Pro Tyr Met Pro Arg Ala Leu Cys Ala
        35                  40                  45

Pro Asp Arg Glu His Pro Tyr Gly Thr Pro Gly His Lys Asn Tyr Gly
    50                  55                  60

Leu Ser Val Leu Gln Gln His Val Ser Phe Phe Asp Ile Asp Asn
65                  70                  75                  80

Gly Ile Ile Tyr Pro Trp Glu Thr Tyr Ser Gly Leu Arg Met Leu Gly
                85                  90                  95

Phe Asn Ile Ile Gly Ser Leu Ile Ala Ala Val Ile Asn Leu Thr
                100                 105                 110

Leu Ser Tyr Ala Thr Leu Pro Gly Trp Leu Pro Ser Pro Phe Phe Pro
            115                 120                 125

Ile Tyr Ile His Asn Ile His Lys Ser Lys His Gly Ser Asp Ser Lys
130                 135                 140

Thr Tyr Asp Asn Glu Gly Arg Phe Met Pro Val Asn Leu Glu Leu Ile
145                 150                 155                 160

Phe Ser Lys Tyr Ala Lys Thr Leu Pro Asp Lys Leu Ser Leu Gly Glu
                165                 170                 175

Leu Trp Glu Met Thr Glu Gly Asn Arg Asp Ala Trp Asp Ile Phe Gly
            180                 185                 190

Trp Ile Ala Gly Lys Ile Glu Trp Cys Leu Leu Tyr Leu Leu Ala Cys
        195                 200                 205

Asp Glu Glu Gly Phe Leu Ser Lys Glu Ala Ile Arg Arg Cys Phe Asp
    210                 215                 220

Gly Ser Leu Phe Glu Tyr Cys Ala Lys Ile Tyr Ala Gly Ile Ser Glu
225                 230                 235                 240

Cys Lys Thr Ala Tyr Tyr Gly Ala Gly Pro Ala Arg Pro Ala Gly Leu
                245                 250                 255

Pro Pro Ala Thr Tyr Tyr Asp Ser Leu Ala Val Met Gly Ser Ala Phe
            260                 265                 270

Pro Trp Ala Asp Lys Trp Ala Ala Asp Ala Ser Ala Ser Thr Gly Leu
        275                 280                 285

Pro Pro Asp Leu Leu Lys Ile Ala Phe Thr Leu Val Met Ser Tyr Pro
    290                 295                 300

Leu Ser Ser Leu Met Lys Arg Leu Pro Asp Asp Ala Lys Asn Leu Lys
305                 310                 315                 320

Ile Ile Tyr Ile Ile Ser Val Ser Ile Phe Tyr Met Val Gly Val Phe
                325                 330                 335

Ser Leu Tyr Gly Gly Ala Ala Thr Leu Leu Phe Ser Ser Met Gly Thr
            340                 345                 350

Phe Phe Ile Thr Gln Trp Lys Ser Pro Tyr Met Pro Trp Val Asn Phe
        355                 360                 365

Gly Phe Val Met Thr His Leu Val Asn His Leu Arg Ser Gln Phe
    370                 375                 380

Phe Pro Glu Thr Tyr Asp Pro Asn Val Ile Asp Ile Thr Gly Ala Gln
385                 390                 395                 400

Met Val Leu Cys Met Lys Leu Ser Ser Phe Gly Trp Asn Val Tyr Asp
            405                 410                 415

Gly Trp Gln Ile Glu Lys Gly Glu Gln Leu Ser Glu Phe Gln Thr Lys
        420                 425                 430

Arg Ala Val Leu Lys His Pro Ser Leu Met Asp Phe Leu Ala Phe Val
    435                 440                 445

Phe Tyr Phe Pro Ser Ile Leu Thr Gly Pro Ser Tyr Asp Tyr Met Glu
450                 455                 460

Phe His Asn Trp Leu Asp Leu Ser Leu Phe Lys Glu Leu Glu Lys Asp
465                 470                 475                 480

Lys Asp Pro Lys Arg Ala Ala Arg Arg Lys Arg His Lys Ile Pro Arg
            485                 490                 495

Ser Gly Ile Ala Ala Ser Lys Lys Leu Ala Ala Gly Ile Phe Trp Ile
        500                 505                 510

Val Leu Trp Thr Gln Val Asp Ser Arg Ile Ser Thr Ala Tyr Ala Tyr
    515                 520                 525

Ser Asp Ala Phe Thr Lys Glu His Asn Ile Phe Gly Arg Ile Val Tyr
530                 535                 540

Leu Tyr Met Leu Gly Phe Met Tyr Arg Leu Lys Tyr Tyr Gly Ala Trp
545                 550                 555                 560

Ser Ile Ser Glu Gly Ala Cys Ile Leu Ser Gly Leu Gly Phe His Gly
            565                 570                 575

Val Asp Pro Lys Thr Gly Lys Tyr Lys Trp Asp Arg Val Gln Asn Val
        580                 585                 590

Asp Pro Trp Gly Phe Glu Thr Gly Gln Asn Thr Lys Ala Leu Leu Glu
    595                 600                 605

Ala Trp Asn Gln Asn Thr Asn Lys Trp Leu Arg Asn Tyr Val Tyr Leu
610                 615                 620

Arg Val Val Pro Lys Gly Gln Lys Pro Gly Phe Arg Ala Thr Ile Phe
625                 630                 635                 640

Thr Phe Val Val Ser Ala Phe Trp His Gly Thr Arg Pro Gly Tyr Tyr
            645                 650                 655

Leu Thr Phe Val Thr Ala Ala Met Tyr Gln Ser Val Gly Lys Phe Phe
        660                 665                 670

Arg Arg Tyr Leu Arg Pro Phe Phe Met Glu Ser Asp Gly Lys Thr Ala
    675                 680                 685

Gly Pro Tyr Lys Ile Tyr Tyr Asp Ile Val Cys Trp Ile Val Val Gln
690                 695                 700

Thr Ala Phe Gly Tyr Ala Thr Gln Ser Phe Met Ile Leu Asp Phe Trp
705                 710                 715                 720

Leu Ser Leu Lys Cys Trp Lys Asn Ser Trp Phe Leu Tyr His Ile Ala
            725                 730                 735

Leu Gly Ala Ile Phe Ala Ile Ser Ser Pro Tyr Lys Ala Trp Ala Ile
        740                 745                 750

Pro Lys Ile Lys Lys Lys Gln Ala Gly Ala Val Thr Asp Lys Lys Asp
    755                 760                 765

Ala Lys Glu Glu Val Lys Lys Asp Thr Ile Lys Thr Lys
770                 775                 780

<210> SEQ ID NO 58
<211> LENGTH: 2346
<212> TYPE: DNA

<213> ORGANISM: Artificial sequence
<220> FEATURE:
<223> OTHER INFORMATION: LPCAT::cys-AtClo1s fusion protein

<400> SEQUENCE: 58

```
atggccttcc cctgggctga caagtgggct gccgacgctt ccgcttctac cggactgcct      60
cccgatctgc tcaagattgc cttcaccctg gttatgtcgt accctctctc ttccctgatg     120
aagcgacttc ccgacgatgc caagaacctg aagatcattt acatcatttc cgtgtctatc     180
ttctacatgg tcggtgtgtt ttcgctgtac ggcggagccg ctactctgct cttctcctct     240
atgggcacct tctttatcac tcagtggaag tctccctaca tgccttgggt caacttcgga     300
tttgttatga ctcacctctt cgtcaaccac ctgcgatccc agttctttcc cgagacctac     360
gaccctaacg tcatcgacat tactggtgct cagatggttc tctgtatgaa gctgtcctcg     420
ttcggctgga acgtctacga cggatggcag atcgagaagg gcgaacaact ttccgagttc     480
cagaccaagc gagccgtgct caagcatccc tctctcatgg actttctggc cttcgtcttt     540
tactttcccc tccattctca ctggtcctcc tacgactaca tggagtttca aactggctg      600
gatctttctc tcttcaagga actggagaaa gacaaggatc ccaagcgagc cgctcgacgg     660
aagcgacaca agattcctcg atctggcatc gcagcttcga aaaagctcgc tgccggaatc     720
ttctggattg tgctgtggac ccaggtcgac tctcgaattt ccactgccta tgcttactcg     780
gatgccttca ccaaggagca aacatcttc ggacgaattc tctatttgta catgctgggc      840
ttcatgtacc gactcaagta ctatggtgct tggtccatct cggaaggagc ctgcattctc     900
tccggtctgg gctttcatgg tgttgatccc aagaccggaa agtacaagtg ggaccgagtt     960
cagaacgtcg atccttgggg cttcgagacc ggtcagaaca ccaaggctct gctcgaggcc    1020
tggaaccaga acaccaacaa gtggcttcga aactacgtct atctgcgagt ggtccccaag    1080
ggccagaagc ctggatttcg agctaccatc ttcactttg tcgtgtctgc cttctggcac     1140
ggtacccgac ccggctacta tctcaccttt gttacagccg ctatgtacca gagcgtcggc    1200
aagttcttta cgatacct gcgacccttc tttatggagt ccgacggaaa gaccgcaggt      1260
ccttacaaga tctattacga cattgtctgt tggatcgtgg ttcaaaccgc tttcggctac    1320
gccactcagt ccttcatgat tctcgacttc tggctgtctc tcaagtgctg aagaactcg     1380
tggtttctct accatatcgc cttgggagct atctttgcca tttcctctcc ctacaaggcc    1440
tgggctatcc ctaagatcaa gaaaaagcag gccggtgctg ttaccgacaa aaaggatgcc    1500
aaggaggagg tcaaaaagga cactatcaaa accaagggcg ccgtcccgc tcgacctgcc     1560
ggacttcctc ccgctaccta ctacgactct ctggccgtca tgggatccat gtgctccaag    1620
accgagatga tggagcgatg cgctatggcc accgtcgctc cttacgcacc cgttacctac    1680
tgccgaagag cccgagtcga cctggacgat tgtcttccca aaccttacat gcctcgagcc    1740
ctgtgtgctc ctgaccgaga gcatccctac ggaactcctg gtcacaagaa ctacggcctc    1800
tccgtgctgc agcagcatgt ctcttctctt gacattgatg acaacggaat catttacccc    1860
tgggagacct actccggtct gcggatgctc ggcttcaaca tcattggatc tctgatcatt    1920
gccgctgtca tcaaccttac actcagctac gccaccctgc ctggttggct ccctctcccc    1980
ttctttccca tctacattca caacattcat aagtccaagc acggctccga cagcaagact    2040
tacgacaatg aaggacgatt catgcccgtc aacctcgagc tgatcttctc gaagtacgcc    2100
aagaccctgc ccgacaagct ctccttggga gagctgtggg agatgaccga aggcaaccga    2160
gatgcttggg acatctttgg atggattgcc ggcaagatcg agtggtgtct gctctacctg    2220
```

```
ctcgcttgcg acgaggaagg cttcttgtcc aaggaggcca ttcgaagatg ctttgacggt    2280
tctctgttcg agtactgtgc caagatctat gctggtatca gcgagtgtaa gaccgcatac    2340
tattaa                                                                2346
```

<210> SEQ ID NO 59
<211> LENGTH: 781
<212> TYPE: PRT
<213> ORGANISM: Artificial sequence
<220> FEATURE:
<223> OTHER INFORMATION: LPCAT::cys-AtClo1s fusion protein

<400> SEQUENCE: 59

```
Met Ala Phe Pro Trp Ala Asp Lys Trp Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335
```

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Ser Ala Phe Trp His Gly Thr Arg Pro
370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Val Lys Lys Asp Thr Ile Lys Thr Lys
            500                 505                 510

Gly Ala Gly Pro Ala Arg Pro Ala Gly Leu Pro Pro Ala Thr Tyr Tyr
            515                 520                 525

Asp Ser Leu Ala Val Met Gly Ser Met Cys Ser Lys Thr Glu Met Met
    530                 535                 540

Glu Arg Cys Ala Met Ala Thr Val Ala Pro Tyr Ala Pro Val Thr Tyr
545                 550                 555                 560

Cys Arg Arg Ala Arg Val Asp Leu Asp Asp Cys Leu Pro Lys Pro Tyr
                565                 570                 575

Met Pro Arg Ala Leu Cys Ala Pro Asp Arg Glu His Pro Tyr Gly Thr
            580                 585                 590

Pro Gly His Lys Asn Tyr Gly Leu Ser Val Leu Gln Gln His Val Ser
        595                 600                 605

Phe Phe Asp Ile Asp Asp Asn Gly Ile Ile Tyr Pro Trp Glu Thr Tyr
    610                 615                 620

Ser Gly Leu Arg Met Leu Gly Phe Asn Ile Ile Gly Ser Leu Ile Ile
625                 630                 635                 640

Ala Ala Val Ile Asn Leu Thr Leu Ser Tyr Ala Thr Leu Pro Gly Trp
                645                 650                 655

Leu Pro Ser Pro Phe Phe Pro Ile Tyr Ile His Asn Ile His Lys Ser
            660                 665                 670

Lys His Gly Ser Asp Ser Lys Thr Tyr Asp Asn Glu Gly Arg Phe Met
        675                 680                 685

Pro Val Asn Leu Glu Leu Ile Phe Ser Lys Tyr Ala Lys Thr Leu Pro
    690                 695                 700

Asp Lys Leu Ser Leu Gly Glu Leu Trp Glu Met Thr Glu Gly Asn Arg
705                 710                 715                 720

Asp Ala Trp Asp Ile Phe Gly Trp Ile Ala Gly Lys Ile Glu Trp Cys
                725                 730                 735

Leu Leu Tyr Leu Leu Ala Cys Asp Glu Glu Gly Phe Leu Ser Lys Glu
            740                 745                 750
```

Ala Ile Arg Arg Cys Phe Asp Gly Ser Leu Phe Glu Tyr Cys Ala Lys
    755                   760                765

Ile Tyr Ala Gly Ile Ser Glu Cys Lys Thr Ala Tyr Tyr
    770                   775                780

<210> SEQ ID NO 60
<211> LENGTH: 24
<212> TYPE: PRT
<213> ORGANISM: Artificial sequence
<220> FEATURE:
<223> OTHER INFORMATION: Linker used in fusion proteins

<400> SEQUENCE: 60

Gly Ala Gly Pro Ala Arg Pro Ala Gly Leu Pro Pro Ala Thr Tyr Tyr
1             5                  10                 15

Asp Ser Leu Ala Val Met Gly Ser
          20

<210> SEQ ID NO 61
<211> LENGTH: 7885
<212> TYPE: DNA
<213> ORGANISM: Artificial sequence
<220> FEATURE:
<223> OTHER INFORMATION: Construct pYRH95

<400> SEQUENCE: 61

| | | | | | |
|---|---|---|---|---|---|
| ggccgcaagt | gtggatgggg | aagtgagtgc | ccggttctgt | gtgcacaatt | ggcaatccaa | 60 |
| gatggatgga | ttcaacacag | ggatatagcg | agctacgtgg | tggtgcgagg | atatagcaac | 120 |
| ggatatttat | gtttgacact | tgagaatgta | cgatacaagc | actgtccaag | tacaatacta | 180 |
| aacatactgt | acatactcat | actcgtaccc | gggcaacggt | ttcacttgag | tgcagtggct | 240 |
| agtgctctta | ctcgtacagt | gtgcaatact | gcgtatcata | gtctttgatg | tatatcgtat | 300 |
| tcattcatgt | tagttgcgta | cgttgattga | ggtggagcca | gatgggctat | tgtttcatat | 360 |
| atagactggc | agccacctct | ttggcccagc | atgtttgtat | acctggaagg | gaaaactaaa | 420 |
| gaagctggct | agtttagttt | gattattata | gtagatgtcc | taatcactag | agattagaat | 480 |
| gtcttggcga | tgattagtcg | tcgtcccctg | tatcatgtct | agaccaactg | tgtcatgaag | 540 |
| ttggtgctgg | tgttttacct | gtgtactaca | agtaggtgtc | ctagatctag | tgtacagagc | 600 |
| cgtttagacc | catgtggact | tcaccattaa | cgatggaaaa | tgttcattat | atgacagtat | 660 |
| attacaatgg | acttgctcca | tttcttcctt | gcatcacatg | ttctccacct | ccatagttga | 720 |
| tcaacacatc | atagtagcta | aggctgctgc | tctcccacta | cagtccacca | caagttaagt | 780 |
| agcaccgtca | gtacagctaa | aagtacacgt | ctagtacgtt | tcataactag | tcaagtagcc | 840 |
| cctattacag | atatcagcac | tatcacgcac | gagtttttct | ctgtgctatc | taatcaactt | 900 |
| gccaagtatt | cggagaagat | acactttctt | ggcatcaggt | atacgaggga | gcctatcaga | 960 |
| tgaaaaaggg | tatattggat | ccattcatat | ccacctacac | gttgtcataa | tctcctcatt | 1020 |
| cacgtgattc | atttcgtgac | actagtttct | cactttcccc | cccgcaccta | tagtcaactt | 1080 |
| ggcggacacg | ctacttgtag | ctgacgttga | tttatagacc | caatcaaagc | gggttatcgg | 1140 |
| tcaggtagca | cttatcattc | atcgttcata | ctacgatgag | caatctcggg | catgtccgga | 1200 |
| aaagtgtcgg | gcgcgccagc | tgcattaatg | aatcggccaa | cgcgcgggga | gaggcggttt | 1260 |
| gcgtattggg | cgctcttccg | cttcctcgct | cactgactcg | ctgcgctcgg | tcgttcggct | 1320 |
| gcggcgagcg | gtatcagctc | actcaaaggc | ggtaatacgg | ttatccacag | aatcagggga | 1380 |
| taacgcagga | aagaacatgt | gagcaaaagg | ccagcaaaag | gccaggaacc | gtaaaaaggc | 1440 |

-continued

```
cgcgttgctg gcgttttcc ataggctccg cccccctgac gagcatcaca aaaatcgacg    1500
ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgcttttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc aacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaagagt tggtagctct tgatccggca aacaaaccac    1980
cgctggtagc ggtggttttt ttgtttgcaa gcagcagatt acgcgcagaa aaaaggatc    2040 tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcggggc gaaaactctc aaggatctta ccgctgttga gatccagttc    2940
gatgtaaccc actcgtgcac ccaactgatc ttcagcatct tttactttca ccagcgtttc    3000
tgggtgagca aaaacaggaa ggcaaaatgc cgcaaaaaag gaataagggg cgacacggaa    3060
atgttgaata ctcatactct tccttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagtttttt ggggtcgagg tgccgtaaag cactaaatcg    3540
gaaccctaaa gggagccccc gatttagagc ttgacgggga agccggcga acgtggcgag    3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
```

```
cagctggcga aaggggatg tgctgcaagg cgattaagtt gggtaacgcc agggttttcc      3840
cagtcacgac gttgtaaaac gacggccagt gaattgtaat acgactcact atagggcgaa      3900
ttgggcccga cgtcgcatgc attccgacag cagcgactgg gcaccatgat caagcgaaac      3960
accttccccc agctgccctg gcaaaccatc aagaaccta ctttcatcaa gtgcaagaac      4020
ggttctactc ttctcacctc cggtgtctac ggctggtgcc gaaagcctaa ctacaccgct      4080
gatttcatca tgtgcctcac ctgggctctc atgtgcggtg ttgcttctcc cctgccttac      4140
ttctacccgg tcttcttctt cctggtgctc atccaccgag cttaccgaga ctttgagcga      4200
ctggagcgaa agtacggtga ggactaccag gagttcaagc gacaggtccc ttggatcttc      4260
atcccttatg tttctaaac gataagctta gtgagcgaat ggtgaggtta cttaattgag      4320
tggccagcct atgggattgt ataacagaca gtcaatatat tactgaaaag actgaacagc      4380
cagacggagt gaggttgtga gtgaatcgta gagggcggct attacagcaa gtctactcta      4440
cagtgtacta acacagcaga gaacaaatac aggtgtgcat tcggctatct gagaattagt      4500
tggagagctc gagaccctcg gcgataaact gctcctcggt tttgtgtcca tacttgtacg      4560
gaccattgta atggggcaag tcgttgagtt ctcgtcgtcc gacgttcaga gcacagaaac      4620
caatgtaatc aatgtagcag agatggtcct gcaaaagatt gatttgtgcg agcaggttaa      4680
ttaagtcata cacaagtcag cttcttcga gcctcatata agtataagta gttcaacgta      4740
ttagcactgt acccagcatc tccgtatcga gaaacacaac aacatgccc attggacaga      4800
tcatgcggat acacaggttg tgcagtatca tacatactcg atcagacagg tcgtctgacc      4860
atcatacaag ctgaacaagc gctccatact tgcacgctct ctatatacac agttaaatta      4920
catatccata gtctaacctc taacagttaa tcttctggta agcctcccag ccagccttct      4980
ggtatcgctt ggcctcctca ataggatctc ggttctggcc gtacagacct cggccgacaa      5040
ttatgatatc cgttccggta gacatgacat cctcaacagt tcggtactgc tgtccgagag      5100
cgtctccctt gtcgtcaaga cccaccccgg gggtcagaat aagccagtcc tcagagtcgc      5160
ccttaggtcg gttctgggca atgaagccaa ccacaaactc ggggtcggat cgggcaagct      5220
caatggtctg cttggagtac tcgccagtgg ccagagagcc cttgcaagac agctcggcca      5280
gcatgagcag acctctggcc agcttctcgt tgggagaggg gactaggaac tccttgtact      5340
gggagttctc gtagtcagag acgtcctcct tcttctgttc agagacagtt tcctcggcac      5400
cagctcgcag gccagcaatg attccggttc cgggtacacc gtgggcgttg tgatatcgg      5460
accactcggc gattcggtga caccggtact ggtgcttgac agtgttgcca atatctgcga      5520
actttctgtc ctcgaacagg aagaaaccgt gcttaagagc aagttccttg aggggagca      5580
cagtgccggc gtaggtgaag tcgtcaatga tgtcgtatg ggttttgatc atgcacacat      5640
aaggtccgac cttatcggca agctcaatga gctccttggt ggtggtaaca tccagagaag      5700
cacacaggtt ggttttcttg gctgccacga gcttgagcac tcgagcggca aaggcggact      5760
tgtggacgtt agctcgagct tcgtaggagg gcattttggt ggtgaagagg agactgaaat      5820
aaatttagtc tgcagaactt tttatcggaa ccttatctgg ggcagtgaag tatatgttat      5880
ggtaatagtt acgagttagt tgaacttata gatagactgg actatacggc tatcggtcca      5940
aattagaaag aacgtcaatg gctctctggg cgtcgccttt gccgacaaaa atgtgatcat      6000
gatgaaagcc agcaatgacg ttgcagctga tattgttgtc ggccaaccgc gccgaaaacg      6060
cagctgtcag acccacagcc tccaacgaag aatgtatcgt caaagtgatc caagcacact      6120
catagttgga gtcgtactcc aaaggcggca atgacgagtc agacagatac tcgtcgacgt      6180
```

-continued

```
ttaaacagtg tacgcagatc tactatagag gaacatttaa attgccccgg agaagacggc      6240
caggccgcct agatgacaaa ttcaacaact cacagctgac tttctgccat tgccactagg      6300
gggggccctt tttatatggc caagccaagc tctccacgtc ggttgggctg cacccaacaa      6360
taaatgggta gggttgcacc aacaaaggga tgggatgggg ggtagaagat acgaggataa      6420
cggggctcaa tggcacaaat aagaacgaat actgccatta agactcgtga tccagcgact      6480
gacaccattg catcatctaa gggcctcaaa actacctcgg aactgctgcg ctgatctgga      6540
caccacagag gttccgagca ctttaggttg caccaaatgt cccaccaggt gcaggcagaa      6600
aacgctggaa cagcgtgtac agtttgtctt aacaaaaagt gagggcgctg aggtcgagca      6660
gggtggtgtg acttgttata gcctttagag ctgcgaaagc gcgtatggat ttggctcatc      6720
aggccagatt gagggtctgt ggacacatgt catgttagtg tacttcaatc gcccctgga      6780 tatagccccg acaataggcc gtggcctcat tttttttgcct tccgcacatt tccattgctc      6840
gatacccaca ccttgcttct cctgcacttg ccaaccttaa tactggttta cattgaccaa      6900
catcttacaa gcgggggggct tgtctagggt atatataaac agtggctctc ccaatcggtt      6960
gccagtctct ttttttcctttt ctttcccccac agattcgaaa tctaaactac acatcacaga      7020
attccgagcc gtgagtatcc acgacaagat cagtgtcgag acgacgcgtt ttgtgtaatg      7080
acacaatccg aaagtcgcta gcaacacaca ctctctacac aaactaaccc agctctggta      7140
ccatgggctg ctccaagacc gagatgatgg agcgatgcgc tatggccacc gtcgctcctt      7200
acgcacccgt tacctactgc cgaagagccc gagtcgacct ggacgattgt cttcccaaac      7260
cttacatgcc tcgagccctg tgtgctcctg accgagagca tccctacgga actcctggtc      7320
acaagaacta cggcctctcc gtgctgcagc agcatgtctc tttctttgac attgatgaca      7380
acggaatcat ttaccccctgg gagacctact ccggtctgcg gatgctcggc ttcaacatca      7440
ttggatctct gatcattgcc gctgtcatca accttacact cagctacgcc accctgcctg      7500
gttggcttcc ctctcccttc tttcccatct acattcacaa cattcataag tccaagcacg      7560
gctccgacag caagacttac gacaatgaag gacgattcat gcccgtcaac ctcgagctga      7620
tcttctcgaa gtacgccaag accctgcccg acaagctctc cttgggagag ctgtgggaga      7680
tgaccgaagg caaccgagat gcttgggaca tctttggatg gattgccggc aagatcgagt      7740
ggtgtctgct ctacctgctc gcttgcgacg aggaaggctt cttgtccaag gaggccattc      7800
gaagatgctt tgacggttct ctgttcgagt actgtgccaa gatctatgct ggtatcagcg      7860
agtgtaagac cgcatactat taagc                                            7885
```

<210> SEQ ID NO 62
<211> LENGTH: 9901
<212> TYPE: DNA
<213> ORGANISM: Artificial sequence
<220> FEATURE:
<223> OTHER INFORMATION: Construct pYRH96

<400> SEQUENCE: 62

```
ggccgcaagt gtggatgggg aagtgagtgc ccggttctgt gtgcacaatt ggcaatccaa        60
gatggatgga ttcaacacag ggatatagcg agctacgtgg tggtgcgagg atatagcaac       120
ggatatttat gtttgacact tgagaatgta cgatacaagc actgtccaag tacaatacta       180
aacatactgt acatactcat actcgtaccc gggcaacgtt tcacttgag tgcagtggct       240 agtgctctta ctcgtacagt gtgcaatact gcgtatcata gtctttgatg tatatcgtat       300
```

-continued

```
tcattcatgt tagttgcgta cgttgattga ggtggagcca gatgggctat tgtttcatat    360
atagactggc agccacctct ttggcccagc atgtttgtat acctggaagg gaaaactaaa    420
gaagctggct agtttagttt gattattata gtagatgtcc taatcactag agattagaat    480
gtcttggcga tgattagtcg tcgtcccctg tatcatgtct agaccaactg tgtcatgaag    540
ttggtgctgg tgttttacct gtgtactaca agtaggtgtc ctagatctag tgtacagagc    600
cgtttagacc catgtggact tcaccattaa cgatggaaaa tgttcattat atgacagtat    660
attacaatgg acttgctcca tttcttcctt gcatcacatg ttctccacct ccatagttga    720
tcaacacatc atagtagcta aggctgctgc tctcccacta cagtccacca caagttaagt    780
agcaccgtca gtacagctaa agtacacgt ctagtacgtt tcataactag tcaagtagcc    840
cctattacag atatcagcac tatcacgcac gagttttttct ctgtgctatc taatcaactt    900
gccaagtatt cggagaagat acactttctt ggcatcaggt atacgaggga gcctatcaga    960
tgaaaaggg tatattggat ccattcatat ccacctacac gttgtcataa tctcctcatt   1020
cacgtgattc atttcgtgac actagtttct cactttcccc cccgcaccta tagtcaactt   1080
ggcggacacg ctacttgtag ctgacgttga tttatagacc caatcaaagc gggttatcgg   1140
tcaggtagca cttatcattc atcgttcata ctacgatgag caatctcggg catgtccgga   1200
aaagtgtcgg gcgcgccagc tgcattaatg aatcggccaa cgcgcgggga gaggcggttt   1260
gcgtattggg cgctcttccg cttcctcgct cactgactcg ctgcgctcgg tcgttcggct   1320
gcggcgagcg gtatcagctc actcaaaggc ggtaatacgg ttatccacag aatcagggga   1380
taacgcagga aagaacatgt gagcaaaagg ccagcaaaag gccaggaacc gtaaaaaggc   1440
cgcgttgctg gcgttttttcc ataggctccg ccccccctgac gagcatcaca aaaatcgacg   1500
ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgctttctca tagctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca aacaaaccac   1980
cgctggtagc ggtggttttt ttgtttgcaa gcagcagatt acgcgcagaa aaaaaggatc   2040
tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
cggttcccaa cgatcaaggc gagttacatg atcccccatg ttgtgcaaaa aagcggttag   2640
ctccttcggt cctccgatcg ttgtcagaag taagttggcc gcagtgttat cactcatggt   2700
```

```
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcggggc gaaaactctc aaggatctta ccgctgttga gatccagttc    2940
gatgtaaccc actcgtgcac ccaactgatc ttcagcatct tttactttca ccagcgtttc    3000
tgggtgagca aaaacaggaa ggcaaaatgc cgcaaaaaag gaataagggc gacacggaa     3060 atgttgaata ctcatactct tcctttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagttttt ggggtcgagg tgccgtaaag cactaaatcg    3540
gaaccctaaa gggagccccc gatttagagc ttgacgggga agccggcga acgtggcgag    3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aggggggatg tgctgcaagg cgattaagtt gggtaacgcc aggggttttcc   3840 cagtcacgac gttgtaaaac gacggccagt gaattgtaat acgactcact ataggggcgaa   3900 ttgggcccga cgtcgcatgc attccgacag cagcgactgg gcaccatgat caagcgaaac    3960
accttccccc agctgccctg gcaaaccatc aagaaccct ctttcatcaa gtgcaagaac     4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
```

```
ttatgatatc cgttccggta gacatgacat cctcaacagt tcggtactgc tgtccgagag   5100
cgtctccctt gtcgtcaaga cccaccccgg gggtcagaat aagccagtcc tcagagtcgc   5160
ccttaggtcg gttctgggca atgaagccaa ccacaaactc ggggtcggat cgggcaagct   5220
caatggtctg cttggagtac tcgccagtgg ccagagagcc cttgcaagac agctcggcca   5280
gcatgagcag acctctggcc agcttctcgt tgggagaggg gactaggaac tccttgtact   5340
gggagttctc gtagtcagag acgtcctcct tcttctgttc agagacagtt tcctcggcac   5400
cagctcgcag gccagcaatg attccggttc cgggtacacc gtgggcgttg gtgatatcgg   5460
accactcggc gattcggtga caccggtact ggtgcttgac agtgttgcca atatctgcga   5520
actttctgtc ctcgaacagg aagaaaccgt gcttaagagc aagttccttg aggggagca   5580 cagtgccggc gtaggtgaag tcgtcaatga tgtcgatatg ggttttgatc atgcacacat   5640
aaggtccgac cttatcggca agctcaatga gctccttggt ggtggtaaca tccagagaag   5700
cacacaggtt ggttttcttg gctgccacga gcttgagcac tcgagcggca aggcggact   5760 tgtggacgtt agctcgagct tcgtaggagg gcattttggt ggtgaagagg agactgaaat   5820
aaatttagtc tgcagaactt tttatcgaaa ccttatctgg ggcagtgaag tatatgttat   5880
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
cagctgtcag acccacagcc tccaacgaag aatgtatcgt caaagtgatc caagcacact   6120
catagttgga gtcgtactcc aaaggcggca atgacgagtc agacagatac tcgtcgacgt   6180
ttaaacagtg tacgcagatc tactatagag gaacatttaa attgccccgg agaagacggc   6240
caggccgcct agatgacaaa ttcaacaact cacagctgac tttctgccat tgccactagg   6300 gggggggcctt tttatatggc caagccaagc tctccacgtc ggttgggctg cacccaacaa   6360
taaatgggta gggttgcacc aacaaaggga tgggatgggg ggtagaagat acgaggataa   6420
cggggctcaa tggcacaaat aagaacgaat actgccatta agactcgtga tccagcgact   6480
gacaccattg catcatctaa gggcctcaaa actacctcgg aactgctgcg ctgatctgga   6540
caccacagag gttccgagca cttaggttg caccaaatgt cccaccaggt gcaggcagaa   6600
aacgctggaa cagcgtgtac agtttgtctt aacaaaaagt gagggcgctg aggtcgagca   6660
gggtggtgtg acttgttata gcctttagag ctgcgaaagc gcgtatggat ttggctcatc   6720
aggccagatt gagggtctgt ggacacatgt catgttagtg tacttcaatc gccccctgga   6780
tatagccccg acaataggcc gtggcctcat ttttttgcct tccgcacatt tccattgctc   6840
gatacccaca ccttgcttct cctgcacttg ccaaccttaa tactggttta cattgaccaa   6900
catcttacaa gcgggggggct tgtctagggt atatataaac agtggctctc ccaatcggtt   6960
gccagtctct ttttcctttt ctttccccac agattcgaaa tctaaactac acatcacaga   7020
attccgagcc gtgagtatcc acgacaagat cagtgtcgag acgacgcgtt ttgtgtaatg   7080
acacaatccg aaagtcgcta gcaacacaca ctctctacac aaactaaccc agctctggta   7140
ccatgggctc ctccaagacc gagatgatgg agcgatgcgc tatggccacc gtcgctcctt   7200
acgcacccgt tacctactgc cgaagagccc gagtcgacct ggacgattgt cttcccaaac   7260
cttacatgcc tcgagccctg tgtgctcctg accgagagca tccctacgga actcctggtc   7320
acaagaacta cggcctctcc gtgctgcagc agcatgtctc tttctttgac attgatgaca   7380
acggaatcat ttaccccctgg gagacctact ccggtctgcg gatgctcggc ttcaacatca   7440
```

```
ttggatctct gatcattgcc gctgtcatca accttacact cagctacgcc accctgcctg   7500
gttggcttcc ctctcccttc tttcccatct acattcacaa cattcataag tccaagcacg   7560
gctccgacag caagacttac gacaatgaag gacgattcat gcccgtcaac ctcgagctga   7620
tcttctcgaa gtacgccaag accctgcccg acaagctctc cttgggagag ctgtgggaga   7680
tgaccgaagg caaccgagat gcttgggaca tctttggatg gattgccggc aagatcgagt   7740
ggtgtctgct ctacctgctc gcttgcgacg aggaaggctt cttgtccaag gaggccattc   7800
gaagatgctt tgacggttct ctgttcgagt actgtgccaa gatctatgct ggtatcagcg   7860
agtgtaagac cgcatactat ggcgccggtc ccgctcgacc tgccggactt cctcccgcta   7920
cctactacga ctctctggcc gtcatgggat ccatgacaca acctgtgaat cggaaggcga   7980
ctgtcgagcg ggtcgagcca gcagtggagg tggctgactc cgagtccgag gccaagaccg   8040
acgtccacgt tcaccaccat catcaccacc acaagcgaaa atccgtcaag gcaagattc   8100 tcaacttctt cacccgaagt cgacgtatca ccttcgtcct cggagccgtg gtcggtgtga   8160
tagccgcggg atactacgct gcgccaccgg agctcagcat tgatatcgac gctcttctcg   8220
gcgacttgcc ctcgttcgac tttgacgctc tatctctcga caacttgtcg atggacagtg   8280
tgtcggactt tgtacaagac atgaaatcgc ggtttccgac caagattctg caggaggcgg   8340
ccaagatcga gaagcaccag aaaagcgaac agaaggctgc ccctttgct gtgggcaagg   8400 ctatgaagag cgagggactc aacgccaagt acccggtggt gctggtgccc ggcgtcatct   8460
ccacgggact ggagagctgg tccctggagg gaaccgagga gtgtcccacc gagtcgcact   8520
tcagaaagcg aatgtggggc tcctggtaca tgatccgagt catgctgctg acaagtact   8580 gctggctgca gaacctgatg ctggacacag agaccggtct agaccctccc catttcaagc   8640
tgcgagccgc ccagggattt gcctccgccg acttctttat ggcaggctac tggctgtgga   8700
acaagctgct cgagaacctg gctgttattg gatacgatac ggatacaatg tctgctgccg   8760
cgtacgactg gagactgtcc taccctgatt tggagcaccg agacggatac ttctccaagc   8820
tcaaagcttc aatcgaagag actaagcgta tgacaggtga agacagtt ctgacgggcc   8880 attctatggg ctcccaggtc atcttctact tcatgaagtg ggctgaggcc gagggatatg   8940
gaggaggagg tcccaactgg gtcaatgacc atattgaatc ctttgtcgac atttccggct   9000
ccatgctggg tactcccaag accctggttg ctcttctgtc tggagaaatg aaggataccg   9060
tgcagctgaa cgcgatggct gtgtatggac tggagcagtt cttctctcga cgagagcgag   9120
ccgatctgct gcgaacatgg ggaggaattg cttccatgat tcccaagggt ggtaaggcta   9180
tctggggtga tcattctgga gcccctgatg acgagcccgg ccagaatgtc acctttggca   9240
acttcatcaa gttcaaggag tccttgaccg agtactctgc taagaacctc actatggatg   9300
aaaccgttga cttcctgtat tctcagtctc ccgagtggtt tgtgaaccga accgagggtg   9360
cttactcctt tggaattgcc aagactcgaa agcaggttga gcagaatgag aagcgacctt   9420
ctacctggag caaccctctg aagctgctct ccccaatgc ccccgatctc aagatctact   9480
gcttctatgg agtcggtaag gataccgagc gagcctacta ctaccaggat gagcccaatc   9540
ccgagcagac caacttgaac gtcagtatcg ctggaaacga ccctgatggt gtgcttatgg   9600
gtcagggcga tggaaccgtc tcccttgtga cccataccat gtgtcaccga tggaaggacg   9660
agaactccaa gttcaaccct ggtaacgccc aggtcaaggt tgtggagatg ttgcaccagc   9720
ctgatcgact tgatattcga ggcggtgctc agactgccga gcatgtggac attctggggc   9780
```

-continued

| | |
|---|---|
| gttctgagtt gaacgagatg gttctgaagg tggctagtgg aaagggaaat gagattgaag | 9840 |
| agagagtcat ctccaacatt gatgagtggg tgtggaagat tgatctcggc agcaattagg | 9900 |
| c | 9901 |

<210> SEQ ID NO 63
<211> LENGTH: 9901
<212> TYPE: DNA
<213> ORGANISM: Artificial sequence
<220> FEATURE:
<223> OTHER INFORMATION: Construct pYRH97

<400> SEQUENCE: 63

| | |
|---|---|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt ttcacttgag tgcagtggct | 240 |
| agtgctctta ctcgtacagt gtgcaatact gcgtatcata gtctttgatg tatatcgtat | 300 |
| tcattcatgt tagttgcgta cgttgattga ggtggagcca gatgggctat tgtttcatat | 360 |
| atagactggc agccacctct ttggcccagc atgtttgtat acctggaagg gaaaactaaa | 420 |
| gaagctggct agtttagttt gattattata gtagatgtcc taatcactag agattagaat | 480 |
| gtcttggcga tgattagtcg tcgtcccctg tatcatgtct agaccaactg tgtcatgaag | 540 |
| ttggtgctgg tgttttacct gtgtactaca gtaggtgtc ctagatctag tgtacagagc | 600 |
| cgtttagacc catgtggact tcaccattaa cgatggaaaa tgttcattat atgacagtat | 660 |
| attacaatgg acttgctcca tttcttcctt gcatcacatg ttctccacct ccatagttga | 720 |
| tcaacacatc atagtagcta aggctgctgc tctcccacta cagtccacca caagttaagt | 780 |
| agcaccgtca gtacagctaa aagtacacgt ctagtacgtt tcataactag tcaagtagcc | 840 |
| cctattacag atatcagcac tatcacgcac gagttttttct ctgtgctatc taatcaactt | 900 |
| gccaagtatt cggagaagat acactttctt ggcatcaggt atacgaggga gcctatcaga | 960 |
| tgaaaaaggg tatattggat ccattcatat ccacctacac gttgtcataa tctcctcatt | 1020 |
| cacgtgattc atttcgtgac actagttttct cactttcccc cccgcaccta tagtcaactt | 1080 |
| ggcggacacg ctacttgtag ctgacgttga tttatagacc caatcaaagc gggttatcgg | 1140 |
| tcaggtagca cttatcattc atcgttcata ctacgatgag caatctcggg catgtccgga | 1200 |
| aaagtgtcgg gcgcgccagc tgcattaatg aatcggccaa cgcgcgggga gaggcggttt | 1260 |
| gcgtattggg cgctcttccg cttcctcgct cactgactcg ctgcgctcgg tcgttcggct | 1320 |
| gcggcgagcg gtatcagctc actcaaaggc ggtaatacgg ttatccacag aatcagggga | 1380 |
| taacgcagga aagaacatgt gagcaaaagg ccagcaaaag gccaggaacc gtaaaaaggc | 1440 |
| cgcgttgctg gcgttttttcc ataggctccg ccccccctgac gagcatcaca aaaatcgacg | 1500 |
| ctcaagtcag aggtggcgaa acccgacagg actataaaga taccaggcgt ttccccctgg | 1560 |
| aagctccctc gtgcgctctc ctgttccgac cctgccgctt accggatacc tgtccgcctt | 1620 |
| tctcccttcg ggaagcgtgg cgctttctca tagctcacgc tgtaggtatc tcagttcggt | 1680 |
| gtaggtcgtt cgctccaagc tgggctgtgt gcacgaaccc ccgttcagc ccgaccgctg | 1740 |
| cgccttatcc ggtaactatc gtcttgagtc caacccggta agacacgact tatcgccact | 1800 |
| ggcagcagcc actggtaaca ggattagcag agcgaggtat gtaggcggtg ctacagagtt | 1860 |
| cttgaagtgg tggcctaact acggctacac tagaagaaca gtatttggta tctgcgctct | 1920 |

```
gctgaagcca gttaccttcg gaaaaagagt tggtagctct tgatccggca aacaaaccac   1980
cgctggtagc ggtggttttt ttgtttgcaa gcagcagatt acgcgcagaa aaaaggatc   2040 tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
cggttcccaa cgatcaaggc gagttacatg atcccccatg ttgtgcaaaa aagcggttag   2640
ctccttcggt cctccgatcg ttgtcagaag taagttggcc gcagtgttat cactcatggt   2700
tatggcagca ctgcataatt ctcttactgt catgccatcc gtaagatgct tttctgtgac   2760
tggtgagtac tcaaccaagt cattctgaga atagtgtatg cggcgaccga gttgctcttg   2820
cccggcgtca atacgggata ataccgcgcc acatagcaga actttaaaag tgctcatcat   2880
tggaaaacgt tcttcggggc gaaaactctc aaggatctta ccgctgttga tccagttc   2940 gatgtaaccc actcgtgcac ccaactgatc ttcagcatct tttactttca ccagcgtttc   3000
tgggtgagca aaaacaggaa ggcaaaatgc cgcaaaaaag gaataagggc gacacggaa   3060 atgttgaata ctcatactct tcctttttca atattattga agcatttatc agggttattg   3120
tctcatgagc ggatacatat ttgaatgtat ttagaaaaat aaacaaatag gggttccgcg   3180
cacatttccc cgaaaagtgc cacctgatgc ggtgtgaaat accgcacaga tgcgtaagga   3240
gaaaataccg catcaggaaa ttgtaagcgt taatattttg ttaaaattcg cgttaaattt   3300
ttgttaaatc agctcatttt ttaaccaata ggccgaaatc ggcaaaatcc cttataaatc   3360
aaaagaatag accgagatag ggttgagtgt tgttccagtt tggaacaaga gtccactatt   3420
aaagaacgtg gactccaacg tcaaagggcg aaaaaccgtc tatcagggcg atggcccact   3480
acgtgaacca tcaccctaat caagttttt ggggtcgagg tgccgtaaag cactaaatcg   3540
gaaccctaaa gggagccccc gatttagagc ttgacgggga agccggcga acgtggcgag   3600 aaaggaaggg aagaaagcga aaggagcggg cgctagggcg ctggcaagtg tagcggtcac   3660
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
cagctggcga aggggatg tgctgcaagg cgattaagtt gggtaacgcc agggttttcc   3840
cagtcacgac gttgtaaaac gacggccagt gaattgtaat acgactcact ataggcgaa   3900 ttgggcccga cgtcgcatgc attccgacag cagcgactgg gcaccatgat caagcgaaac   3960
accttccccc agctgccctg gcaaaccatc aagaaccctc ctttcatcaa gtgcaagaac   4020
ggttctactc ttctcacctc cggtgtctac ggctggtgcc gaaagcctaa ctacaccgct   4080
gatttcatca tgtgcctcac ctgggctctc atgtgcggtg ttgcttctcc cctgccttac   4140
ttctacccgg tcttcttctt cctggtgctc atccaccgag cttaccgaga ctttgagcga   4200
ctggagcgaa agtacggtga ggactaccag gagttcaagc gacaggtccc ttggatcttc   4260
```

```
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100 cgtctcccctt gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580 cagtgccggc gtaggtgaag tcgtcaatga tgtcgatatg ggttttgatc atgcacacat    5640
aaggtccgac cttatcggca agtcaatga gctccttggt ggtggtaaca tccagagaag    5700
cacacaggtt ggttttcttg gctgccacga gcttgagcac tcgagcggca aaggcggact    5760
tgtggacgtt agctcgagct tcgtaggagg gcattttggt ggtgaagagg agactgaaat    5820
aaatttagtc tgcagaactt tttatcggaa ccttatctgg ggcagtgaag tatatgttat    5880
ggtaatagtt acgagttagt tgaacttata gatagactgg actatacggc tatcggtcca    5940
aattagaaag aacgtcaatg gctctctggg cgtcgccttt gccgacaaaa atgtgatcat    6000
gatgaaagcc agcaatgacg ttgcagctga tattgttgtc ggccaaccgc gccgaaaacg    6060
cagctgtcag acccacagcc tccaacgaag aatgtatcgt caaagtgatc caagcacact    6120
catagttgga gtcgtactcc aaaggcggca atgacgagtc agacagatac tcgtcgacgt    6180
ttaaacagtg tacgcagatc tactatagag gaacatttaa attgccccgg agaagacggc    6240
caggccgcct agatgacaaa ttcaacaact cacagctgac tttctgccat tgccactagg    6300
ggggggcctt tttatatggc caagccaagc tctccacgtc ggttgggctg cacccaacaa    6360 taaatggta gggttgcacc aacaaaggga tgggatgggg ggtagaagat acgaggataa    6420
cggggctcaa tggcacaaat aagaacgaat actgccatta agactcgtga tccagcgact    6480
gacaccattg catcatctaa gggcctcaaa actacctcgg aactgctgcg ctgatctgga    6540
caccacagag gttccgagca ctttaggttg caccaaatgt cccaccaggt gcaggcagaa    6600
aacgctggaa cagcgtgtac agtttgtctt aacaaaaagt gagggcgctg aggtcgagca    6660
```

```
gggtggtgtg acttgttata gcctttagag ctgcgaaagc gcgtatggat ttggctcatc    6720
aggccagatt gagggtctgt ggacacatgt catgttagtg tacttcaatc gcccctgga    6780 tatagccccg acaataggcc gtggcctcat ttttttgcct tccgcacatt tccattgctc    6840
gatacccaca ccttgcttct cctgcacttg ccaaccttaa tactggttta cattgaccaa    6900
catcttacaa gcgggggct tgtctagggt atatataaac agtggctctc ccaatcggtt     6960
gccagtctct ttttccttt ctttccccac agattcgaaa tctaaactac acatcacaga    7020
attccgagcc gtgagtatcc acgacaagat cagtgtcgag acgacgcgtt ttgtgtaatg    7080
acacaatccg aaagtcgcta gcaacacaca ctctctacac aaactaaccc agctctggta    7140
ccatggccac acaacctgtg aatcggaagg cgactgtcga gcgggtcgag ccagcagtgg    7200
aggtggctga ctccgagtcc gaggccaaga ccgacgtcca cgttcaccac catcatcacc    7260
accacaagcg aaaatccgtc aagggcaaga ttctcaactt cttcacccga gtcgacgta    7320 tcaccttcgt cctcggagcc gtggtcggtg tgatagccgc gggatactac gctgcgccac    7380
cggagctcag cattgatatc gacgctcttc tcggcgactt gccctcgttc gactttgacg    7440
ctctatctct cgacaacttg tcgatggaca gtgtgtcgga cttgtacaa gacatgaaat     7500 cgcggtttcc gaccaagatt ctgcaggagg cggccaagat cgagaagcac cagaaaagcg    7560
aacagaaggc tgcccctttt gctgtgggca aggctatgaa gagcgaggga ctcaacgcca    7620
agtaccccgt ggtgctggtg cccggcgtca tctccacggg actggagagc tggtccctgg    7680
agggaaccga ggagtgtccc accgagtcgc acttcagaaa gcgaatgtgg ggctcctggt    7740
acatgatccg agtcatgctg ctggacaagt actgctggct gcagaacctg atgctggaca    7800
cagagaccga tctagaccct ccccatttca agctgcgagc cgcccaggga tttgcctccg    7860
ccgacttctt tatggcaggc tactggctgt ggaacaagct gctcgagaac ctggctgtta    7920
ttggatacga tacggataca atgtctgctc ccgcgtacga ctggagactg tcctaccctg    7980
atttggagca ccgagacgga tacttctcca agctcaaagc ttcaatcgaa gagactaagc    8040
gtatgacagg tgagaagaca gttctgacgg gccattctat gggctcccag gtcatcttct    8100
acttcatgaa gtgggctgag gccgagggat atggaggagg aggtcccaac tgggtcaatg    8160
accatattga atcctttgtc gacatttccg gctccatgct gggtactccc aagaccctgg    8220
ttgctcttct gtctggagaa atgaaggata ccgtgcagct gaacgcgatg gctgtgtatg    8280
gactggagca gttcttctct cgacgagagc gagccgatct gctgcgaaca tggggaggaa    8340
ttgcttccat gattcccaag ggtggtaagg ctatctgggg tgatcattct ggagcccctg    8400
atgacgagcc cggccagaat gtcacctttg gcaacttcat caagttcaag gagtccttga    8460
ccgagtactc tgctaagaac ctcactatgg atgaaaccgt tgacttcctg tattctcagt    8520 ctccccgagtg gtttgtgaac cgaaccgagg gtgcttactc ctttggaatt gccaagactc    8580
gaaagcaggt tgagcagaat gagaagcgac cttctacctg gagcaacccct ctggaagctg    8640 ctctccccaa tgcccccgat ctcaagatct actgcttcta tggagtcggt aaggataccg    8700
agcgagccta ctactaccag gatgagccca atcccgagca gaccaacttg aacgtcagta    8760
tcgctggaaa cgaccctgat ggtgtgctta tgggtcaggg cgatggaacc gtctcccttg    8820
tgacccatac catgtgtcac cgatggaagg acgagaactc caagttcaac cctggtaacg    8880
cccaggtcaa ggttgtggag atgttgcacc agcctgatcg acttgatatt cgaggcggtt    8940
ctcagactgc cgagcatgtg gacattctgg ggcgttctga gttgaacgag atggttctga    9000
```

| | |
|---|---:|
| aggtggctag tggaaaggga atgagattg aagagagagt catctccaac attgatgagt | 9060 |
| gggtgtggaa gattgatctc ggcagcaatg gcgccggtcc cgctcgacct gccggacttc | 9120 |
| ctcccgctac ctactacgac tctctggccg tcatgggatc catgtgctcc aagaccgaga | 9180 |
| tgatggagcg atgcgctatg gccaccgtcg ctccttacgc acccgttacc tactgccgaa | 9240 |
| gagcccgagt cgacctggac gattgtcttc ccaaaccttc atgcctcga gccctgtgtg | 9300 |
| ctcctgaccg agagcatccc tacggaactc ctggtcacaa gaactacggc ctctccgtgc | 9360 |
| tgcagcagca tgtctctttc tttgacattg atgacaacgg aatcatttac ccctgggaga | 9420 |
| cctactccgg tctgcggatg ctcggcttca acatcattgg atctctgatc attgccgctg | 9480 |
| tcatcaacct tacactcagc tacgccaccc tgcctggttg gcttccctct cccttctttc | 9540 |
| ccatctacat tcacaacatt cataagtcca agcacggctc cgacagcaag acttacgaca | 9600 |
| atgaaggacg attcatgccc gtcaacctcg agctgatctt ctcgaagtac gccaagaccc | 9660 |
| tgcccgacaa gctctccttg ggagagctgt gggagatgac cgaaggcaac cgagatgctt | 9720 |
| gggacatctt tggatggatt gccggcaaga tcgagtggtg tctgctctac ctgctcgctt | 9780 |
| gcgacgagga aggcttcttg tccaaggagg ccattcgaag atgctttgac ggttctctgt | 9840 |
| tcgagtactg tgccaagatc tatgctggta tcagcgagtg taagaccgca tactattaag | 9900 |
| c | 9901 |

<210> SEQ ID NO 64
<211> LENGTH: 9490
<212> TYPE: DNA
<213> ORGANISM: Artificial sequence
<220> FEATURE:
<223> OTHER INFORMATION: Construct pYRH98

<400> SEQUENCE: 64

| | |
|---|---:|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt tcacttgag tgcagtggct | 240 |
| agtgctctta ctcgtacagt gtgcaatact gcgtatcata gtctttgatg tatatcgtat | 300 |
| tcattcatgt tagttgcgta cgttgattga ggtggagcca gatgggctat tgtttcatat | 360 |
| atagactggc agccacctct ttggcccagc atgtttgtat acctggaagg gaaaactaaa | 420 |
| gaagctggct agtttagttt gattattata gtagatgtcc taatcactag agattagaat | 480 |
| gtcttggcga tgattagtcg tcgtcccctg tatcatgtct agaccaactg tgtcatgaag | 540 |
| ttggtgctgg tgttttacct gtgtactaca agtaggtgtc ctagatctag tgtacagagc | 600 |
| cgtttagacc catgtggact tcaccattaa cgatggaaaa tgttcattat atgacagtat | 660 |
| attacaatgg acttgctcca tttcttcctt gcatcacatg ttctccacct ccatagttga | 720 |
| tcaacacatc atagtagcta aggctgctgc tctcccacta cagtccacca caagttaagt | 780 |
| agcaccgtca gtacagctaa aagtacacgt ctagtacgtt tcataactag tcaagtagcc | 840 |
| cctattacag atatcagcac tatcacgcac gagttttttct ctgtgctatc taatcaactt | 900 |
| gccaagtatt cggagaagat acactttctt ggcatcaggt atacgaggga gcctatcaga | 960 |
| tgaaaaaggg tatattggat ccattcatat ccacctacac gttgtcataa tctcctcatt | 1020 |
| cacgtgattc atttcgtgac actagtttct cactttcccc cccgcaccta tagtcaactt | 1080 |
| ggcggacacg ctacttgtag ctgacgttga tttatagacc caatcaaagc gggttatcgg | 1140 |

```
tcaggtagca cttatcattc atcgttcata ctacgatgag caatctcggg catgtccgga    1200
aaagtgtcgg gcgcgccagc tgcattaatg aatcggccaa cgcgcgggga gaggcggttt    1260
gcgtattggg cgctcttccg cttcctcgct cactgactcg ctgcgctcgg tcgttcggct    1320
gcggcgagcg gtatcagctc actcaaaggc ggtaatacgg ttatccacag aatcagggga    1380
taacgcagga agaacatgt gagcaaaagg ccagcaaaag gccaggaacc gtaaaaaggc    1440
cgcgttgctg gcgtttttcc ataggctccg ccccctgac gagcatcaca aaaatcgacg    1500
ctcaagtcag aggtggcgaa acccgacagg actataaaga taccaggcgt ttccccctgg    1560
aagctccctc gtgcgctctc ctgttccgac cctgccgctt accggatacc tgtccgcctt    1620
tctcccttcg ggaagcgtgg cgctttctca tagctcacgc tgtaggtatc tcagttcggt    1680
gtaggtcgtt cgctccaagc tgggctgtgt gcacgaaccc cccgttcagc ccgaccgctg    1740
cgccttatcc ggtaactatc gtcttgagtc caacccggta agacacgact tatcgccact    1800
ggcagcagcc actggtaaca ggattagcag agcgaggtat gtaggcggtg ctacagagtt    1860
cttgaagtgg tggcctaact acggctacac tagaagaaca gtatttggta tctgcgctct    1920
gctgaagcca gttaccttcg gaaaaagagt tggtagctct tgatccggca aacaaaccac    1980
cgctggtagc ggtggttttt ttgtttgcaa gcagcagatt acgcgcagaa aaaaggatc    2040 tcaagaagat cctttgatct tttctacggg gtctgacgct cagtggaacg aaaactcacg    2100
ttaagggatt ttggtcatga gattatcaaa aaggatcttc acctagatcc ttttaaatta    2160
aaaatgaagt tttaaatcaa tctaaagtat atatgagtaa acttggtctg acagttacca    2220
atgcttaatc agtgaggcac ctatctcagc gatctgtcta tttcgttcat ccatagttgc    2280
ctgactcccc gtcgtgtaga taactacgat acgggagggc ttaccatctg gccccagtgc    2340
tgcaatgata ccgcgagacc cacgctcacc ggctccagat ttatcagcaa taaaccagcc    2400
agccggaagg gccgagcgca gaagtggtcc tgcaacttta tccgcctcca tccagtctat    2460
taattgttgc cgggaagcta gagtaagtag ttcgccagtt aatagtttgc gcaacgttgt    2520
tgccattgct acaggcatcg tggtgtcacg ctcgtcgttt ggtatggctt cattcagctc    2580
cggttcccaa cgatcaaggc gagttacatg atcccccatg ttgtgcaaaa aagcggttag    2640
ctccttcggt cctccgatcg ttgtcagaag taagttggcc gcagtgttat cactcatggt    2700
tatggcagca ctgcataatt ctcttactgt catgccatcc gtaagatgct tttctgtgac    2760
tggtgagtac tcaaccaagt cattctgaga atagtgtatg cggcgaccga gttgctcttg    2820
cccggcgtca atacgggata ataccgcgcc acatagcaga actttaaaag tgctcatcat    2880
tggaaaacgt tcttcgggc gaaaactctc aaggatctta ccgctgttga tccagttc    2940 gatgtaaccc actcgtgcac ccaactgatc ttcagcatct tttactttca ccagcgtttc    3000
tgggtgagca aaaacaggaa ggcaaaatgc cgcaaaaaag ggaataaggg cgacacggaa    3060
atgttgaata ctcatactct tccttttca atattattga agcatttatc agggttattg    3120
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
```

```
acgtgaacca tcaccctaat caagttttt  ggggtcgagg tgccgtaaag cactaaatcg    3540
gaaccctaaa gggagccccc gatttagagc ttgacgggga aagccggcga acgtggcgag    3600
aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aggggggatg tgctgcaagg cgattaagtt gggtaacgcc agggttttcc    3840
cagtcacgac gttgtaaaac gacggccagt gaattgtaat acgactcact atagggcgaa    3900
ttgggcccga cgtcgcatgc attccgacag cagcgactgg gcaccatgat caagcgaaac    3960
accttccccc agctgccctg gcaaaccatc aagaaccta  ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagaccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccaccccgg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
actttctgtc ctcgaacagg aagaaaccgt gcttaagagc aagttccttg aggggagca    5580
cagtgccggc gtaggtgaag tcgtcaatga tgtcgatatg gttttgatc  atgcacacat    5640
aaggtccgac cttatcggca agctcaatga gctccttggt ggtggtaaca tccagagaag    5700
cacacaggtt ggttttcttg gctgccacga gcttgagcac tcgagcggca aggcggact    5760
tgtgacgtt  agctcgagct tcgtaggagg gcatttggt  ggtgaagagg agactgaaat    5820
aaatttagtc tgcagaactt tttatcggaa ccttatctgg ggcagtgaag tatatgttat    5880
```

```
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
cagctgtcag acccacagcc tccaacgaag aatgtatcgt caaagtgatc caagcacact   6120
catagttgga gtcgtactcc aaaggcggca atgacgagtc agacagatac tcgtcgacgt   6180
ttaaacagtg tacgcagatc tactatagag gaacatttaa attgcccgg agaagacggc   6240
caggccgcct agatgacaaa ttcaacaact cacagctgac tttctgccat tgccactagg   6300
gggggggcctt tttatatggc caagccaagc tctccacgtc ggttgggctg cacccaacaa   6360
taaatgggta gggttgcacc aacaaaggga tgggatgggg ggtagaagat acgaggataa   6420
cggggctcaa tggcacaaat aagaacgaat actgccatta agactcgtga tccagcgact   6480
gacaccattg catcatctaa gggcctcaaa actacctcgg aactgctgcg ctgatctgga   6540
caccacagag gttccgagca ctttaggttg caccaaatgt cccaccaggt gcaggcagaa   6600
aacgctggaa cagcgtgtac agtttgtctt aacaaaaagt gagggcgctg aggtcgagca   6660
gggtggtgtg acttgttata gcctttagag ctgcgaaagc gcgtatggat ttggctcatc   6720
aggccagatt gagggtctgt ggacacatgt catgttagtg tacttcaatc gcccctgga   6780
tatagccccg acaataggcc gtggcctcat ttttttgcct tccgcacatt tccattgctc   6840
gatacccaca ccttgcttct cctgcacttg ccaaccttaa tactggttta cattgaccaa   6900
catcttacaa gcggggggct tgtctagggt atatataaac agtggctctc ccaatcggtt   6960
gccagtctct ttttccttt ctttccccac agattcgaaa tctaaactac acatcacaga   7020
attccgagcc gtgagtatcc acgacaagat cagtgtcgag acgacgcgtt ttgtgtaatg   7080
acacaatccg aaagtcgcta gcaacacaca ctctctacac aaactaaccc agctctggta   7140
ccatgggctg ctccaagacc gagatgatgg agcgatgcgc tatggccacc gtcgctcctt   7200
acgcacccgt tacctactgc cgaagagccc gagtcgacct ggacgattgt cttcccaaac   7260
cttacatgcc tcgagccctg tgtgctcctg accgagagca tccctacgga actcctggtc   7320
acaagaacta cggcctctcc gtgctgcagc agcatgtctc tttctttgac attgatgaca   7380
acggaatcat ttacccctgg gagacctact ccggtctgcg gatgctcggc ttcaacatca   7440
ttggatctct gatcattgcc gctgtcatca accttacact cagctacgcc accctgcctg   7500
gttggcttcc ctctccctt ttcccatct acattcacaa cattcataag tccaagcacg   7560
gctccgacag caagacttac gacaatgaag gacgattcat gcccgtcaac ctcgagctga   7620
tcttctcgaa gtacgccaag accctgcccg acaagctctc cttgggagag ctgtgggaga   7680
tgaccgaagg caaccgagat gcttgggaca tctttggatg gattgccggc aagatcgagt   7740
ggtgtctgct ctacctgctc gcttgcgacg aggaaggctt cttgtccaag gaggccattc   7800
gaagatgctt tgacggttct ctgttcgagt actgtgccaa gatctatgct ggtatcagcg   7860
agtgtaagac cgcatactat ggcgccggtc ccgctcgacc tgccggactt cctcccgcta   7920
cctactacga ctctctggcc gtcatgggat ccgccttccc ctgggctgac aagtgggctg   7980
ccgacgcttc cgcttctacc ggactgcctc ccgatctgct caagattgcc ttcaccctgg   8040
ttatgtcgta ccctctctct tccctgatga agcgacttcc cgacgatgcc aagaacctga   8100
agatcattta catcatttcc gtgtctatct tctacatggt cggtgtgttt tcgctgtacg   8160
gcggagccgc tactctgctc ttctcctcta tgggcacctt ctttatcact cagtggaagt   8220
```

```
ctccctacat gccttgggtc aacttcggat ttgttatgac tcacctcttc gtcaaccacc    8280
tgcgatccca gttctttccc gagacctacg accctaacgt catcgacatt actggtgctc    8340
agatggttct ctgtatgaag ctgtcctcgt tcggctggaa cgtctacgac ggatggcaga    8400
tcgagaaggg cgaacaactt tccgagttcc agaccaagcg agccgtgctc aagcatccct    8460
ctctcatgga ctttctggcc ttcgtctttt actttccctc cattctcact ggtccttcct    8520
acgactacat ggagtttcac aactggctgg atctttctct cttcaaggaa ctggagaaag    8580
acaaggatcc caagcgagcc gctcgacgga agcgacacaa gattcctcga tctggcatcg    8640
cagcttcgaa aaagctcgct gccggaatct tctggattgt gctgtggacc caggtcgact    8700
ctcgaatttc cactgcctat gcttactcgg atgccttcac caaggagcac aacatcttcg    8760
gacgaattgt ctatttgtac atgctgggct tcatgtaccg actcaagtac tatggtgctt    8820
ggtccatctc ggaaggagcc tgcattctct ccggtctggg ctttcatggt gttgatccca    8880
agaccggaaa gtacaagtgg gaccgagttc agaacgtcga tccttggggc ttcgagaccg    8940
gtcagaacac caaggctctg ctcgaggcct ggaaccagaa caccaacaag tggcttcgaa    9000
actacgtcta tctgcgagtg gtccccaagg ccagaagcc tggatttcga gctaccatct    9060
tcacttttgt cgtgtctgcc ttctggcacg gtacccgacc cggctactat ctcacctttg    9120
ttacagccgc tatgtaccag agcgtcggca agttctttag acgatacctg cgaccttct    9180 ttatggagtc cgacggaaag accgcaggtc cttacaagat ctattacgac attgtctgtt    9240
ggatcgtggt tcaaaccgct ttcggctacg ccactcagtc cttcatgatt ctcgacttct    9300
ggctgtctct caagtgctgg aagaactcgt ggtttctcta ccatatcgcc ttgggagcta    9360 tcttttgccat ttcctctccc tacaaggcct gggctatccc taagatcaag aaaaagcagg    9420
ccggtgctgt taccgacaaa aaggatgcca aggaggaggt caaaaaggac actatcaaaa    9480
ccaagtaagc                                                           9490
```

<210> SEQ ID NO 65
<211> LENGTH: 9490
<212> TYPE: DNA
<213> ORGANISM: Artificial sequence
<220> FEATURE:
<223> OTHER INFORMATION: Construct pYRH99

<400> SEQUENCE: 65

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgttgattga ggtggagcca gatgggctat tgtttcatat     360
atagactggc agccacctct ttggcccagc atgtttgtat acctggaagg gaaaactaaa     420
gaagctggct agtttagttt gattattata gtagatgtcc taatcactag agattagaat     480
gtcttggcga tgattagtcg tcgtcccctg tatcatgtct agaccaactg tgtcatgaag     540
ttggtgctgg tgttttacct gtgtactaca agtaggtgtc ctagatctag tgtacagagc     600
cgtttagacc catgtggact tcaccattaa cgatggaaaa tgttcattat atgacagtat     660
attacaatgg acttgctcca tttcttcctt gcatcacatg ttctccacct ccatagttga     720
tcaacacatc atagtagcta aggctgctgc tctcccacta cagtccacca caagttaagt     780
```

```
agcaccgtca gtacagctaa aagtacacgt ctagtacgtt tcataactag tcaagtagcc    840
cctattacag atatcagcac tatcacgcac gagttttct ctgtgctatc taatcaactt    900
gccaagtatt cggagaagat acactttctt ggcatcaggt atacgaggga gcctatcaga    960
tgaaaaaggg tatattggat ccattcatat ccacctacac gttgtcataa tctcctcatt   1020
cacgtgattc atttcgtgac actagttttct cactttcccc cccgcaccta tagtcaactt   1080
ggcggacacg ctacttgtag ctgacgttga tttatagacc caatcaaagc gggttatcgg   1140
tcaggtagca cttatcattc atcgttcata ctacgatgag caatctcggg catgtccgga   1200
aaagtgtcgg gcgcgccagc tgcattaatg aatcggccaa cgcgcgggga gaggcggttt   1260
gcgtattggg cgctcttccg cttcctcgct cactgactcg ctgcgctcgg tcgttcggct   1320
gcggcgagcg gtatcagctc actcaaaggc ggtaatacgg ttatccacag aatcagggga   1380
taacgcagga agaacatgt gagcaaaagg ccagcaaaag gccaggaacc gtaaaaaggc   1440
cgcgttgctg gcgtttttcc ataggctccg ccccctgac gagcatcaca aaatcgacg   1500 ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgctttctca gctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca aacaaaccac   1980
cgctggtagc ggtggttttt tgtttgcaa gcagcagatt acgcgcagaa aaaaggatc   2040 tcaagaagat cctttgatct ttctacgg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
cggttcccaa cgatcaaggc gagttacatg atcccccatg ttgtgcaaaa aagcggttag   2640
ctccttcggt cctccgatcg ttgtcagaag taagttggcc gcagtgttat cactcatggt   2700
tatggcagca ctgcataatt ctcttactgt catgccatcc gtaagatgct tttctgtgac   2760
tggtgagtac tcaaccaagt cattctgaga atagtgtatg cggcgaccga gttgctcttg   2820
cccggcgtca atacgggata ataccgcgcc acatagcaga actttaaaag tgctcatcat   2880
tggaaaacgt tcttcggggc gaaaactctc aaggatctta ccgctgttga tccagttc   2940 gatgtaaccc actcgtgcac ccaactgatc ttcagcatct tttactttca ccagcgtttc   3000
tgggtgagca aaaacaggaa ggcaaaatgc cgcaaaaaag gaataagggc gacacggaa   3060 atgttgaata ctcatactct tcctttttca atattattga agcatttatc agggttattg   3120
```

```
tctcatgagc ggatacatat ttgaatgtat ttagaaaaat aaacaaatag gggttccgcg    3180
cacatttccc cgaaaagtgc cacctgatgc ggtgtgaaat accgcacaga tgcgtaagga    3240
gaaaataccg catcaggaaa ttgtaagcgt taatattttg ttaaaattcg cgttaaattt    3300
ttgttaaatc agctcatttt ttaaccaata ggccgaaatc ggcaaaatcc cttataaatc    3360
aaaagaatag accgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcaccctaat caagtttttt ggggtcgagg tgccgtaaag cactaaatcg    3540
gaaccctaaa gggagccccc gatttagagc ttgacgggga agccggcga acgtggcgag    3600 aaaggaaggg aagaaagcga aaggagcggg cgctagggcg ctggcaagtg tagcggtcac    3660
gctgcgcgta accaccacac ccgccgcgct taatgcgccg ctacagggcg cgtccattcg    3720
ccattcaggc tgcgcaactg ttgggaaggg cgatcggtgc gggcctcttc gctattacgc    3780
cagctggcga aagggggatg tgctgcaagg cgattaagtt gggtaacgcc agggttttcc    3840
cagtcacgac gttgtaaaac gacggccagt gaattgtaat acgactcact ataggggcgaa    3900 ttgggcccga cgtcgcatgc attccgacag cagcgactgg gcaccatgat caagcgaaac    3960
accttccccc agctgccctg gcaaaccatc aagaaccta ctttcatcaa gtgcaagaac    4020
ggttctactc ttctcacctc cggtgtctac ggctggtgcc gaaagcctaa ctacaccgct    4080
gatttcatca tgtgcctcac ctgggctctc atgtgcggtg ttgcttctcc cctgccttac    4140
ttctacccgg tcttcttctt cctggtgctc atccaccgag cttaccgaga ctttgagcga    4200
ctggagcgaa agtacggtga ggactaccag gagttcaagc gacaggtccc ttggatcttc    4260
atcccttatg ttttctaaac gataagctta gtgagcgaat ggtgaggtta cttaattgag    4320
tggccagcct atgggattgt ataacagaca gtcaatatat tactgaaaag actgaacagc    4380
cagacggagt gaggttgtga gtgaatcgta gagggcggct attacagcaa gtctactcta    4440
cagtgtacta acacagcaga gaacaaatac aggtgtgcat tcggctatct gagaattagt    4500
tggagagctc gagacccctcg gcgataaact gctcctcggt tttgtgtcca tacttgtacg    4560
gaccattgta atggggcaag tcgttgagtt ctcgtcgtcc gacgttcaga gcacagaaac    4620
caatgtaatc aatgtagcag agatggttct gcaaagatt gatttgtgcg agcaggttaa    4680
ttaagtcata cacaagtcag ctttcttcga gcctcatata agtataagta gttcaacgta    4740
ttagcactgt acccagcatc tccgtatcga gaaacacaac aacatgcccc attggacaga    4800
tcatgcggat acacaggttg tgcagtatca tacatactcg atcagacagg tcgtctgacc    4860
atcatacaag ctgaacaagc gctccatact tgcacgctct ctatatacac agttaaatta    4920
catatccata gtctaacctc taacagttaa tcttctggta agcctcccag ccagccttct    4980
ggtatcgctt ggcctcctca ataggatctc ggttctggcc gtacagacct cggccgacaa    5040
ttatgatatc cgttccggta gacatgacat cctcaacagt tcggtactgc tgtccgagag    5100
cgtctccctt gtcgtcaaga cccacccggg gggtcagaat aagccagtcc tcagagtcgc    5160
ccttaggtcg gttctgggca atgaagccaa ccacaaactc ggggtcggat cgggcaagct    5220
caatggtctg cttggagtac tcgccagtgg ccagagagcc cttgcaagac agctcggcca    5280
gcatgagcag acctctggcc agcttctcgt tgggagaggg gactaggaac tccttgtact    5340
gggagttctc gtagtcagag acgtcctcct tcttctgttc agagacagtt tcctcggcac    5400
cagctcgcag gccagcaatg attccggttc cgggtacacc gtgggcgttg gtgatatcgg    5460
accactcggc gattcggtga caccggtact ggtgcttgac agtgttgcca atatctgcga    5520
```

```
actttctgtc ctcgaacagg aagaaaccgt gcttaagagc aagttccttg aggggggagca   5580 cagtgccggc gtaggtgaag tcgtcaatga tgtcgatatg ggttttgatc atgcacacat   5640
aaggtccgac cttatcggca agctcaatga gctccttggt ggtggtaaca tccagagaag   5700
cacacaggtt ggttttcttg gctgccacga gcttgagcac tcgagcggca aaggcggact   5760
tgtggacgtt agctcgagct tcgtaggagg gcattttggt ggtgaagagg agactgaaat   5820
aaatttagtc tgcagaactt tttatcggaa ccttatctgg ggcagtgaag tatatgttat   5880
ggtaatagtt acgagttagt tgaacttata gatagactgg actatacggc tatcggtcca   5940
aattagaaag aacgtcaatg gctctctggg cgtcgccttt gccgacaaaa atgtgatcat   6000
gatgaaagcc agcaatgacg ttgcagctga tattgttgtc ggccaaccgc gccgaaaacg   6060
cagctgtcag acccacagcc tccaacgaag aatgtatcgt caaagtgatc caagcacact   6120
catagttgga gtcgtactcc aaaggcggca atgacgagtc agacagatac tcgtcgacgt   6180
ttaaacagtg tacgcagatc tactatagag gaacatttaa attgcccgg agaagacggc   6240 caggccgcct agatgacaaa ttcaacaact cacagctgac tttctgccat tgccactagg   6300
ggggggcctt tttatatggc caagccaagc tctccacgtc ggttgggctg cacccaacaa   6360
taaatgggta gggttgcacc aacaaaggga tgggatgggg ggtagaagat acgaggataa   6420
cggggctcaa tggcacaaat aagaacgaat actgccatta agactcgtga tccagcgact   6480
gacaccattg catcatctaa gggcctcaaa actacctcgg aactgctgcg ctgatctgga   6540
caccacagag gttccgagca ctttaggttg caccaaatgt cccaccaggt gcaggcagaa   6600
aacgctggaa cagcgtgtac agtttgtctt aacaaaaagt gagggcgctg aggtcgagca   6660
gggtggtgtg acttgttata gcctttagag ctgcgaaagc gcgtatggat ttggctcatc   6720
aggccagatt gagggtctgt ggacacatgt catgttagtg tacttcaatc gccccctgga   6780
tatagccccg acaataggcc gtggcctcat ttttttgcct tccgcacatt tccattgctc   6840
gatacccaca ccttgcttct cctgcacttg ccaaccttaa tactggttta cattgaccaa   6900
catcttacaa gcgggggggct tgtctagggt atatataaac agtggctctc ccaatcggtt   6960
gccagtctct ttttccttt ctttccccac agattcgaaa tctaaactac acatcacaga   7020
attccgagcc gtgagtatcc acgacaagat cagtgtcgag acgacgcgtt ttgtgtaatg   7080
acacaatccg aaagtcgcta gcaacacaca ctctctacac aaactaaccc agctctggta   7140
ccatggcctt cccctgggct gacaagtggg ctgccgacgc ttccgcttct accggactgc   7200
ctcccgatct gctcaagatt gccttcaccc tggttatgtc gtaccctctc tcttccctga   7260
tgaagcgact tcccgacgat gccaagaacc tgaagatcat ttacatcatt tccgtgtcta   7320
tcttctacat ggtcggtgtg ttttcgctgt acggcggagc cgctactctg ctcttctcct   7380
ctatgggcac cttctttatc actcagtgga agtctcccta catgccttgg gtcaacttcg   7440
gatttgttat gactcaccte ttcgtcaacc acctgcgatc ccagttcttt cccgagacct   7500
acgaccctaa cgtcatcgac attactggtg ctcagatggt tctctgtatg aagctgtcct   7560
cgttcggctg gaacgtctac gacggatggc agatcgagaa gggcgaacaa ctttccgagt   7620
tccagaccaa gcgagccgtg ctcaagcatc cctctctcat ggactttctg gccttcgtct   7680
tttactttcc ctccattctc actggtcctt cctacgacta catggagttt cacaactggc   7740
tggatctttc tctcttcaag gaactggaga aagacaagga tcccaagcga gccgctcgac   7800
ggaagcgaca caagattcct cgatctggca tcgcagcttc gaaaaagctc gctgccggaa   7860
```

```
tcttctggat tgtgctgtgg acccaggtcg actctcgaat ttccactgcc tatgcttact    7920
cggatgcctt caccaaggag cacaacatct tcggacgaat tgtctatttg tacatgctgg    7980
gcttcatgta ccgactcaag tactatggtg cttggtccat ctcggaagga gcctgcattc    8040
tctccggtct gggctttcat ggtgttgatc ccaagaccgg aaagtacaag tgggaccgag    8100
ttcagaacgt cgatccttgg ggcttcgaga ccggtcagaa caccaaggct ctgctcgagg    8160
cctggaacca gaacaccaac aagtggcttc gaaactacgt ctatctgcga gtggtcccca    8220
agggccagaa gcctggattt cgagctacca tcttcacttt tgtcgtgtct gccttctggc    8280
acggtacccg acccggctac tatctcacct ttgttacagc cgctatgtac cagagcgtcg    8340
gcaagttctt tagacgatac ctgcgaccct tctttatgga gtccgacgga aagaccgcag    8400
gtccttacaa gatctattac gacattgtct gttggatcgt ggttcaaacc gctttcggct    8460
acgccactca gtccttcatg attctcgact tctggctgtc tctcaagtgc tggaagaact    8520
cgtggtttct ctaccatatc gccttgggag ctatctttgc catttcctct ccctacaagg    8580
cctgggctat ccctaagatc aagaaaaagc aggccggtgc tgttaccgac aaaaaggatg    8640
ccaaggagga ggtcaaaaag gacactatca aaaccaaggg cgccggtccc gctcgacctg    8700
ccggacttcc tcccgctacc tactacgact ctctggccgt catgggatcc atgtgctcca    8760
agaccgagat gatggagcga tgcgctatgg ccaccgtcgc tccttacgca cccgttacct    8820
actgccgaag agcccgagtc gacctggacg attgtcttcc caaaccttac atgcctcgag    8880
ccctgtgtgc tcctgaccga gagcatccct acggaactcc tggtcacaag aactacggcc    8940
tctccgtgct gcagcagcat gtctctttct ttgacattga tgacaacgga atcatttacc    9000
cctgggagac ctactccggt ctgcggatgc tcggcttcaa catcattgga tctctgatca    9060
ttgccgctgt catcaacctt acactcagct acgccaccct gcctggttgg cttccctctc    9120
ccttctttcc catctacatt cacaacattc ataagtccaa gcacggctcc gacagcaaga    9180
cttacgacaa tgaaggacga ttcatgcccg tcaacctcga gctgatcttc tcgaagtacg    9240
ccaagaccct gcccgacaag ctctccttgg gagagctgtg ggagatgacc gaaggcaacc    9300
gagatgcttg ggacatcttt ggatggattg ccggcaagat cgagtggtgt ctgctctacc    9360
tgctcgcttg cgacgaggaa ggcttcttgt ccaaggaggc cattcgaaga tgctttgacg    9420
gttctctgtt cgagtactgt gccaagatct atgctggtat cagcgagtgt aagaccgcat    9480
actattaagc                                                           9490
```

EXPRESSION OF CALEOSIN IN RECOMBINANT OLEAGINOUS MICROORGANISMS TO INCREASE OIL CONTENT THEREIN

This application claims the benefit of U.S. Provisional Application No. 61/490,337, filed May 26, 2011, which is incorporated herein by reference in its entirety.

FIELD OF THE INVENTION

This invention is in the field of biotechnology. More specifically, this invention pertains to recombinant oleaginous microorganisms that are capable of producing more oil due to the expression of a caleosin polypeptide.

BACKGROUND OF THE INVENTION

Microorganisms such as filamentous fungi, yeast and algae produce a variety of lipids, including fatty acyls, glycerolipids, phospholipids, sphingolipids, saccharolipids, polyketides, sterol lipids and prenol lipids. One class of lipids commonly extracted from microbes is glycerolipids, including the fatty acid esters of glycerol ("triacylglycerols" or "TAGs"). TAGs are the primary storage unit for fatty acids, and thus may contain long chain polyunsaturated fatty acids (PUFAs), as well as shorter saturated and unsaturated fatty acids and longer chain saturated fatty acids. There has been growing interest in including PUFAs, such as eicosapentaenoic acid ["EPA"; omega-3] and docosahexaenoic acid ["DHA"; omega-3], in pharmaceutical and dietary products. Means to efficiently and cost-effectively produce lipid compositions comprising PUFAs are therefore particularly desirable.

There are a variety of commercial sources of PUFAs. However, there are several disadvantages associated with these methods of production using natural sources. First, natural sources, such as fish and plants, tend to have highly heterogeneous oil compositions. The oils obtained from these sources therefore can require extensive purification to separate or enrich one or more of the desired PUFAs. Fish oils commonly have unpleasant tastes and odors, which may be impossible to separate economically from the desired product and can render such products unacceptable as food supplements. Unpleasant tastes and odors can make medical regimens based on ingestion of high dosages undesirable, and may inhibit compliance by the patient.

Fish may accumulate environmental pollutants and ingestion of fish oil capsules as a dietary supplement may result in ingestion of undesired contaminants. Natural sources of PUFAs are also subject to uncontrollable fluctuations in availability (e.g., due to weather, disease, or over-fishing in the case of fish stocks). Also, crops that produce PUFAs often are not competitive economically with hybrid crops developed for food production. Large-scale fermentation of some organisms that naturally produce PUFAs (e.g., *Porphyridium*, *Mortierella*) can also be expensive and/or difficult to cultivate on a commercial scale. As a result of these limitations, extensive work has been conducted toward the development of recombinant oleaginous microorganisms that can produce PUFAs efficiently and economically at a commercial scale (e.g., U.S. Pat. Appl. Publ. No. 2005-0136519-A1). Additionally, the modification of fatty acid biosynthetic pathways in recombinant oleaginous microorganisms to enable production of desired PUFAs has also been reported (e.g., U.S. Pat. Appl. Publ. Nos. 2006-0110806-A1, 2006-0115881-A1, 2009-0093543-A1, and 2010-0317072-A1). However, there is still a need for recombinant oleaginous microorganisms having increased oil content relative to the oil of currently known strains.

U.S. Pat. No. 7,256,014 discloses that the expression of at least one plant oleosin gene in a microbial cell engineered to produce a hydrophobic/lipophilic compound, such as a carotenoid, significantly increases the overall titer of the compound.

Froissard et al. (*FEMS Yeast Res.* 9:428-438, 2009) disclose that the non-oleaginous yeast, *Saccharomyces cerevisiae*, transformed with a heterologous gene encoding a caleosin polypeptide (*Arabidopsis thaliana* caleosin 1, AtClo1), exhibited an increase in the number and size of lipid bodies and accumulated more fatty acids than the parent strain.

However, there are no reports of recombinant oleaginous microorganisms transformed with a gene encoding a caleosin polypeptide to increase the oil content of such recombinant microbial cells.

SUMMARY

In a first embodiment, the invention provides a recombinant oleaginous microorganism that produces at least 25% of its dry cell weight as oil and that comprises a functional polyunsaturated fatty acid biosynthetic pathway and at least one genetic construct encoding a caleosin polypeptide. The recombinant oleaginous microorganism of this embodiment produces a greater quantity of oil comprising at least one polyunsaturated fatty acid when compared to the quantity of oil produced by a corresponding control.

In a second embodiment, the recombinant oleaginous microorganism may be a yeast, fungus, or alga. In a third embodiment, the recombinant oleaginous microorganism may be *Yarrowia lipolytica*.

In a fourth embodiment, the polyunsaturated fatty acid comprised within the oil produced by the recombinant oleaginous microorganism may be an omega-3 polyunsaturated fatty acid or an omega-6 polyunsaturated fatty acid. In a fifth embodiment, the omega-3 polyunsaturated fatty acid is eicosapentaenoic acid (EPA).

In a sixth embodiment, the caleosin polypeptide encoded by the genetic construct has an amino acid sequence that has at least 90% identity to SEQ ID NO:2, 4, 6, 8, 10, 12, 14, 38, 40, 42, or 51, based on a Clustal W method of alignment. The caleosin polypeptide of this embodiment has caleosin function.

In a seventh embodiment, the caleosin polypeptide encoded by the genetic construct is linked to an enzyme that catalyzes acylation of diacylglycerol. In an eighth embodiment, the enzyme that catalyzes acylation of diacylglycerol is a phospholipid:diacylglycerol acyltransferase (PDAT).

In a ninth embodiment, the caleosin polypeptide contains added cysteine residues with respect to the wild type amino acid sequence of the caleosin polypeptide. The added cysteine residues can be interspersed within the N-terminal and C-terminal regions of the caleosin polypeptide.

In a tenth embodiment, the invention provides a method for increasing the amount of oil contained in a recombinant oleaginous microorganism, comprising the steps of:

a) providing a recombinant oleaginous microorganism of the invention;

b) growing the recombinant oleaginous microorganism of step (a) under conditions whereby oil comprising at least one polyunsaturated fatty acid is produced; and c) optionally, recovering the oil of step (b).

In one aspect of the method, the recombinant oleaginous microorganism may be a yeast, fungus, or alga. In another aspect, the recombinant oleaginous microorganism may be *Yarrowia lipolytica*.

In another aspect of the method, the polyunsaturated fatty acid comprised within the oil produced by the recombinant oleaginous microorganism may be an omega-3 polyunsaturated fatty acid or an omega-6 polyunsaturated fatty acid. In another aspect, the omega-3 polyunsaturated fatty acid is eicosapentaenoic acid (EPA).

In still another aspect of the method, the caleosin polypeptide encoded by the genetic construct has an amino acid sequence that has at least 90% identity to SEQ ID NO:2, 4, 6, 8, 10, 12, 14, 38, 40, 42, or 51, based on a Clustal W method of alignment. The caleosin polypeptide of this aspect has caleosin function.

BRIEF DESCRIPTION OF THE DRAWINGS AND SEQUENCE LISTINGS

FIG. 2 shows an alignment between the amino acid sequences of AtClo1s and cys-AtClo1s. The cysteine residues added to AtClo1s to yield cys-AtClo1s are underlined.

TABLE 1

Figure 1:
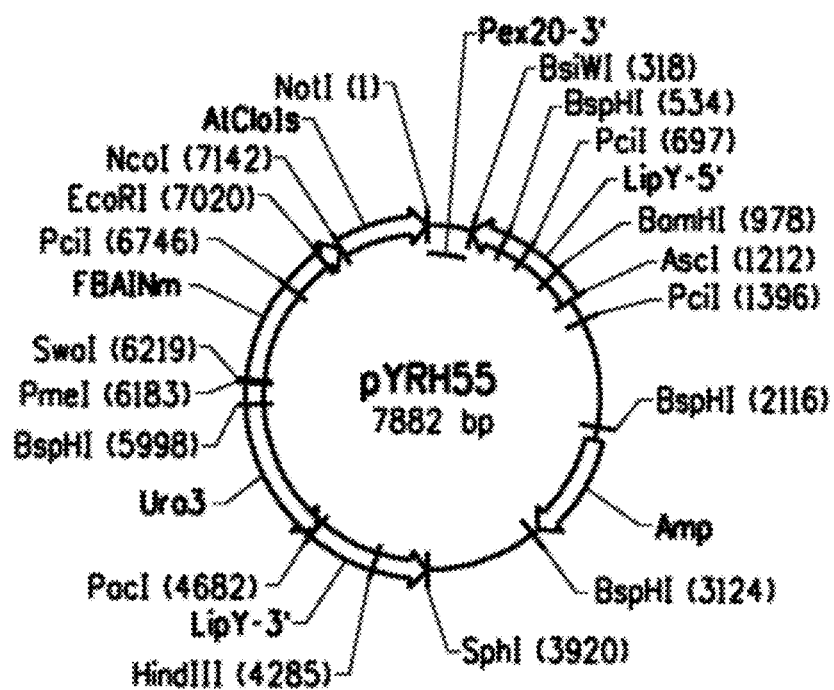
FIG. 1 is a plasmid map of pYRH55, which is described in Example 1 herein.

Summary of Nucleic Acid and Protein SEQ ID Numbers

| Description | Coding Sequence SEQ ID NO: | Encoded Protein SEQ ID NO: |
|---|---|---|
| Caleosin from *Arabidopsis thaliana* (AtClo1) | 1 | 2 |
| Caleosin from *Ricinus communis* (Cal01) | 3 | 4 |
| Caleosin from *Glycine max* (Cal02) | 5 | 6 |
| Caleosin from *Sesamum indicum* (Cal03) | 7 | 8 |
| Caleosin from *Coix lacryma* (Cal04) | 9 | 10 |
| Caleosin from *Aspergillus niger* (Cal05) | 11 | 12 |
| Caleosin from *Neurospora crassa* (Cal06) | 13 | 14 |
| At5G55240 caleosin-related family protein from *Arabidopsis thaliana* | 15 | 16 |
| At2G33380 caleosin-related family protein from *Arabidopsis thaliana* | 17 | 18 |
| At1G70670 caleosin-related family protein from *Arabidopsis thaliana* | 19 | 20 |
| AT1G23240 caleosin-related family protein from *Arabidopsis thaliana* | 21 | 22 |
| CaBP1 calcium binding protein from *Hordeum vulgare* | 23 | 24 |
| Calcium-binding protein from *Fagus sylvatica* | 25 | 26 |
| Putative ABA-induced protein from *Cynodon dactylon* | 27 | 28 |
| Hypothetical protein from *Aspergillus nidulans* | 29 | 30 |
| Hypothetical protein from *Magnaporthe grisea* | 31 | 32 |
| Caleosin from *Arabidopsis thaliana*, codon-optimized for expression in *Yarrowia* (AtClo1s) | 33 | 2 |
| Caleosin from *Ricinus communis*, codon-optimized for expression in *Yarrowia* (Cal01s) | 34 | 4 |
| Caleosin from *Glycine max*, codon-optimized for expression in *Yarrowia* (Cal02s) | 35 | 6 |
| Caleosin from *Sesamum indicum*, codon-optimized for expression in *Yarrowia* (Cal03s) | 36 | 8 |
| Caleosin from *Coix lacryma*, codon-optimized for expression in *Yarrowia* (Cal04s) (has Q2E amino acid change) | 37 | 38 |
| Caleosin from *Aspergillus niger*, codon-optimized for expression in *Yarrowia* (Cal05s) (has P2A amino acid change) | 39 | 40 |
| Caleosin from *Neurospora crassa*, codon-optimized for expression in *Yarrowia* (Cal06s) (has P2A amino acid change) | 41 | 42 |
| Construct pYRH55 (for AtClo1s expression) | 43 | |
| Construct pYRH84 (for Cal01s expression) | 44 | |
| Construct pYRH85 (for Cal02s expression) | 45 | |
| Construct pYRH86 (for Cal03s expression) | 46 | |
| Construct pYRH88 (for Cal04s expression) | 47 | |
| Construct pYRH89 (for Cal05s expression) | 48 | |
| Construct pYRH90 (for Cal06s expression) | 49 | |
| cys-AtClo1s (AtClo1s modified to contain multiple cysteine residues) | 50 | 51 |
| cys-AtClo1s::PDAT fusion protein | 52 | 53 |
| PDAT::cys-AtClo1s fusion protein | 54 | 55 |
| cys-AtClo1s::LPCAT fusion protein | 56 | 57 |
| LPCAT::cys-AtClo1s fusion protein | 58 | 59 |
| Linker used in fusion proteins | | 60 |
| Construct pYRH95 (for cys-AtClo1s expression) | 61 | |
| Construct pYRH96 (for cys-AtClo1s::PDAT fusion protein expression) | 62 | |
| Construct pYRH97 (for PDAT::cys-AtClo1s fusion protein expression) | 63 | |
| Construct pYRH98 (for cys-AtClo1s::LPCAT fusion protein expression) | 64 | |
| Construct pYRH99 (for LPCAT::cys-AtClo1s fusion protein expression) | 65 | |

DETAILED DESCRIPTION OF THE INVENTION

The disclosures of all patent and non-patent literature cited herein are incorporated herein by reference in their entirety.

In this disclosure, the following terms and abbreviations are used:

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA (s)" or "PUFAs".

"Triacylglycerols" are abbreviated as "TAGs".

"Total fatty acids" are abbreviated as "TFAs".

"Fatty acid methyl esters" are abbreviated as "FAMEs".

"Dry cell weight" is abbreviated as "DCW".

As used herein, the term "invention" or "present invention" is not meant to be limiting but applies generally to any of the inventions defined in the claims or described herein.

The term "caleosin function" as used herein refers to intracellular localization of caleosin to lipid bodies and/or the endoplasmic reticulum (ER). Preferably, the caleosin polypeptide localizes to lipid bodies. Immunofluorescence microscopy, electron microscopy, and subcellular fractionation (e.g., density gradient centrifugation) are examples of well known analyses that can be used to determine caleosin localization. Caleosin polypeptide function can also include the ability of caleosin to bind calcium cations ($Ca^{2+}$), which process is believed to play a role in lipid body fusion (Murphy et al., 2000, *Biochem. Soc. Trans.* 28:710-711). Calcium binding by a caleosin polypeptide can be determined using a process described by Chen et al. (1999, *Plant Cell Physiol.*, 40:1079-1086), for example, which involves determining whether a calcium chelator such as EGTA is able to change the electrophoretic mobility of caleosin. Caleosin function alternatively includes the ability of caleosin to contribute to an increase in total lipid levels in an oleaginous cell or microorganism upon the overexpression of caleosin therein; examples of such an analysis are provided herein.

The term "fusion protein" refers to a single polypeptide having at least two independent and separable enzymatic activities, functionalities, and/or binding activities. The terms "multizyme" and "fusion protein" are used interchangeably herein. Preferably, a multizyme comprises a first enzymatic activity linked to a second enzymatic activity, functionality, or binding activity.

The term "link" refers to joining or bonding at least two polypeptides having independent and separable enzyme, functional, and/or binding activities. The terms "link" and "linked to" are used interchangeably herein.

The term "linker" refers to the bond or link between two or more polypeptides in a multizyme or fusion protein. The link used to form a multizyme is minimally comprised of a single polypeptide bond. In another aspect, the link may be comprised of one amino acid residue, such as proline, or a polypeptide. If the link is a polypeptide, it may be desirable for the link to have at least one proline amino acid residue.

The term "oleaginous" refers to those organisms that tend to store their energy source in the form of oil (Weete, In: Fungal Lipid Biochemistry, 2nd Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*.

The terms "ω-3 fatty acids", "n-3 fatty acids" and "omega-3 fatty acids" are used interchangeably herein.

The terms "ω-6 fatty acids", "n-6 fatty acids" and "omega-6 fatty acids" are used interchangeably herein.

The terms "Δ" and "delta" are used interchangeably herein when referring to desaturases.

The term "lipids" refer to any fat-soluble (i.e., lipophilic), naturally-occurring molecule. A general overview of lipids is provided in U.S. Pat. Appl. Pub. No. 2009-0093543-A1 (see Table 2 therein), which is incorporated herein by reference.

The term "oil" refers to a lipid substance that is liquid at 25° C. and usually polyunsaturated. In oleaginous organisms, oil constitutes a major part of the total lipid. "Oil" is composed primarily of triacylglycerols but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

The term "produces a greater quantity of oil", as used herein, means that the amount of oil or total lipids recovered from a recombinant oleaginous microorganism disclosed herein is greater than the amount of oil or total lipids recovered from a corresponding control that could be a corresponding wild type microorganism, or a recombinant oleaginous microorganism not comprising the genetic construct encoding a caleosin polypeptide or that comprises but does not express the genetic construct encoding a caleosin polypeptide. For example, the corresponding control may be the recombinant oleaginous microorganism before it was modified to contain the caleosin-encoding genetic construct (i.e., a parent strain), or the recombinant oleaginous microorganism that has been modified to contain the caleosin-encoding genetic construct but which does not express the caleosin. The amount of oil or total lipids produced by a recombinant oleaginous microorganism as described herein may increase at least about 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% relative to the total lipid/oil content of the corresponding control recombinant oleaginous microorganism.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon atoms in the particular fatty acid and Y is the number of double bonds. Additional details concerning the differentiation between "saturated fatty acids" versus "unsaturated fatty acids", "monounsaturated fatty acids" versus PUFAs, and "omega-6 fatty acids" versus "omega-3 fatty acids" are provided in U.S. Pat. No. 7,238,482, which is incorporated herein by reference.

The term "total fatty acids" ["TFAs"] herein refers to the sum of all cellular fatty acids that can be derivatized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including, e.g., the PC and the PE fractions) but not free fatty acids.

The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to the concentration of the fatty acid as % TFAs (e.g., % EPA of total lipids is equivalent to EPA % TFAs).

In some cases, it is useful to express the content of a given fatty acid(s) in a cell as its weight percent of the dry cell weight ["% DCW"]. Thus, for example, EPA % DCW would be determined according to the following formula: (EPA % TFAs)*(TFAs % DCW)]/100. The content of a given fatty acid(s) in a cell as its weight percent of the dry cell weight ["% DCW"] can be approximated, however, as: (EPA % TFAs)* (FAMEs % DCW)]/100.

The terms "polyunsaturated fatty acid(s)" and "PUFA(s)" as used herein refer to fatty acids having at least 18 carbon atoms and 2 or more double bonds.

Nomenclature used to describe PUFAs herein is given in Table 2. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of Table 2 summarizes the common names of omega-3 and omega-6 fatty acids and their precursors, the abbreviations that are used throughout the specification and the chemical name of each compound.

TABLE 2

Nomenclature of Polyunsaturated Fatty Acids and Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| gamma-Linolenic | GLA | cis-6,9,12-octadecatrienoic | 18:3 ω-6 |
| Eicosadienoic | EDA | cis-11,14-eicosadienoic | 20:2 ω-6 |
| Dihomo-gamma-Linolenic | DGLA | cis-8,11,14-eicosatrienoic | 20:3 ω-6 |
| Arachidonic | ARA | cis-5,8,11,14-eicosatetraenoic | 20:4 ω-6 |
| alpha-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosatetraenoic | DTA | cis-7,10,13,16-docosatetraenoic | 22:4 ω-3 |
| Docosapentaenoic | DPAn-6 | cis-4,7,10,13,16-docosapentaenoic | 22:5 ω-6 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The terms "PUFA biosynthetic pathway" and "omega-3/omega-6 fatty acid biosynthetic pathway" are used interchangeably herein and refer to a metabolic process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This process is well described in the literature (e.g., see U.S. Pat. Appl. Publ. No. 2006-0115881-A1, which is incorporated herein by reference). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase (delta-6 elongase or delta-9 elongase) and/or $C_{20/22}$ elongase. The term "functional" as used herein in context with the omega-3/omega-6 fatty acid biosynthetic pathway means that some or all of the genes in the pathway express active enzymes. It should be understood that "omega-3/omega-6 fatty acid biosynthetic pathway" or "functional omega-3/omega-6 fatty acid biosynthetic pathway" does not imply that all the genes listed in this paragraph are required as a number of fatty acid products will only require the expression of a subset of the genes of this pathway.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* 2nd ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions includes hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the thermal melting point ["$T_m$," or "Tm"] for hybrids of nucleic acids having those sequences. The relative stability, corresponding to higher Tm, of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as the Basic Local Alignment Search Tool ["BLAST"] (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation, such as, in situ hybridization of microbial colonies or bacteriophage plaques. In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The skilled artisan, having the benefit of the sequences as reported herein, may now use all or a substantial portion of the disclosed sequences for purposes known to those skilled in this art, based on the methodologies described herein.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, such as 0.5×SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments.

The term "percent identity" refers to a relationship between two or more polypeptide sequences or two or more polynucleotide sequences, as determined by comparing the sequences. "Percent identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Preferred methods to determine percent identity are designed to give the best match between the sequences tested. Methods to determine percent identity and percent similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides from other species, wherein such polypeptides have the same or similar function or activity. Suitable nucleic acid fragments, i.e., isolated polynucleotides encoding polypeptides in the methods and host cells described herein, encode polypeptides that are at least about 70-85% identical, while more preferred nucleic acid fragments encode amino acid sequences that are at least about 85-95% identical to the amino acid sequences reported herein. Although preferred ranges are described above, useful examples of percent identities include any integer percentage from 50% to 100%, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672, which is incorporated herein by reference.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; Int'l App. Pub. No. WO 99/28508).

The term "operably linked" refers to the association of nucleic acid sequences on a single nucleic acid fragment so that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation. Also for example, a coding sequence may be operably linked to a 3' transcription terminator sequence.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA derived from nucleic acid fragments. Expression may also refer to translation of mRNA into a polypeptide. Thus, the term "expression", as used herein, also refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic", "recombinant", "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA containing a foreign gene and having elements in addition to the foreign gene that allow for enhanced expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence, i.e., open reading frame ["ORF"]; and, 3) a 3' untranslated region, e.g., a terminator that in eukaryotes usually contains a polyadenylation site. The expression cassette(s) is usually included within a vector, to facilitate cloning and transformation. Different expression cassettes can be transformed into different organisms including bacteria, yeast, plants and mammalian cells, as long as the correct (suitable) regulatory sequences are used for each host.

The terms "genetic construct", "recombinant construct", "expression construct" and "construct" are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain lines displaying the desired expression level and pattern.

The term "sequence analysis software" refers to any computer algorithm or software program that is useful for the analysis of nucleotide or amino acid sequences. "Sequence analysis software" may be commercially available or independently developed. Typical sequence analysis software include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNAS-TAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" means any set of values or parameters that originally load with the software when first initialized.

Disclosed herein are recombinant oleaginous microorganisms that produce at least 25% of their dry cell weight as oil and that comprise a functional polyunsaturated fatty acid biosynthetic pathway and at least one genetic construct encoding a caleosin polypeptide. The recombinant oleaginous microorganisms of the present invention produce a greater quantity of oil comprising at least one polyunsaturated fatty acid when compared to the quantity of oil produced by a corresponding control.

Suitable host microorganisms for use in the construction of the recombinant oleaginous microorganisms disclosed herein are oleaginous microorganisms which are capable of oil synthesis and accumulation, commonly accumulating in excess of about 25% of their dry cell weight as oil. Various yeast, fungi and algae are classified as oleaginous. More preferred are oleaginous yeasts; genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). The most preferred oleaginous yeast is *Yarrowia lipolytica*; and most preferred are *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)). In alternative embodiments, a non-oleaginous microorganism can be genetically modified to become oleaginous, e.g., yeast such as *Saccharomyces cerevisiae*.

As an example, several yeast organisms have been recombinantly engineered to produce at least one PUFA. See for example, work in *Saccharomyces cerevisiae* (Dyer, J. M. et al., *Appl. Env. Microbiol.*, 59:224-230 (2002); Domergue, F. et al., *Eur. J. Biochem.*, 269:4105-4113 (2002); U.S. Pat. No. 6,136,574; U.S. Pat. Appl. Publ. No. 2006-0051847-A1) and the oleaginous yeast, *Yarrowia lipolytica* (U.S. Pat. Nos. 7,238,482; 7,465,564; 7,588,931; U.S. Pat. Appl. Publ. No. 2006-0115881-A1; U.S. Pat. No. 7,550,286; U.S. Pat. Appl. Publ. No. 2009-0093543-A1; U.S. Pat. Appl. Publ. No. 2010-0317072-A1).

Thus, PUFA biosynthetic pathway genes and gene products described herein may be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Although numerous oleaginous yeast could be engineered for production of preferred omega-3/omega-6 PUFAs based on the cited teachings provided above, representative PUFA-producing strains of the oleaginous yeast *Yarrowia lipolytica* are described in Table 3 below. These strains possess various combinations of the following PUFA biosynthetic pathway genes: delta-4 desaturases, delta-5 desaturases, delta-6 desaturases, delta-12 desaturases, delta-15 desaturases, delta-17 desaturases, delta-9 desaturases, delta-8 desaturases, delta-9 elongases, $C_{14/16}$ elongases, $C_{16/18}$ elongases, $C_{18/20}$ elongases and $C_{20/22}$ elongases, although it is to be recognized that the specific enzymes (and genes encoding those enzymes) introduced and the specific PUFAs produced are by no means limiting to the invention herein.

Caleosins are one of the minor proteins associated with seed lipid bodies, in which cells in plant seeds store triacylglycerides. Caleosins have a similar three-domain structure to oleosins, the most abundant proteins associated with lipid or oil bodies, specifically, a highly conserved domain of central 70-80 non-polar residues flanked by amphipathic N- and C-terminal regions. In the middle of the central hydrophobic region lies the so-called "proline-knot" motif required for correct targeting to lipid bodies. The N- and C-terminal domains interact with the phospholipid head groups at the surface of the lipid bodies. Caleosins also possess a highly conserved EF-hand loop motif (Naested et al. 2000, *Plant Mol. Biol.* 44, 463-476, and Hanano et al. 2006, *J. Biol. Chem.*, 44, 33140-33151) located at the N-terminal region corresponding to a calcium biding site, and putative phosphorylation sites at the C-terminal region. This single calcium binding EF-hand motif is a rare and novel feature among the hundreds of EF-hand proteins. In most cases, EF-hands are found in pairs to bind two calcium ions cooperatively with high affinity. Naested et al. (above) proposed that caleosin's single EF-hand domains are involved in membrane fusion between lipid bodies or cellular organelles in order to form pairs of EF-hands. Therefore, caleosins may be involved in a lipid trafficking process between ER (endoplasmic reticulum) and lipid bodies. In support of this idea, localization studies showed that caleosins are associated with ER, vacuoles, and lipid bodies, unlike oleosins which are directly associated with lipid bodies (Frandsen et al., 1996, *J. Biol. Chem.* 271, 343-348, Naested et al., above, and Liu et al., 2005, *Planta*, 221, 513-522).

Caleosin polypeptides that can be used in the invention are found in seeds of plants such as *Arabidopsis thaliana*, rapeseed, sesame, sunflower, soybean, loblolly pine, rice, tomato, maize, barley and peanut, in fungi such as *Neurospora crassa* and *Aspergillus nidulans*, and in algae such as *Chlorella protothecoides*. Thus, a plant caleosin, fungal caleosin, and/or an algal caleosin can be used in the present invention. Other examples of plant caleosin polypeptides are provided by GenBank Accession Nos. NP_001151906.1, AAF13743.1, ACJ70083.1, XP_003626887.1, ACP27620.1, ABV72237.1, ABY56103.1, ABB05052.1, AAY40837.1, AEE85247.1, NP_194404.1, ABK40508.1, AAY87906.1, ABF94710.1, AAQ74240.1, AAQ74239.1, AAQ74238.1, BAD16161.1, NP_173738.2, NP_173739.4 and AEC08825.1. Other examples of fungal caleosin polypeptides are provided by GenBank Accession Nos. EAL91241.1, XP_753279.1, EHA56268.1, EHA51085.1, EGX88252.1, XP_001822392.2, XP_001397384.1, GAA84711.1, EGY20893.1, EED23685.1, EFY86741.1, CBF78379.1, EED47644.1, EDP52113.1, EAW17406.1, EDU41523.1, XP_001828377.2, EAU93369.2, XP_002382486.1 and XP_002341072.1. Other examples of algal caleosin polypeptides are provided by GenBank Accession Nos. AEB77763.1, EIE19762.1, EIE19761.1, EDP09778.1, EFN52997.1, XP_002958325.1, XP_002945870.1, EFJ52865.1, EFJ40618.1, XP_001696463.1, XP_001695367.1, CAB42585.1 and EDP01625.1.

Caleosin polypeptides suitable for use in the present invention also include, but are not limited to, polypeptides comprising an amino acid sequence as set forth in SEQ ID NOs:2, 4, 6, 8, 10, 12, 14, 16, 18, 20, 22, 24, 26, 28, 30, 32, 38, 40, 42 and 51.

Caleosin polypeptides have caleosin function as defined above.

In one embodiment, the caleosin polypeptide comprises an amino acid sequence selected from the group consisting of SEQ ID NOs:2, 4, 6, 8, 10, 12, 14, 38, 40, 42 and 51. In another embodiment, the caleosin polypeptide comprises the amino acid sequence set forth in SEQ ID NO:2.

As is well known in the art, these caleosin polypeptide sequences may be used to readily search for caleosin homologs in the same or other species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul et al., *Nucleic Acids Res.*, 25:3389-3402 (1997)), is well understood for comparing protein sequences against a database of protein sequences and thereby identifying similar known sequences within a preferred organism.

Use of a software algorithm to comb through databases of known sequences is particularly suitable for the isolation of homologs having a relatively low percent identity to publicly available caleosin polypeptide sequences, such as those listed above. It is predictable that isolation would be relatively easier for caleosin homologs of at least about 70%-85% identity to publicly available caleosin sequences. Further, those sequences that are at least about 85%-90% identical would be particularly suitable for isolation and those sequences that are at least about 90%-95% identical would be the most easily isolated.

In one embodiment, the caleosin polypeptide has at least 90% or 95% sequence identity, based on the Clustal W method of alignment, to an amino acid sequence as set forth in SEQ ID NOs:2, 4, 6, 8, 10, 12, 14, 16, 18, 20, 22, 24, 26, 28, 30, 32, 38, 40, 42 and 51, wherein the caleosin polypeptide has caleosin function (above).

In another embodiment, the caleosin polypeptide has at least 90% or 95% sequence identity, based on the Clustal W method of alignment, to an amino acid sequence as set forth in SEQ ID NOs:2, 4, 6, 8, 10, 12, 14, 38, 40, 42 and 51, wherein the caleosin polypeptide has caleosin function (above).

In another embodiment, the caleosin polypeptide has at least 90% or 95% sequence identity, based on the Clustal W method of alignment, to an amino acid sequence as set forth in SEQ ID NO:2, wherein the caleosin polypeptide has caleosin function (above).

Additionally, any of the caleosin-encoding nucleic acid fragments described herein or in public literature, or any identified homologs, may be used to isolate genes encoding homologous proteins from the same or other species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as PCR (U.S. Pat. No. 4,683, 202); ligase chain reaction (Tabor, S. et al., *Proc. Natl. Acad. Sci. U.S.A.* 82:1074 (1985)); or strand displacement amplification (Walker et al., *Proc. Natl. Acad. Sci. U.S.A.* 89:392 (1992)); and 3) methods of library construction and screening by complementation.

For example, genes encoding proteins or polypeptides similar to publicly available caleosin genes or their motifs could be isolated directly by using all or a portion of those publicly available nucleic acid fragments as DNA hybridization probes to screen libraries from any desired organism using well known methods. Specific oligonucleotide probes based upon the publicly available nucleic acid sequences can be designed and synthesized by methods known in the art (Maniatis). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part or the full length of the publicly available sequences or their motifs. The resulting amplification products can be labeled directly during amplification reactions or labeled after amplification reactions, and used as probes to isolate full-length DNA fragments under conditions of appropriate stringency.

Based on any of the well-known methods just discussed, it would be possible to identify and/or isolate caleosin gene homologs in any preferred organism of choice.

Heterologous genes encoding caleosin polypeptides are unlikely to share the same codon preference in the host microorganism. Therefore, it may be desirable to optimize codon usage for the desired host microorganism. As is known in the art, the codon usage can be optimized according to the codon usage pattern of the host microorganism, the consensus sequence around the 'ATG' translation initiation codon, and the general rules of RNA stability (Guhaniyogi, G. and J. Brewer, *Gene,* 265(1-2):11-23 (2001)). For example, the coding sequence of a caleosin gene may be optimized for expression in *Yarrowia lipolytica* in a manner as described in Int'l Appl. Publ. No. WO 2004/101753 and U.S. Pat. No. 7,125, 672, according to the *Yarrowia* codon usage pattern (Int'l Appl. Publ. No. WO 2004/101753). A codon-optimized AtClo1 coding sequence for expression in *Yarrowia lipolytica* (designated "AtClo1s") is set forth in SEQ ID NO:33.

Certain embodiments of the invention are drawn to a recombinant oleaginous microorganism that produces at least 25% of its dry cell weight as oil, and that comprises a functional polyunsaturated fatty acid biosynthetic pathway and at least one genetic construct encoding a caleosin polypeptide that is linked to another protein such as an enzyme that catalyzes acylation of diacylglycerol.

Examples of an enzyme that catalyzes acylation of diacylglycerol are acyl-CoA:diacylglycerol acyl transferase (DGAT, EC 2.3.1.20; e.g., isoforms DGAT-1 and DGAT-2) and phospholipid:diacylglycerol acyltransferase (PDAT, E.G. 2.3.1.158). In a preferred embodiment, the enzyme that catalyzes acylation of diacylglycerol is a *Yarrowia lipolytica* DGAT or PDAT. Examples of DGAT and PDAT enzymes of use in the invention are disclosed in U.S. Pat. Nos. 7,901,928, 7,273,746 and 7,267,976, all of which are incorporated herein by reference. The enzyme that catalyzes acylation of diacylglycerol may be derived from a source that is heterologous to, or native to, the recombinant oleaginous microorganism of the invention.

In certain embodiments of the invention, a linker peptide mediates the fusion between the caleosin polypeptide and the enzyme that catalyzes acylation of diacylglycerol. The linker peptide may contain 1, 2, 3, 4, 5, 6, 7, 8, 9, 10, 11, 12, 13, 14, 15, 16, 17, 18, 19, 20, 21, 22, 23, 24, or 25 or more amino acid residues. An example of a linker that can be used in the invention is SEQ ID NO:60, which has 24 amino acids. Other examples of linkers useful herein are disclosed in U.S. Pat. Appl. Publ. No. 2008-0254191-A1, which is incorporated herein by reference. Alternatively, a peptide bond may be used to link the caleosin polypeptide with the enzyme that catalyzes acylation of diacylglycerol.

The caleosin polypeptide, when linked to an enzyme that catalyzes acylation of diacylglycerol, can be located at the N-terminal end (i.e., amino-terminus) or C-terminal end (i.e., carboxy-terminus) of the fusion protein. In other words, the order of the linkage does not matter. The first 1, 2, 3, 4, 5, or 6 amino acid residues of the C-terminal protein may be modified accordingly to accommodate creating the fusion. The caleosin polypeptide, when used in the invention as a fusion protein, has caleosin function (above).

Examples of fusion proteins containing a caleosin polypeptide and an enzyme that catalyzes acylation of diacylglycerol are SEQ ID NOs:53 and 55, in which a particular *A. thaliana*-derived caleosin is linked to a *Yarrowia*-derived PDAT. The caleosin is located N-terminal to PDAT in SEQ ID NO:53, and C-terminal to PDAT in SEQ ID NO:55. In certain embodiments, the fusion protein has at least 90% or 95% sequence identity to SEQ ID NO:53 or 55, based on the Clustal W method of alignment, where the caleosin portion of the fusion protein has caleosin function (above).

In certain embodiments of the invention, the caleosin polypeptide encoded by the genetic construct contains added cysteine residues. The cysteine residues are "added" with respect to the wild type amino acid sequence of the caleosin polypeptide. When a caleosin localizes to a lipid body, the generally hydrophilic N- and C-terminal regions of the caleosin localize on the lipid body surface, while the more hydrophobic intermediate region imbeds within the lipid body. Additional cysteine residues, when interspersed within the N- and/or C-terminal regions of a caleosin polypeptide, are therefore believed to create sites for disulfide bond formation between adjacent caleosin polypeptides at the lipid body surface. Such disulfide bond formation between caleosins can yield dimerized or polymerized caleosins.

At least 1, 2, 3, 4, 5, 6, 7, 8, 9, or 10 cysteine residues may be added to the caleosin polypeptide. Such a modified caleosin, or "cys-caleosin," can have a total number of 3, 4, 5, 6, 7, 8, 9, 10, 11, or 12 cysteines, counting both the naturally occurring and added cysteines. Cysteine residues can be added to both the N- and C-terminal ends of a caleosin, where the N-terminal region encompasses approximately the first 90 to 100 amino acid residues of the caleosin, and the C-terminal region encompasses approximately the last 100 to 110 amino acids of the caleosin. As an example, 3, 4 or 5 cysteine residues may be added to both the N- and C-terminal regions of a caleosin polypeptide. Preferably, the cysteines of the cys-caleosin are spaced within the N- and C-terminal regions at intervals of 7, 8, 9, 10, 11, 12, 13, 14, or 15 amino acids from each another, with an average interval of 10 amino acids. Cysteines may be added to a caleosin of the invention by mutation of an amino acid and/or by insertion using, for example, site-specific mutagenesis of a nucleotide sequence encoding the caleosin.

An example of a cys-caleosin polypeptide useful in the invention is SEQ ID NO:51. This polypeptide is a particular *A. thaliana*-derived caleosin modified to have an additional five and three cysteine residues in its N- and C-terminal regions, respectively. In certain embodiments, a cys-caleosin of the invention has at least 90% or 95% sequence identity to SEQ ID NO:51, based on the Clustal W method of alignment, where the cys-caleosin has caleosin function (above).

A gene encoding a caleosin polypeptide may be introduced into a host microorganism as part of a genetic construct using methods known in the art. For example, the gene may be introduced into the host cells on a plasmid. Additionally, the gene may be integrated into the chromosome with appropriate regulatory sequences. The gene may be modified so as to be under the control of non-native promoters or altered native promoters. Endogenous promoters can be altered in vivo by mutation, deletion, and/or substitution. The gene encoding a caleosin polypeptide may be introduced into the host microorganism on a separate genetic construct or as part of the genetic construct(s) encoding the functional polyunsaturated fatty acid biosynthetic pathway using the methods described below.

The recombinant oleaginous microorganisms of the present invention comprise at least one genetic construct encoding a functional polyunsaturated fatty acid biosynthetic pathway. Numerous microorganisms have been genetically engineered to produce long-chain polyunsaturated fatty acids by introduction of the appropriate combination of desaturase (i.e., delta-12 desaturase, delta-6 desaturase, delta-8 desaturase, delta-5 desaturase, delta-17 desaturase, delta-15 desaturase, delta-9 desaturase, delta-4 desaturase) and elongase (i.e., $C_{14/16}$ elongase, $C_{16/18}$ elongase, $C_{18/20}$ elongase, $C_{20/22}$ elongase and delta-9 elongase) genes. See, for example, work in *Saccharomyces cerevisiae* (Dyer, J. M. et al., *Appl. Env. Microbiol.*, 59:224-230 (2002); Domergue, F. et al., *Eur. J. Biochem.*, 269:4105-4113 (2002); U.S. Pat. No. 6,136,574; U.S. Pat. Appl. Publ. No. 2006-0051847-A1), in the marine cyanobacterium *Synechococcus* sp. (Yu et al., *Lipids*, 35(10): 1061-1064 (2006)), in the methylotrophic yeast *Pichia pastoris* (Kajikawa et al., *Plant Mol. Biol.*, 54(3):335-52 (2004)) and in the moss *Physcomitrella patens* (Kaewsuwan et al., *Bioresource Technol.*, 101(11):4081-4088 (2010)).

In some embodiments, expression of native desaturase enzymes is preferred over a heterologous (or "foreign") enzyme since: 1) the native enzyme is optimized for interaction with other enzymes and proteins within the cell; and 2) heterologous genes are unlikely to share the same codon preference in the host organism. Additionally, advantages are incurred when the sequence of the native gene is known, as it permits down-regulation of the endogenous gene, if desired.

However, in many instances, the appropriate desaturases and elongases are not present in the host microorganism of choice to enable production of the desired PUFA products.

Oleaginous microorganisms can be engineered to produce omega-3/omega-6 PUFAs by integration of appropriate heterologous genes encoding desaturases and elongases of the delta-6 desaturase/delta-6 elongase pathway or the delta-9 elongase/delta-8 desaturase pathway into the host microorganism for production of any particular PUFA of interest. Preferred genes, considerations for choosing a specific polypeptide having desaturase or elongase activity, and means to engineer a PUFA biosynthetic pathway into an oleaginous microorganism are detailed in U.S. Pat. Nos. 7,238,482, 7,465,564, 7,588,931 and 7,550,286, and U.S. Pat. Appl. Publ. No. 2006-0115881-A1 and U.S. Pat. Appl. Publ. No. 2009-0093543-A1. These references also describe details concerning additional modifications that may be required to enable high level production of a particular PUFA, including: 1) manipulation of the activity of acyltransferases that allow for efficient biosynthesis and transfer of omega fatty acids into storage lipid pools (i.e., the TAG fraction); 2) over-expression of desaturases, elongases and diacylglycerol cholinephosphotransferases by use of strong promoters, expression in multicopy, and/or codon-optimization; 3) down-regulation of the expression of specific genes such as those involved in beta-oxidation, which increases overall accumulation of the desired PUFA; 4) manipulation of pathways and global regulators that affect production of the desired PUFA; and, 5) "pushing/pulling" within the PUFA biosynthetic pathway. In addition, U.S. Pat. Appl. Publ. No. 2008-0254191-A1, and in particular, Examples 55 and 56 therein which are incorporated herein by reference, describe DGLA synthases (multizymes) that possess improved enzymatic activity with respect to their individual delta-9 elongase and/or delta-8 desaturase counterparts, when heterologously expressed in oleaginous yeasts. Surprisingly, fusing the two independent enzymes together as one fusion protein separated by a linker region increased flux from LA to DGLA, suggesting that the product of delta-9 elongase may be directly channeled as substrate of delta-8 desaturase in the fusion protein.

Table 3 describes *Y. lipolytica* strains possessing various combinations of the following PUFA biosynthetic pathway genes: delta-4 desaturases, delta-5 desaturases, delta-6 desaturases, delta-12 desaturases, delta-15 desaturases, delta-17 desaturases, delta-9 desaturases, delta-8 desaturases, delta-9 elongases, $C_{14/16}$ elongases, $C_{16/18}$ elongases, $C_{18/20}$ elongases and $C_{20/22}$ elongases, although it is to be recognized that the specific enzymes (and genes encoding those enzymes) introduced and the specific PUFAs produced are by no means limiting to the invention herein.

TABLE 3

Lipid Profile of Representative *Y. lipolytica* Strains Engineered to Produce omega-3/omega-6 PUFAs

| Strain | Reference | ATCC Deposit No. | Fatty Acid Content (as a Percent [%] of Total Fatty Acids) | | | | | | | |
|---|---|---|---|---|---|---|---|---|---|---|
| | | | 16:0 | 16:1 | 18:0 | 18:1 | 18:2 | 18:3 (ALA) | GLA | 20:2 (EDA) |
| Wildtype | U.S. Pat. | #76982 | 14 | 11 | 3.5 | 34.8 | 31 | 0 | 0 | — |
| pDMW208 | No. | — | 11.9 | 8.6 | 1.5 | 24.4 | 17.8 | 0 | 25.9 | — |
| pDMW208-D62 | 7,465,564 | — | 16.2 | 1.5 | 0.1 | 17.8 | 22.2 | 0 | 34 | — |
| M4 | U.S. Pat. Appl. Publ. No. 2006-0115881-A1 | — | 15 | 4 | 2 | 5 | 27 | 0 | 35 | — |
| Y2034 | U.S. Pat. | — | 13.1 | 8.1 | 1.7 | 7.4 | 14.8 | 0 | 25.2 | — |
| Y2047 | No. 7,588,931 | PTA-7186 | 15.9 | 6.6 | 0.7 | 8.9 | 16.6 | 0 | 29.7 | — |

TABLE 3-continued

Lipid Profile of Representative *Y. lipolytica* Strains Engineered to Produce omega-3/omega-6 PUFAs

| Strain | Reference | ATCC Deposit No. | DGLA | ARA | ETA | EPA | DPAn-3 | DHA | TFAs % DCW |
|---|---|---|---|---|---|---|---|---|---|
| Y2214 | | — | 7.9 | 15.3 | 0 | 13.7 | 37.5 | 0 | 0 | — |
| EU | U.S. Pat. | — | 19 | 10.3 | 2.3 | 15.8 | 12 | 0 | 18.7 | — |
| Y2072 | Appl. Publ. | — | 7.6 | 4.1 | 2.2 | 16.8 | 13.9 | 0 | 27.8 | — |
| Y2102 | No. 2006- | — | 9 | 3 | 3.5 | 5.6 | 18.6 | 0 | 29.6 | — |
| Y2088 | 0115881- | — | 17 | 4.5 | 3 | 2.5 | 10 | 0 | 20 | — |
| Y2089 | A1 | — | 7.9 | 3.4 | 2.5 | 9.9 | 14.3 | 0 | 37.5 | — |
| Y2095 | | — | 13 | 0 | 2.6 | 5.1 | 16 | 0 | 29.1 | — |
| Y2090 | | — | 6 | 1 | 6.1 | 7.7 | 12.6 | 0 | 26.4 | — |
| Y2096 | | PTA-7184 | 8.1 | 1 | 6.3 | 8.5 | 11.5 | 0 | 25 | — |
| Y2201 | | PTA-7185 | 11 | 16.1 | 0.7 | 18.4 | 27 | 0 | — | 3.3 |
| Y3000 | U.S. Pat. No. 7,550,286 | PTA-7187 | 5.9 | 1.2 | 5.5 | 7.7 | 11.7 | 0 | 30.1 | — |
| Y4001 | U.S. Pat. | — | 4.3 | 4.4 | 3.9 | 35.9 | 23 | 0 | — | 23.8 |
| Y4036 | Appl. Publ. | — | 7.7 | 3.6 | 1.1 | 14.2 | 32.6 | 0 | — | 15.6 |
| Y4070 | No. 2009- | — | 8 | 5.3 | 3.5 | 14.6 | 42.1 | 0 | — | 6.7 |
| Y4086 | 0093543- | — | 3.3 | 2.2 | 4.6 | 26.3 | 27.9 | 6.9 | — | 7.6 |
| Y4128 | A1 | PTA-8614 | 6.6 | 4 | 2 | 8.8 | 19 | 2.1 | — | 4.1 |
| Y4158 | | — | 3.2 | 1.2 | 2.7 | 14.5 | 30.4 | 5.3 | — | 6.2 |
| Y4184 | | — | 3.1 | 1.5 | 1.8 | 8.7 | 31.5 | 4.9 | — | 5.6 |
| Y4217 | | — | 3.9 | 3.4 | 1.2 | 6.2 | 19 | 2.7 | — | 2.5 |
| Y4259 | | — | 4.4 | 1.4 | 1.5 | 3.9 | 19.7 | 2.1 | — | 3.5 |
| Y4305 | | — | 2.8 | 0.7 | 1.3 | 4.9 | 17.6 | 2.3 | — | 3.4 |
| Y4127 | Int'l. Appl. Publ. No. | PTA-8802 | 4.1 | 2.3 | 2.9 | 15.4 | 30.7 | 8.8 | — | 4.5 |
| Y4184 | WO 2008/073367 | — | 2.2 | 1.1 | 2.6 | 11.6 | 29.8 | 6.6 | — | 6.4 |
| Y8404 | U.S. Pat. | — | 2.8 | 0.8 | 1.8 | 5.1 | 20.4 | 2.1 | | 2.9 |
| Y8406 | Appl. Publ. No. 2010- | PTA-10025 | 2.6 | 0.5 | 2.9 | 5.7 | 20.3 | 2.8 | | 2.8 |
| Y8412 | 0317072-A1 | PTA-10026 | 2.5 | 0.4 | 2.6 | 4.3 | 19.0 | 2.4 | | 2.2 |
| Y8647 | | — | 1.3 | 0.2 | 2.1 | 4.7 | 20.3 | 1.7 | | 3.3 |
| Y8649 | | — | 2.4 | 0.3 | 2.9 | 3.7 | 18.8 | 2.2 | | 2.1 |
| Y8650 | | — | 2.2 | 0.3 | 2.9 | 3.8 | 18.8 | 2.4 | | 2.1 |
| Y9028 | | — | 1.3 | 0.2 | 2.1 | 4.4 | 19.8 | 1.7 | | 3.2 |
| Y9031 | | — | 1.3 | 0.3 | 1.8 | 4.7 | 20.1 | 1.7 | | 3.2 |
| Y9477 | | — | 2.6 | 0.5 | 3.4 | 4.8 | 10.0 | 0.5 | | 2.5 |
| Y9497 | | — | 2.4 | 0.5 | 3.2 | 4.6 | 11.3 | 0.8 | | 3.1 |
| Y9502 | | — | 2.5 | 0.5 | 2.9 | 5.0 | 12.7 | 0.9 | | 3.5 |
| Y9508 | | — | 2.3 | 0.5 | 2.7 | 4.4 | 13.1 | 0.9 | | 2.9 |
| Y8143 | | — | 4.2 | 1.5 | 1.4 | 3.6 | 18.1 | 2.6 | | 1.7 |
| Y8145 | | — | 4.3 | 1.7 | 1.4 | 4.8 | 18.6 | 2.8 | | 2.2 |
| Y8259 | | PTA-10027 | 3.5 | 1.3 | 1.3 | 4.8 | 16.9 | 2.3 | | 1.9 |
| Y8367 | | — | 3.7 | 1.2 | 1.1 | 3.4 | 14.2 | 1.1 | | 1.5 |
| Y8370 | | — | 3.4 | 1.1 | 1.4 | 4.0 | 15.7 | 1.9 | | 1.7 |
| Y8670 | | — | 1.9 | 0.4 | 3.4 | 4.3 | 17.0 | 1.5 | | 2.2 |
| Y8672 | | — | 2.3 | 0.4 | 2.0 | 4.0 | 16.1 | 1.4 | | 1.8 |
| Wildtype | U.S. Pat. No. 7,465,564 | #76982 | — | — | — | — | — | — | — |
| pDMW208 | | — | — | — | — | — | — | — | — |
| pDMW208-D62 | | — | — | — | — | — | — | — | — |
| M4 | U.S. Pat. Appl. Publ. No. 2006-0115881-A1 | — | 8 | 0 | 0 | 0 | — | — | — |
| Y2034 | U.S. Pat. No. 7,588,931 | — | 8.3 | 11.2 | — | — | — | — | — |
| Y2047 | | PTA-7186 | 0 | 10.9 | — | — | — | — | — |
| Y2214 | | — | 7.9 | 14 | — | — | — | — | — |
| EU | U.S. Pat. Appl. Publ. No. 2006-0115881-A1 | — | 5.7 | 0.2 | 3 | 10.3 | — | — | 36 |
| Y2072 | | — | 3.7 | 1.7 | 2.2 | 15 | — | — | — |
| Y2102 | | — | 3.8 | 2.8 | 2.3 | 18.4 | — | — | — |
| Y2088 | | — | 3 | 2.8 | 1.7 | 20 | — | — | — |
| Y2089 | | — | 2.5 | 1.8 | 1.6 | 17.6 | — | — | — |
| Y2095 | | — | 3.1 | 1.9 | 2.7 | 19.3 | — | — | — |

TABLE 3-continued

Lipid Profile of Representative *Y. lipolytica* Strains Engineered to Produce omega-3/omega-6 PUFAs

| Strain | Reference | Deposit | | | | | | | |
|---|---|---|---|---|---|---|---|---|---|
| Y2090 | | — | 6.7 | 2.4 | 3.6 | 26.6 | — | — | 22.9 |
| Y2096 | | PTA-7184 | 5.8 | 2.1 | 2.5 | 28.1 | — | — | 20.8 |
| Y2201 | | PTA-7185 | 3.3 | 1 | 3.8 | 9 | — | — | — |
| Y3000 | U.S. Pat. No. 7,550,286 | PTA-7187 | 2.6 | 1.2 | 1.2 | 4.7 | 18.3 | 5.6 | — |
| Y4001 | U.S. Pat. Appl. Publ. No. 2009-0093543-A1 | — | 0 | 0 | 0 | — | — | — | — |
| Y4036 | | — | 18.2 | 0 | 0 | — | — | — | — |
| Y4070 | | — | 2.4 | 11.9 | — | — | — | — | — |
| Y4086 | | — | 1 | 0 | 2 | 9.8 | — | — | 28.6 |
| Y4128 | | PTA-8614 | 3.2 | 0 | 5.7 | 42.1 | — | — | 18.3 |
| Y4158 | | — | 3.1 | 0.3 | 3.4 | 20.5 | — | — | 27.3 |
| Y4184 | | — | 2.9 | 0.6 | 2.4 | 28.9 | — | — | 23.9 |
| Y4217 | | — | 1.2 | 0.2 | 2.8 | 48.3 | — | — | 20.6 |
| Y4259 | | — | 1.9 | 0.6 | 1.8 | 46.1 | — | — | 23.7 |
| Y4305 | | — | 2 | 0.6 | 1.7 | 53.2 | — | — | 27.5 |
| Y4127 | Int'l. Appl. Publ. No. WO 2008/073367 | PTA-8802 | 3.0 | 3.0 | 2.8 | 18.1 | — | — | — |
| Y4184 | | — | 2.0 | 0.4 | 1.9 | 28.5 | — | — | 24.8 |
| Y8404 | U.S. Pat. Appl. Publ. No. 2010-0317072-A1 | — | 2.5 | 0.6 | 2.4 | 51.1 | — | — | 27.3 |
| Y8406 | | PTA-10025 | 2.1 | 0.5 | 2.1 | 51.2 | — | — | 30.7 |
| Y8412 | | PTA-10026 | 2.0 | 0.5 | 1.9 | 55.8 | — | — | 27.0 |
| Y8647 | | — | 3.6 | 0.7 | 3.0 | 53.6 | — | — | 37.6 |
| Y8649 | | — | 2.4 | 0.6 | 2.1 | 55.8 | — | — | 27.9 |
| Y8650 | | — | 2.4 | 0.6 | 2.1 | 56.1 | — | — | 28.2 |
| Y9028 | | — | 2.5 | 0.8 | 1.9 | 54.5 | — | — | 39.6 |
| Y9031 | | — | 3.2 | 0.9 | 2.6 | 52.3 | — | — | 38.6 |
| Y9477 | | — | 3.7 | 1.0 | 2.1 | 61.4 | — | — | 32.6 |
| Y9497 | | — | 3.6 | 0.9 | 2.3 | 58.7 | — | — | 33.7 |
| Y9502 | | — | 3.3 | 0.8 | 2.4 | 57.0 | — | — | 37.1 |
| Y9508 | | — | 3.3 | 0.9 | 2.3 | 58.7 | — | — | 34.9 |
| Y8143 | | — | 1.6 | 0.6 | 1.6 | 50.3 | — | — | 22.3 |
| Y8145 | | — | 1.5 | 0.6 | 1.5 | 48.5 | — | — | 23.1 |
| Y8259 | | PTA-10027 | 1.7 | 0.6 | 1.6 | 53.9 | — | — | 20.5 |
| Y8367 | | — | 1.7 | 0.8 | 1.0 | 58.3 | — | — | 18.4 |
| Y8370 | | — | 1.9 | 0.6 | 1.5 | 56.4 | — | — | 23.3 |
| Y8670 | | — | 1.7 | 0.6 | 1.1 | 60.9 | — | — | 27.3 |
| Y8672 | | — | 1.6 | 0.7 | 1.1 | 61.8 | — | — | 26.5 |

Notes:
The term "total fatty acids" ("TFAs") refer to the sum of all cellular fatty acids that can be derivatized to fatty acid methyl esters ("FAMEs") by the base transesterification method (as known in the art) in a given sample, which may be the biomass or oil, for example. Thus, total fatty acids include fatty acids from neutral lipid fractions (including diacylglycerols, monoacylglycerols and triacylglycerols) and from polar lipid fractions but not free fatty acids. The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).
The term "total lipid content" of cells is a measure of TFAs as a percent of the dry cell weight ("DCW"), although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

One of skill in the art will appreciate that the methodology of the present invention is not limited to the *Y. lipolytica* strains described above. Instead, any recombinant oleaginous microorganism capable of producing PUFAs will be equally suitable for use as disclosed herein.

In some embodiments, it may be desirable for the recombinant oleaginous microorganism strain to be capable of "high-level production", wherein the microorganism can produce at least about 5-10% of the desired PUFA (i.e., LA, ALA, EDA, GLA, STA, ETrA, DGLA, ETA, ARA, DPA n-6, EPA, DPA n-3 and/or DHA) in the total lipids. More preferably, the *Y. lipolytica* will produce at least about 10-25% of the desired PUFA in the total lipids, more preferably at least about 25-35% of the desired PUFA in the total lipids, more preferably at least about 35-45% of the desired PUFA in the total lipids, more preferably at least about 45-55% of the desired PUFA in the total lipids, and most preferably at least about 55-65% of the desired PUFA in the total lipids. The structural form of the PUFA is not limiting; thus, for example, EPA may exist in the total lipids as free fatty acids or in esterified forms such as acylglycerols, phospholipids, sulfolipids or glycolipids.

Accordingly, it is expected that introduction of chimeric genes encoding a PUFA biosynthetic pathway, i.e., the delta-9 elongase/delta-8 desaturase pathway or the delta-6 desaturase/delta-6 elongase pathway described herein, or a portion thereof, under the control of the appropriate promoters will result in increased production of omega-3 and/or omega-6 fatty acids. It is contemplated that it will be useful to express various combinations of the PUFA desaturase and elongase genes together in a host microorganism. It will be obvious to one skilled in the art that the particular gene(s) included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and $C_{20/22}$ elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs where the fatty acid substrate is converted directly into the desired fatty acid product without any intermediate steps or pathway intermediates. For example, production of ARA would occur in a host cell which produces or which is provided DGLA, by adding or introducing into said cell an expression cassette that provides delta-5 desaturase activity.

Additionally, multiple genes encoding a PUFA biosynthetic pathway may be used in combination, such that a series of reactions occur to produce a desired PUFA. For example, expression cassette(s) encoding $C_{18/20}$ elongase, delta-5 desaturase, and delta-17 desaturase activities would enable a host cell that naturally produces GLA, to instead produce EPA (such that GLA is converted to DGLA by a $C_{18/20}$ elongase such as delta-6 elongase; DGLA may then be converted to ARA by a delta-5 desaturase; and ARA is then converted to EPA by a delta-17 desaturase). Addition of a $C_{20/22}$ elongase would convert EPA to DPA, and further addition of a delta-4 desaturase would convert DPA to DHA.

In one embodiment, the polyunsaturated fatty acids produced by the recombinant oleaginous microorganisms disclosed herein comprises an omega-3 polyunsaturated fatty acid selected from the group consisting of EPA, DPA and DHA. In a preferred embodiment, the produced omega-3 polyunsaturated fatty acid is EPA.

To construct the recombinant oleaginous microorganism of the present invention, it is necessary to create and introduce at least one genetic construct encoding a PUFA biosynthetic pathway and a caleosin polypeptide into a suitable host cell. Nucleotide sequences encoding one or more PUFA biosynthetic pathway enzymes and a caleosin polypeptide may be placed in multiple, separate constructs. One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Maniatis, Silhavy et al., and Ausubel et al., above.

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene(s). Typically, however, the vector, plasmid, or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from the genes native to the production host.

Transcriptional initiation control regions (also initiation control regions or promoters) useful to drive expression of desaturases and/or elongases, and caleosin polypeptide coding sequences in the desired microbial host cell are well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these coding sequences in the selected host cell is suitable, although transcriptional and translational regions from the host species are particularly useful. Expression in a host cell can be accomplished in an induced or constitutive fashion. Induced expression occurs by inducing the activity of a regulatable promoter operably linked to the gene of interest, while constitutive expression occurs by the use of a constitutive promoter. See for example U.S. Pat. Appl. Publ. No. 2006-0115881-A1 (incorporated herein by reference), corresponding to WO 2006/052870, for preferred transcriptional initiation regulatory regions for use in *Y. lipolytica*. Any one of a number of regulatory sequences can be used, depending upon whether constitutive or induced transcription is desired, the efficiency of the promoter in expressing the coding sequence of interest, the ease of construction and the like. Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The 3' non-coding sequences containing transcription termination regions may be provided in a recombinant construct and may be from the 3' region of the gene from which the initiation region was obtained or from a different gene. A large number of termination regions are known and function satisfactorily in a variety of hosts (when utilized both in the same and different genera and species from which they were derived). Termination regions may also be derived from various genes native to the preferred hosts. The termination region usually is selected more as a matter of convenience rather than because of any particular property. The 3'-region can also be synthetic, as one of skill in the art can utilize available information to design and synthesize a 3'-region sequence that functions as a transcription terminator. A termination site may be unnecessary, but is highly preferred.

Merely inserting a gene into a cloning vector does not ensure its expression at the desired rate, concentration, amount, etc. In response to the need for a high expression rate, many specialized expression vectors have been created by adjusting certain properties that govern transcription, RNA stability, translation, protein stability and location, and secretion from the host cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the final cellular location of the synthesized foreign protein; the efficiency of translation and correct folding of the protein in the host organism; the intrinsic stability of the mRNA and protein of the cloned gene within the host cell; and the codon usage within the cloned gene, such that its frequency approaches the frequency of preferred codon usage of the host cell. Each of these types of modifications is encompassed in the present invention, as means to further optimize expression of the PUFA biosynthetic pathway enzymes and the caleosin polypeptide.

After at least one genetic construct is created comprising at least one promoter, nucleic acid sequences encoding a functional PUFA biosynthetic pathway and a caleosin polypeptide, and at least one terminator, it is placed in a plasmid vector capable of autonomous replication in a host cell, or a DNA fragment(s) containing the chimeric genes is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the genes of interest may be introduced into a host cell by any standard technique. These techniques include transformation (e.g., lithium acetate transformation [*Methods in Enzymology*, 194:186-187 (1991)]), biolistic impact, electroporation, microinjection, or any other method that introduces the genes of interest into the host cell. More specific teachings applicable for oleaginous yeasts (e.g., *Y. lipolytica*) include U.S. Pat. No. 4,880,741 and U.S. Pat. No. 5,071,764 and Chen, D. C. et al. (*Appl Microbiol Biotechnol.* 48(2):232-235 (1997)), which are incorporated herein by reference.

For convenience, a host cell that has been manipulated by any method to take up a DNA sequence, for example, in an expression cassette, will be referred to as "transformed", "transformant" or "recombinant" herein. The transformed host will have at least one copy of the expression construct and may have two or more, depending upon whether the expression cassette is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. Nos. 7,238,482, 7,259,255 and WO 2006/052870.

Following transformation, substrates suitable for the recombinantly expressed desaturases and/or elongases (and optionally other PUFA enzymes that are expressed within the host cell) may be produced by the host either naturally or transgenically (i.e., the substrates are endogenous), or they may be provided exogenously.

The transformed host cell is grown under conditions that optimize expression of chimeric genes (e.g., encoding desaturases, elongases, etc.) and produce the greatest and the most economical yield of the preferred PUFAs. In general, media conditions that may be optimized include: the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Oleaginous yeast may be grown in a complex medium (e.g., yeast extract-peptone-dextrose broth (YPD)) or a defined minimal medium that lacks a component necessary for growth and thereby forces selection of the desired expression cassettes (e.g., Yeast Nitrogen Base (DIFCO Laboratories, Detroit, Mich.)).

Fermentation media for the methods and host cells described herein contain a suitable carbon source, such as are taught in U.S. Pat. No. 7,238,482 and U.S. Pat. Appl. Publ. No. 2011-0059204 A1. Although it is contemplated that the source of carbon utilized in the present invention may encompass a wide variety of carbon-containing sources, preferred carbon sources are sugars, glycerol and/or fatty acids. Most preferred is/are glucose, sucrose, invert sucrose, fructose and/or fatty acids containing between 10-22 carbons.

Nitrogen may be supplied from an inorganic (e.g., $(NH_4)_2SO_4$) or organic (e.g., urea, glutamate, or yeast extract) source. In addition to sucrose and nitrogen sources, the fermentation medium also contains suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara et al., *Ind. Appl. Single Cell Oils*, Kyle and Colin, eds. pp. 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage fermentation process, since the metabolic state must be "balanced" between growth and synthesis/storage of fats. Thus, most preferably, a two-stage fermentation process is employed for the production of PUFAs in oleaginous yeast. This process is described in U.S. Pat. No. 7,238,482, as are various suitable fermentation process designs (i.e., batch, fed-batch and continuous) and considerations during growth.

In some aspects herein, the primary product is oleaginous yeast biomass. As such, isolation and purification of the PUFA-containing oils from the biomass may not be necessary (i.e., wherein the whole cell biomass is the product).

However, certain end uses and/or product forms may require partial and/or complete isolation/purification of the PUFA-containing oil from the biomass, to result in partially purified biomass, purified oil, and/or purified PUFA(s). The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Jacobs (*Critical Reviews in Biotechnology* 12(5/6):463-491 (1992)). A brief review of downstream processing is also provided by Singh and Ward (*Adv. Appl. Microbiol.*, 45:271-312 (1997)).

In general, methods for the recovery and purification of PUFAs from microbial biomass may include extraction (e.g., U.S. Pat. Nos. 6,797,303 and 5,648,564) with organic solvents, sonication, supercritical fluid extraction (e.g., using carbon dioxide), saponification and physical means such as presses, bead beaters, or combinations thereof. One is referred to the teachings of U.S. Pat. No. 7,238,482 for additional details.

The recombinant oleaginous microorganisms comprising one or more genetic constructs encoding a caleosin polypeptide and one or more enzymes of a functional PUFA biosynthetic pathway contain a greater quantity of oil when compared to the quantity of oil contained in a corresponding control recombinant oleaginous microorganism not comprising the at least one genetic construct encoding a caleosin polypeptide or that comprises but does not express the at least one genetic construct encoding a caleosin polypeptide. The quantity of oil contained in the recombinant oleaginous microorganisms can be the total lipid content measured as total fatty acids as a percent of dry cell weight.

There are a plethora of food and feed products incorporating omega-3 and/or omega-6 fatty acids, particularly e.g., ALA, GLA, ARA, EPA, DPA and DHA. It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils containing omega-3 and/or omega-6 fatty acids will be suitable for use in a variety of food and feed products including, but not limited to: food analogs, meat products, cereal products, baked foods, snack foods and dairy products (see U.S. Pat. Appl. Publ. No. 2006-0094092 for details). The feed products also include those for animal uses.

These compositions may be used in formulations to impart health benefit in medical foods including medical nutritionals, dietary supplements, infant formula and pharmaceuticals. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

In another embodiment, a method for increasing the amount of oil comprising at least one polyunsaturated fatty acid contained in a recombinant oleaginous microorganism is provided. The method comprises the steps of (a) providing a recombinant oleaginous microorganism as disclosed herein; and (b) growing the recombinant oleaginous microorganism under conditions whereby oil comprising at least one polyunsaturated fatty acid is produced. The recombinant oleaginous microorganism of the invention contains a greater quantity of oil when compared to the quantity of oil contained in a recombinant oleaginous microorganism not comprising the at least one genetic construct encoding said caleosin polypeptide.

EXAMPLES

The present invention is further defined in the following Examples. It should be understood that these Examples, while indicating preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, $5^{th}$ Ed. Current Protocols, John Wiley and Sons, Inc., N.Y., 2002.

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds.), American Society for Microbiology: Washington, D.C. (1994)); or in *Manual of Industrial Microbiology and Biotechnology*, $3^{rd}$ Edition (Richard H. Baltz, Julian E. Davies, and Arnold L. Demain Eds.), ASM Press, Washington, D.C., 2010.

All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St. Louis, Mo.), unless otherwise specified.

General molecular cloning was performed according to standard methods (Sambrook et al., above). Unless otherwise indicated herein comparisons of genetic sequences were accomplished using DNASTAR software (DNASTAR Inc., Madison, Wis.).

The structure of an expression cassette will be represented by a simple notation system of "X::Y::Z", wherein X describes the promoter fragment, Y describes the gene fragment, and Z describes the terminator fragment, which are all operably linked to one another.

*Yarrowia lipolytica* Strains Containing a Functional Polyunsaturated Fatty Acid Biosynthetic Pathway—Strains Y4184, Y4184U, Y9502, Y9502U, Z1978, Z1978U, Z5567 and Z5567U

*Yarrowia lipolytica* Y4184 was derived from *Yarrowia lipolytica* ATCC #20362 as described in Example 7 of Int'l Appl. Publ. No. WO 2008/073367, which is incorporated herein by reference. Strain Y4184 was capable of producing about 31% EPA relative to the total lipids via expression of a delta-9 elongase/delta-8 desaturase pathway.

*Yarrowia lipolytica* Y4184U, having an Ura3⁻ phenotype compared to strain Y4184, was also described in Example 7 of Int'l Appl. Publ. No. WO 2008/073367.

The generation of strain Y9502 is described in U.S. Pat. Appl. Publ. No. 2010-0317072-A1, which is incorporated herein by reference. Strain Y9502, derived from *Yarrowia lipolytica* ATCC #20362, was capable of producing about 57.0% EPA relative to the total lipids via expression of a delta-9 elongase/delta-8 desaturase pathway.

The generation of strain Y9502U, having a Ura3⁻ phenotype compared to strain Y9502, was described in U.S. Pat. Appl. Publ. No. 2012-0052537 A1 (herein incorporated by reference).

The development of strain Z1978 from strain Y9502 is described in U.S Pat. Appl. Publ. No. 2012-0052537 A1 (above). The development of strain Z1978U, having a Ura3⁻ phenotype compared to strain Z1978, was also described in U.S. Pat. Appl. Publ. No. 2012-0052537 A1.

The development of strain Z5567 from strain Z1978 is described in U.S Pat. Appl. Publ. No. 2012-0052537 A1 (above). The development of strain Z5567U, having a Ura3⁻ phenotype compared to strain Z5567, was also described in U.S. Pat. Appl. Publ. No. 2012-0052537 A1.

Transformation and Cultivation of *Yarrowia lipolytica*

*Yarrowia lipolytica* strains were routinely grown at 30° C. in several media, according to the recipes shown below.

High Glucose Medium ["HGM"] (per liter): 80 g glucose, 2.58 g $KH_2PO_4$ and 5.36 g $K_2HPO_4$, pH 7.5 (do not need to adjust).

Synthetic Dextrose Medium ["SD"] (per liter): 6.7 g yeast nitrogen base with ammonium sulfate and without amino acids; and 20 g glucose.

Fermentation medium ["FM"] (per liter): 6.7 g yeast nitrogen base with ammonium sulfate and without amino acids, 6.0 g $KH_2PO_4$, 2.0 g $K_2HPO_4$, 1.5 g $MgSO_4 \cdot 7H_2O$, 20 g glucose, and 5.0 g yeast extract (BBL, BD Diagnostic Systems, Sparks, Md.).

The Y4184 strains were grown in SD medium for 2 days, followed by growth in HGM for 5 days. The Y9502 and Z1978 strains were grown in FM for 2 days, followed by growth in HGM for 5 days.

Transformation of *Y. lipolytica* was performed as described in U.S. Pat. Appl. Publ. No. 2009-0093543-A1, which is incorporated herein by reference. In general, for transformation of Ura3⁻ cells, cells were transfected with a plasmid or fragment thereof carrying a URA3 gene, and then selected for transformation on plates lacking uracil.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I., *Arch Biochem Biophys.*, 276 (1):38-46 (1990)) and subsequently analyzed with an Agilent Technologies 6890N gas chromatograph fitted with a 30-m× 0.25 mm (i.d.) SUPELCO Omegawax320 (Agilent Technologies) column. The oven temperature was ramped from 160° C. to 240° C. at 30° C./min and then held for 3.8 min at 240° C.

For direct base transesterification, a *Yarrowia* culture (1 mL) was harvested by centrifugation (13,000×g) for 1 min. Sodium methoxide (500 µL of a 1% solution) was added to the sample, and then the sample was vortexed and rocked for 45 min. Then, 100 µL of 1.0 M NaCl and 500 µL of hexane were added, and the sample was vortexed and spun. The upper layer was removed and analyzed by gas chromatography as described above.

Analysis of Total Lipid Content and Composition in *Yarrowia lipolytica* under Comparable Oleaginous Conditions For a detailed analysis of the total lipid content and composition in a particular strain of *Yarrowia lipolytica*, flask assays were conducted as follows. Specifically, cultures were grown at a starting $OD_{600}$ of ~0.3 in 25 mL of SD medium in a 125 mL flask for 48 h. The cells were harvested by centrifugation for 5 min at 4300 rpm in a 50 mL conical tube. The supernatant was discarded and the cells were resuspended in 25 mL of HGM in another 125 mL flask. After 5 days in a shaker incubator at 250 rpm and 30° C., a 1 mL aliquot was used for fatty acid analysis (as described above) following centrifugation for 1 min at 13,000 rpm, and a 5 mL aliquot was dried for dry cell weight (DCW) determination.

For DCW determination, 5 mL culture was harvested by centrifugation for 5 min at 4300 rpm. The pellet was resuspended in 10 mL of sterile water and re-harvested as above. The washed pellet was re-suspended in 1 mL of water (three times) and transferred to a pre-weighed aluminum pan. The cell suspension was dried overnight in a vacuum oven at 80° C. The weight of the cells was determined (g/L).

Total lipid content of cells ["TFAs % DCW"] was calculated and considered in conjunction with data tabulating the concentration of each fatty acid as a weight percent of TFAs ["% TFAs"] and the EPA content as a percent of the dry cell weight ["EPA % DCW"], when EPA was produced. Data from flask assays are presented in table format summarizing the total DCW of the cells, the total lipid content of cells ["TFAs % DCW"], the concentration of each fatty acid as a weight percent of TFAs ["% TFAs"] and the EPA content as a percent of the dry cell weight ["EPA % DCW"]. More specifically, fatty acids are identified as 18:0 (stearic acid), 18:1 (oleic acid), 18:2 (LA), and 20:5 (EPA).

Example 1

Recombinant *Yarrowia lipolytica* Containing a Functional Polyunsaturated Fatty Acid Biosynthetic Pathway and the Codon-Optimized *Arabidopsis thaliana* Caleosin AtClo1s Coding Sequence—Strain Y4184U+AtClo1s This Example describes the construction of overexpression construct pYRH55 (FIG. 1; SEQ ID NO:43), and *Y. lipolytica* strain Y4184U+AtClo1s.

The AtClo1 gene (also referred to as ATS1 or At4g26740) is found in *Arabidopsis thaliana* seed lipid bodies, and belongs to a multigene family (Naested et al. (2000), *Plant Mol. Biol.* 44:463-476). The codon usage of the AtClo1 gene of *Arabidopsis thaliana* (coding sequence set forth in SEQ ID NO:1) was optimized for expression in *Yarrowia lipolytica* in a manner similar to that described in Int'l Appl. Publ. No. WO 2004/101753 and U.S. Pat. No. 7,125,672. Specifically, a codon-optimized AtClo1 coding sequence (designated "AtClo1s", SEQ ID NO:33) was designed based on the coding sequence of the AtClo1 gene (SEQ ID NO:1), according to the *Yarrowia* codon usage pattern (Int'l Appl. Publ. No. WO 2004/101753), the consensus sequence around the 'ATG' translation initiation codon, and the general rules of RNA stability (Guhaniyogi and Brewer, *Gene* 265(1-2):11-23 (2001)). In addition to modification of the translation initiation site, 173 bp of the 738 bp coding region were modified (23.4%; and 153 codons were optimized (62%). The GC content was increased from 45.4% within the wild type gene (i.e., AtClo1) to 54.4% within the synthetic gene (i.e., AtClo1s). NcoI and NotI sites were incorporated around the translation initiation codon and after the stop codon of AtClo1s, respectively. None of the modifications in the codon-optimized sequence changed the amino acid sequence of the encoded protein (SEQ ID NO:2); i.e., both the AtClo1 coding sequence (SEQ ID NO:1) and the AtClo1s coding sequence (SEQ ID NO:33) encode SEQ ID NO:2. The designed AtClo1s coding sequence (SEQ ID NO:33) was synthesized by GenScript Corporation (Piscataway, N.J.) and supplied as pUC57-AtClo1s.

Construction of pYRH55: Plasmid pYRH55 (FIG. 1, SEQ ID NO:43) was constructed to overexpress the *Y. lipolytica* codon-optimized AtClo1s coding sequence (SEQ ID NO:33). Plasmid pYRH55 was derived from plasmid pZuFmEaD5s (described in Example 6 of U.S. Pat. Appl. Publ. No. 2008-0274521-A1, incorporated herein by reference). Plasmid pZuFmEaD5s contained a chimeric FBAINm::EaD5S::PEX20 gene, wherein FBAINm is a *Y. lipolytica* promoter (U.S. Pat. No. 7,202,356), EaD5S is a synthetic delta-5 desaturase derived from *Euglena anabaena* and codon-optimized for expression in *Y. lipolytica*, flanked by NcoI/NotI restriction enzyme sites, and PEX20 is a terminator sequence from the *Yarrowia* PEX20 gene (GenBank Accession No. AF054613).

The codon-optimized AtClo1s coding sequence of pUC57-AtClo1s was digested with NcoI/NotI and the resulting fragment was used to replace the NcoI/NotI fragment of pZuFmEaD5s to produce pYRH55 (FIG. 1), containing a chimeric FBAINm::AtClo1s::PEX20 gene.

Generation of *Y. lipolytica* Strain Y4184U+AtClo1s: To overexpress AtClo1s in *Y. lipolytica* strain Y4184U, pYRH55 was cut with BsiWI/PacI and a 3.5 kB fragment was isolated and used for transformation (as described in General Methods), thereby producing strain Y4184U+AtClo1s.

Example 2

Recombinant *Y. lipolytica* Containing a Functional Polyunsaturated Fatty Acid Biosynthetic Pathway and the Codon-Optimized *Arabidopsis thaliana* Caleosin AtClo1s Coding Sequence—Strain Y9502U+AtClo1s This Example describes the construction of *Y. lipolytica* strain Y9502U+AtClo1s containing the overexpression plasmid pYRH55.

To overexpress AtClo1s in *Yarrowia lipolytica* strain Y9502U, plasmid pYRH55, described in Example 1, was digested with BsiWI/PacI and a 3.5 kB fragment was isolated and used for transformation of Y9502U (as described in General Methods), thereby producing strain Y9502U+AtClo1s.

Example 3

Recombinant *Yarrowia lipolytica* Containing a Functional Polyunsaturated Fatty Acid Biosynthetic Pathway and the Codon-Optimized *Arabidopsis thaliana* Caleosin AtClo1s Coding Sequence—Strain Z1978U+AtClo1s This Example describes the construction of *Y. lipolytica* strain Z1978U+AtClo1s containing the overexpression plasmid pYRH55.

To overexpress AtClo1s in *Y. lipolytica* strain Z1978U, plasmid pYRH55, described in Example 1, was digested with BsiWI/PacI and a 3.5 kB fragment was isolated and used for the transformation (as described in General Methods), thereby producing strain Z1978U+AtClo1s.

Example 4

Oil Production by Strain Y4184U+AtClo1s

In this Example, the effect of AtClo1s overexpression in strain Y4184U+AtClo1s on accumulated oil level was determined and compared to the oil level obtained with the parent strain, which lacks AtClo1s expression. AtClo1s overexpression resulted in increased oil/total lipid content (measured as percent of the total dry cell weight [TFAs % DCW]) compared to cells lacking AtClo1s expression.

To evaluate and compare the effect of AtClo1s overexpression in *Y. lipolytica* on the quantity of oil and fatty acid (FA) composition, strain Y4184 (control) and strain Y4184U+AtClo1s were grown under comparable oleaginous conditions, as described in the General Methods.

The DCW, total lipid content of cells [TFAs % DCW] and the concentration of each fatty acid as a weight percent of TFAs [% TFAs] for *Y. lipolytica* Y4184 control and Y4184U+AtClo1s strains were determined as described in the General Methods. The results are shown in Table 4.

TABLE 4

Lipid Content and Composition in *Y. lipolytica* Strains Y4184 and Y4184U + AtClo1s

| Strain | DCW (g/L) | TFAs % DCW | % TFAs | | | | EPA % DCW |
|---|---|---|---|---|---|---|---|
| | | | 18:0 | 18:1 | 18:2 | EPA | |
| Y4184 | 5.00 | 16 | 1.9 | 9.4 | 29.9 | 25.7 | 4.1 |
| | 4.46 | 17 | 1.6 | 8.3 | 31.2 | 26.7 | 4.6 |
| AVG | 4.73 | 17 | 1.8 | 8.9 | 30.6 | 26.2 | 4.4 |
| Y4184U + AtClo1s | 3.46 | 19 | 1.8 | 7.4 | 29.7 | 26.7 | 5.1 |
| | 3.38 | 23 | 1.6 | 8.2 | 31.0 | 24.7 | 5.7 |
| | 3.08 | 26 | 2.1 | 8.5 | 26.8 | 26.0 | 6.7 |
| | 3.74 | 19 | 1.8 | 8.5 | 29.2 | 26.4 | 5.0 |
| | 3.64 | 18 | 1.6 | 7.1 | 28.1 | 28.7 | 5.1 |
| | 2.78 | 22 | 2.2 | 8.0 | 26.2 | 28.1 | 6.3 |
| | 3.60 | 19 | 1.9 | 7.4 | 28.9 | 27.7 | 5.3 |
| | 3.90 | 20 | 1.7 | 8.0 | 29.4 | 27.1 | 5.4 |
| AVG | 3.45 | 21 | 1.8 | 7.9 | 28.7 | 26.9 | 5.6 |

The results in Table 4 show that overexpression of AtClo1s in Y4184U increased the quantity of oil measured as total lipid content [TFAs % DCW] by approximately 24% over the total lipid content of control strain Y4184. Also, AtClo1s overexpression in Y4184U increased the average EPA titer [EPA % DCW] by approximately 27% compared to the EPA titer of Y4184.

Therefore, overexpression of a caleosin polypeptide can increase the oil content of a recombinant microorganism comprising a polyunsaturated fatty acid biosynthetic pathway. In this particular example, caleosin overexpression increased oil content in a recombinant *Yarrowia* strain (Y4184) that, without caleosin overexpression, accumulated oil to about 17% on a dry cell weight basis (TFAs % DCW, Table 4). The ability of caleosin overexpression to raise oil content in this context suggests that overexpressing caleosin in a recombinant *Yarrowia* having a higher oil content (e.g., at least 25 TFAs % DCW) would also raise oil content.

Example 5

Oil Production by Strain Y9502+AtClo1s

The effect of AtClo1 s overexpression in strain Y9502U+AtClo1 s on accumulated oil level was determined and compared to the oil level obtained with the parent strain, which lacks AtClo1 s expression. AtClo1 s overexpression resulted in increased oil/total lipid content (measured as percent of the total dry cell weight [TFAs % DCW]) compared to cells lacking AtClo1 s expression.

To evaluate and compare the effect of AtClo1s overexpression in *Y. lipolytica* on the quantity of oil and FA composition, strain Y9502 (control) and strain Y9502U+AtClo1s were grown under comparable oleaginous conditions, as described in the General Methods.

The DCW, total lipid content of cells [TFAs % DCW] and the concentration of each fatty acid as a weight percent of TFAs [% TFAs] for *Y. lipolytica* Y9502 control and Y9502U+AtClo1S strains were determined as described in the General Methods. The results are shown in Table 5.

TABLE 5

Lipid Content and Composition in *Y. lipolytica* Strains Y9502 and Y9502U + AtClo1s

| Strain | DCW (g/L) | TFAs % DCW | % TFAs 18:0 | 18:1 | 18:2 | EPA | EPA % DCW |
|---|---|---|---|---|---|---|---|
| Y9502 | 3.4 | 34.4 | 2.2 | 4.9 | 12.9 | 57.6 | 19.8 |
|  | 3.4 | 34.5 | 2.3 | 4.9 | 12.9 | 57.3 | 19.8 |
| AVG | 3.4 | 34.5 | 2.3 | 4.9 | 12.9 | 57.5 | 19.8 |
| Y9502U + AtClo1s | 3.8 | 38.3 | 1.9 | 5.6 | 14.0 | 53.7 | 20.6 |
|  | 3.9 | 39.7 | 1.9 | 5.8 | 14.1 | 53.2 | 21.1 |
|  | 3.9 | 38.4 | 2.0 | 5.8 | 14.1 | 53.5 | 20.5 |
|  | 4.0 | 37.9 | 2.0 | 5.9 | 14.4 | 54.2 | 20.5 |
|  | 4.0 | 43.1 | 2.2 | 6.4 | 15.4 | 51.3 | 22.1 |
|  | 4.0 | 43.5 | 2.2 | 6.5 | 15.4 | 51.3 | 22.3 |
| AVG | 3.9 | 40.1 | 2.0 | 6.0 | 14.6 | 52.9 | 21.2 |

The results in Table 5 show that overexpression of AtClo1 s in Y9502U increased the quantity of oil measured as total lipid content [TFAs % DCW] by approximately 16% over the total lipid content of control strain Y9502. Also, AtClo1s overexpression in Y9502U increased the average EPA titer [EPA % DCW] by approximately 7% compared to the EPA titer of Y9502.

Thus, caleosin overexpression increased oil content in a recombinant oleaginous *Yarrowia* strain (Y9502U) that, without caleosin overexpression, accumulated oil to about 34.5% on a dry cell weight basis (TFAs % DCW, Table 5). Therefore, overexpression of a caleosin polypeptide can increase the oil content of a recombinant oleaginous microorganism that comprises a polyunsaturated fatty acid biosynthetic pathway and that produces at least 25% of its dry cell weight as oil.

Example 6

Oil Production by Strain Z1978U+AtClo1s

The effect of AtClo1s overexpression in strain Z1978U+AtClo1s on accumulated oil level was determined and compared to the oil level obtained with the parent strain, which lacks AtClo1s expression. AtClo1s overexpression resulted in increased oil/total lipid content (measured as percent of the total dry cell weight [TFAs % DCW]) compared to cells lacking AtClo1s expression.

To evaluate and compare the effect of the AtClo1s overexpression in *Y. lipolytica* on the quantity of oil and FA composition, strain Z1978 (control) and strain Z1978U+AtClo1s were grown under comparable oleaginous conditions, as described in the General Methods.

The DCW, total lipid content of cells [TFAs % DCW] and the concentration of each fatty acid as a weight percent of TFAs [% TFAs] for *Y. lipolytica* Z1978 control and Z1978U+AtClo1s strains were determined as described in General Methods. Control strain Z1978 was assayed in duplicate, and two isolates were tested for the strain Z1978U+AtClo1s in triplicate, and the average of the triplicate determinations is shown in Table 6.

TABLE 6

Lipid Content and Composition in *Y. lipolytica* Strains Z1978 and Z1978U + AtClo1s

| Strain | DCW (g/L) | TFAs % DCW | % TFAs 18:0 | 18:1 | 18:2 | EPA | EPA % DCW |
|---|---|---|---|---|---|---|---|
| Z1978 | 4.44 | 36.0 | 1.8 | 5.0 | 10.5 | 53.4 | 19.2 |
|  | 4.50 | 36.3 | 1.8 | 5.2 | 10.9 | 55.0 | 19.9 |
| AVG | 4.47 | 36.2 | 1.8 | 5.1 | 10.7 | 54.2 | 19.6 |
| Z1978U + AtClo1s | 4.43 | 38.8 | 1.8 | 5.5 | 13.5 | 47.8 | 18.5 |
|  | 4.19 | 37.3 | 2.7 | 5.1 | 11.5 | 50.5 | 18.8 |
| AVG | 4.32 | 38.1 | 2.2 | 5.2 | 12.0 | 50.4 | 18.6 |

The results in Table 6 show that overexpression of AtClo1s in Z1978U increased the quantity of oil measured as total lipid content [TFAs % DCW] by approximately 5%. Thus, this also shows that caleosin overexpression can increase the oil content of a recombinant oleaginous microorganism that comprises a polyunsaturated fatty acid biosynthetic pathway and that produces at least 25% of its dry cell weight as oil.

Example 7

Recombinant *Yarrowia lipolytica* Containing a Functional Polyunsaturated Fatty Acid Biosynthetic Pathway and a Codon-Optimized Caleosin Coding Sequence—Strain Y9502U+Cal01s, Y9502U+Cal02s, Y9502U+Cal03s, Y9502U+Cal04s, Y9502U+Cal05s and Y9502U+Cal06s The present Example describes the construction of overexpression constructs pYRH84 (SEQ ID NO:44), pYRH85 (SEQ ID NO:45), pYRH86 (SEQ ID NO:46), pYRH88 (SEQ ID NO:47), pYRH89 (SEQ ID NO:48), and pYRH90 (SEQ ID NO:49), and *Y. lipolytica* strains Y9502U+Cal01s, Y9502U+Cal02s, Y9502U+Cal03s, Y9502U+Cal04s, Y9502U+Cal05s and Y9502U+Cal06s.

Sequences for six different caleosin proteins from *Ricinus communis* (Gen Bank Acc. No. XP_002528367), *Glycine max* (GenBank Acc. No. AAB71227), *Sesamum indicum* (GenBank Acc. No. AAF13743), *Coix lacryma* (Gen Bank Acc. No. ACP27620), *Aspergillus niger* (GenBank Acc. No. XP_001397384) and *Neurospora crassa* (GenBank Acc. No. XP_958990) were codon-optimized for expression in *Yarrowia lipolytica* (designated "Cal01s" [SEQ ID NO:4], "Cal02s" [SEQ ID NO:6], "Cal03s" [SEQ ID NO:8], "Cal04s" [SEQ ID NO:38], "Cal05s" [SEQ ID NO:40] and "Cal06s" [SEQ ID NO:42], respectively), in a manner similar to that described in Example 1 and Int'l. Appl. Publ. No. WO2004/101753 (above) and U.S. Pat. No. 7,125,672 (above). Specifically, each codon-optimized caleosin coding sequence was designed based on the coding sequence of the corresponding wild type caleosin-encoding gene (SEQ ID NO:3, 5, 7, 9, 11, or 13), according to the *Yarrowia* codon usage pattern (Int'l. Appl. Publ. No. WO2004/101753), the consensus sequence around the 'ATG' translation initiation codon, and the general rules of RNA stability (Guhaniyogi and Brewer, 2001, *Gene* 265(1-2):11-23).

In addition to modifying the translation initiation site, for Cal01s, 167 bp of the 702 bp coding region were modified (23.8%) and 150 codons were optimized (64%) for *Yarrowia* expression. The GC content was increased from 44.6% within the wild type gene to 54.8% within the synthetic gene. For Cal02s, 182 bp of the 720 bp coding region were modified (25.3%) and 160 codons were optimized (67%). The GC content was increased from 42.5% within the wild type gene to 54.2% within the synthetic gene. For Cal03s, 175 bp of the 738 bp coding region were modified (23.7%) and 157 codons were optimized (64%). The GC content was increased from 49.2% within the wild type gene to 54.9% within the synthetic gene. For Cal04s, 187 bp of the 954 bp coding region were modified (19.6%) and 165 codons were optimized (52%). The GC content was decreased from 66.5% within the wild type gene to 57.3% within the synthetic gene. For Cal05s, 190 bp of the 849 bp coding region were modified (22.4%) and 174 codons were optimized (61%). The GC content was slightly changed from 54.0% within the wild type gene to 55.2% within the synthetic gene. For Cal06s, 182 bp of the 900 bp coding region were modified (20.2%) and 157 codons were optimized (52%). The GC content was decreased from 57.8% within the wild type gene to 54.3% within the synthetic gene.

NcoI and NotI sites were incorporated, respectively, around the translation initiation codon and after the stop codon of each of the synthesized genes. Due to the introduction of the enzyme sites, the Cal04s polypeptide (SEQ ID NO:38) has Q2E (glutamine to glutamate change at amino acid position 2), the Cal05s polypeptide (SEQ ID NO:40) has P2A (proline to alanine change at amino acid position 2), and the Cal06s polypeptide (SEQ ID NO:42) has P2A (proline to alanine change at amino acid position 2) relative to the respective wild type protein amino acid sequence. Except for these changes, no other modifications in the codon-optimized sequences changed the amino acid sequences of the encoded proteins. Both the Cal01 coding sequence (SEQ ID NO:3) and the Cal01s coding sequence (SEQ ID NO:34) encode SEQ ID NO:4, both the Cal02 coding sequence (SEQ ID NO:5) and the Cal02s coding sequence (SEQ ID NO:35) encode SEQ ID NO:6, and both the Cal03 coding sequence (SEQ ID NO:7) and the Cal03s coding sequence (SEQ ID NO:36) encode SEQ ID NO:8.

The designed Cal01s, Cal02s, Cal03s, Cal04s, Cal05s and Cal06s coding sequences (SEQ ID NOs:34, 35, 36, 37, 39 and 41, respectively) with the added NcoI and NotI sites were synthesized by GenScript Corporation (Piscataway, N.J.). Note that the NcoI and NotI sites are not shown in SEQ ID NOs:34, 35, 36, 37, 39 and 41.

Construction of Caleosin Overexpression Plasmids: Plasmids for codon-optimized caleosin overexpression were derived from pYRH55 (FIG. 1, SEQ ID NO:43). The codon-optimized caleosin coding sequences of *Ricinus communis*, *Glycine max*, *Sesamum indicum*, *Coix lacryma*, *Aspergillus niger* and *Neurospora crassa* prepared above were digested with NcoI/NotI. The resulting fragment was used to replace the NcoI/NotI fragment (i.e., AtClo1s insert) released from pYRH55. The resulting constructs, pYRH84 (SEQ ID NO:44), pYRH85 (SEQ ID NO:45), pYRH86 (SEQ ID NO:46), pYRH88 (SEQ ID NO:47), pYRH89 (SEQ ID NO:48) and pYRH90 (SEQ ID NO:49), contained a chimeric gene having the Cal01s, Cal02s, Cal03s, Cal04s, Cal05s, or Cal06s coding sequence, respectively, along with the FBAINm promoter (above) and the PEX20 terminator (above). Thus, pYRH55, pYRH84, pYRH85, pYRH86, pYRH88, pYRH89 and pYRH90 only differ from each other with respect to the particular codon-optimized caleosin coding sequence contained in each construct.

Generation of *Y. lipolytica* Strains Y9502U+Cal01s, Y9502U+Cal02s, Y9502U+Cal03s, Y9502U+Cal04s, Y9502U+Cal05s, and Y9502U+Cal06s: To overexpress a particular caleosin in *Y. lipolytica* strain Y9502U, plasmid constructs pYRH84, pYRH85, pYRH86, pYRH88, pYRH89 and pYRH90 were each individually digested with AscI/SphI and the larger fragment (of the two fragments resulting from each digestion) was used for transformation (as described in General Methods), thereby producing strains Y9502U+Cal01s, Y9502U+Cal02s, Y9502U+Cal03s, Y9502U+Cal04s, Y9502U+Cal05s and Y9502U+Cal06s, respectively.

Example 8

Oil Production by Strains Y9502U+Cal01s, Y9502U+Cal02s, Y9502U+Cal03s, Y9502U+Cal04s, Y9502U+Cal05s and Y9502U+Cal06s The effect of caleosin overexpression on oil accumulation in strains Y9502U+Cal01s, Y9502U+Cal02s, Y9502U+Cal03s, Y9502U+Cal04s, Y9502U+Cal05s and Y9502U+Cal06s was determined as described hereinbelow. Overexpression of caleosins from various sources resulted in increased oil/total lipid content (measured as percent of the total dry cell weight [TFAs % DCW]) compared to cells lacking caleosin expression.

To evaluate and compare the effect of caleosin overexpression in *Y. lipolytica* on the quantity of oil and FA composition, strain Y9502 (control) and strains Y9502U+Cal01s, Y9502U+Cal02s, Y9502U+Cal03s, Y9502U+Cal04s, Y9502U+Cal05s and Y9502U+Cal06s were grown under comparable oleaginous conditions, as described in the General Methods.

The DCW, total lipid content of cells [TFAs % DCW] and the concentration of each fatty acid as a weight percent of TFAs [% TFAs] for *Y. lipolytica* Y9502 control and strains Y9502U+Cal01s, Y9502U+Cal02s, Y9502U+Cal03s, Y9502U+Cal04s, Y9502U+Cal05s and Y9502U+Cal06s were determined as described in General Methods. The results are shown in Table 7. Three transformants for each caleosin overexpression strain were chosen for lipid measurement; the values in Table 7 are an average of two independent experiments of the three transformants for each strain. For control strain Y9502, the values represent an average of four independent experiments, each analyzed in duplicate.

TABLE 7

Lipid Content and Composition in *Y. lipolytica* Strains Y9502 and Y9502U + Cal01s, Y9502U + Cal02s, Y9502U + Cal03s, Y9502U + Cal04s, Y9502U + Cal05s and Y9502U + Cal06s

| Strain | DCW (g/L) | TFAs % DCW | EPA % TFAs | EPA % DCW |
|---|---|---|---|---|
| Y9502 | 3.46 | 31 | 55.2 | 17.1 |
| Y9502U + Cal01s | 4.14 | 34 | 54.6 | 18.6 |
| Y9502U + Cal02s | 4.25 | 33 | 54.7 | 18.0 |
| Y9502U + Cal03s | 3.80 | 34 | 54.3 | 18.4 |

TABLE 7-continued

Lipid Content and Composition in *Y. lipolytica* Strains Y9502 and
Y9502U + Cal01s, Y9502U + Cal02s, Y9502U + Cal03s,
Y9502U + Cal04s, Y9502U + Cal05s and Y9502U + Cal06s

| Strain | DCW (g/L) | TFAs % DCW | EPA % TFAs | EPA % DCW |
|---|---|---|---|---|
| Y9502U + Cal04s | 3.71 | 33 | 54.2 | 17.6 |
| Y9502U + Cal05s | 3.25 | 36 | 54.3 | 19.3 |
| Y9502U + Cal06s | 3.15 | 36 | 54.4 | 19.3 |

The results in Table 7 show that overexpression of caleosins in Y9502U increased the quantity of oil measured as total lipid content [TFAs % DCW] by up to 16% without significantly decreasing the level of EPA in the fatty acids [EPA % TFAs]. Thus, the average EPA titer [EPA % DCW] was increased by up to 13%, compared to that of control strain Y9502.

Thus, overexpression of various other caleosins aside from AtClo1s increased oil content in a recombinant oleaginous *Yarrowia* strain (Y9502) that, without caleosin overexpression, accumulated oil to about 31% on a dry cell weight basis (TFAs % DCW, Table 7). These results further indicate that overexpression of a caleosin polypeptide can increase the oil content of a recombinant oleaginous microorganism that comprises a polyunsaturated fatty acid biosynthetic pathway and that produces at least 25% of its dry cell weight as oil. Furthermore, these results indicate that caleosin proteins in general (i.e., not just one caleosin from a particular source) can be used to increase oil content in a recombinant oleaginous microorganism.

Example 9

Codon-Optimized AtClo1 Sequence with Multiple Cysteine Residues (Cys-AtClo1s) and Linking to PDAT or LPCAT Construction of overexpression constructs pYRH95 (SEQ ID NO:61), pYRH96 (SEQ ID NO:62), pYRH97 (SEQ ID NO:63), pYRH98 (SEQ ID NO:64) and pYRH99 (SEQ ID NO:65) is described. Also described is the preparation of *Y. lipolytica* strains Y9502U+cys-AtClo1s, Z5567U+cys-AtClo1s, Z5567U+cys-AtClo1s::PDAT, Z5567U+PDAT::cys-AtClo1s, Z5567U+cys-AtClo1s::LPCAT and Z5567U+LPCAT::cys-AtClo1s.

The AtClo1s coding sequence (SEQ ID NO:33) was modified to encode additional cysteine codons in the N- and C-terminal regions of the AtClo1s polypeptide. This mutated, multiple cysteine-containing polypeptide (SEQ ID NO:51) was designated as "cys-AtClo1s" and is encoded by SEQ ID NO:50. FIG. 2 shows an alignment of the amino acid sequences of AtClo1s (SEQ ID NO:2) and cys-AtClo1s (SEQ ID NO:51). Four and three residues at the N- and C-terminal regions of AtClo1s, respectively, were mutated to cysteine residues. The resulting amino acid sequence (SEQ ID NO:51) contains mutations D11C, H25C, R35c and Q46C in the N-terminal region, and mutations G200C, R207c and D240C in the C-terminal region. In addition, one cysteine residue was inserted between Gly2 and Ser3. The added cysteine residues are underlined in the cys-AtClo1s sequence shown in FIG. 2. The AtClo1s polypeptide contains naturally occurring cysteine residues at amino acid positions 221 and 230. Therefore, cys-AtClo1s contains five cysteine residues in each of its N- and C-terminal regions; these cysteines are spaced from each other at approximately 10-amino acid (7 to 15 amino acids) intervals.

Next, four nucleotide sequences were prepared for expressing cys-AtClo1s fused to *Y. lipolytica* phospholipid:diacylglycerol acyltransferase (PDAT, E.G. 2.3.1.158; U.S. Pat. No. 7,901,928, incorporated herein by reference) or *Y. lipolytica* lysophosphatidylcholine acyltransferase (LPCAT, E.G. 2.3.1.23; U.S. Pat. Appl. Publ. No. 2010-0317882, incorporated herein by reference). The encoded fusion proteins were (i) cys-AtClo1s N-terminal to PDAT (designated as "cys-AtClo1s::PDAT") (SEQ ID NO:53), (ii) cys-AtClo1s C-terminal to PDAT (designated as "PDAT::cys-AtClo1s") (SEQ ID NO:55), (iii) cys-AtClo1s N-terminal to LPCAT (designated as "cys-AtClo1s::LPCAT") (SEQ ID NO:57), and (iv) cys-AtClo1s C-terminal to LPCAT (designated as "LPCAT::cys-AtClo1s") (SEQ ID NO:59) fusion proteins. There was a 24-amino acid linker sequence (GAGPARPA-GLPPATYYDSLAVMGS, SEQ ID NO:60) between the partners in each fusion sequence. The stop codon of the first protein in each fusion was removed. In each of fusion proteins PDAT::cys-AtClo1s (SEQ ID NO:55) and LPCAT::cys-AtClo1s (SEQ ID NO:59), the glycine residue at position 2 of cys-AtClo1s is absent. Also, for each of the four fusion sequences, NcoI and NotI sites were incorporated, respectively, around the translation initiation codon of the first gene and after the stop codon of the second gene. Each sequence was synthesized by GenScript Corporation (Piscataway, N.J.). Note that the NcoI and NotI sites are not shown in SEQ ID NOs:52, 54, 56 and 58, which encode the above fusion proteins.

Construction of Plasmids for Overexpressing Cys-AtClo1s and Linking to PDAT or LPCAT: Plasmids for overexpressing cys-AtClo1s, cys-AtClo1s::PDAT, PDAT::cys-AtClo1s, cys-AtClo15:1 PCAT and LPCAT::cys-AtClo1s were prepared using pYRH55 (FIG. 1, SEQ ID NO:43). Each coding sequence for these proteins was digested with NcoI/NotI and the resulting fragment was used to replace the NcoI/NotI fragment (i.e., AtClo1s insert) of pYRH55. The resulting constructs, pYRH95 (SEQ ID NO:61), pYRH96 (SEQ ID NO:62), pYRH97 (SEQ ID NO:63), pYRH98 (SEQ ID NO:64) and pYRH99 (SEQ ID NO:65), contained a chimeric gene having the coding sequence for cys-AtClo1s, cys-AtClo1s::PDAT, PDAT::cys-AtClo1s, cys-AtClo1s::LPCAT or LPCAT::cys-AtClo1s, respectively, along with the FBAINm promoter (above) and the PEX20 terminator (above). Thus, pYRH95, pYRH96, pYRH97, pYRH98 and pYRH99 only differ from each other with respect to the particular cysteine-modified caleosin/fusion coding sequence contained in each construct.

Generation of *Y. lipolytica* Strains Y9502U+cys-AtClo1s, Z5567U+cys-AtClo1s, Z5567U+cys-AtClo1s::PDAT, Z5567U+PDAT::cys-AtClo1s, Z5567U+cvs-AtClo1s::LPCAT, and Z5567U+LPCAT::cvs-AtClo1s: To overexpress cys-AtClo1s, cys-AtClo1s::PDAT, PDAT::cys-AtClo1s, cys-AtClo1s:IPCAT or LPCAT::cys-AtClo1s in *Y. lipolytica* strain Z9502U or Z5567U, pYRH95, pYRH96, pYRH97, pYRH98 and pYRH99 were each individually digested with AscI/SphI and the larger fragment (of the two fragments resulting from each digestion) was used for transformation (as described in General Methods). The individual transformations yielded strains Y9502U+cys-AtClo1s, Z5567U+cys-AtClo1s, Z5567U+cys-AtClo1s::PDAT, Z5567U+PDAT::cys-AtClo1s, Z5567U+cys-AtClo1s::LPCAT and Z5567U+LPCAT::cys-AtClo1s.

Example 10

Comparison of Oil Production by Strains Y9502U+AtClo1s and Y9502U+cys-AtClo1s

The effect of overexpressing a caleosin having multiple cysteine residues in its N- and C-terminal regions (cys- AtClo1s) on oil accumulation in strain Y9502 was determined. This analysis was done in comparison to the oil accumulation measured in strain Y9502U+AtClo1s and the parent strain lacking caleosin expression.

To evaluate and compare the effects of AtClo1s and cys-AtClo1s overexpression on oil content and fatty acid (FA) composition in *Y. lipolytica*, strains Y9502 (control), Y9502U+AtClo1s and Y9502U+cys-AtClo1s were grown under comparable oleaginous conditions. The DCW, total lipid content of cells [TFAs % DCW] and the concentration of each fatty acid as a weight percent of TFAs [% TFAs] for each of the strains were determined as described in General Methods. The results are shown in Table 8.

Due to the positional effects of random integration of the overexpression constructs in the *Y. lipolytica* genome, oil accumulation results for four out of eight of each of the transformed strains were chosen for the analysis; the selection of each set of transformants was based on a higher EPA titer [EPA % DCW] compared to the other four transformants.

TABLE 8

Lipid Content and Composition in *Y. lipolytica* Strains Y9502, Y9502U + AtClo1s and Y9502U + cys-AtClo1s

| Strain | DCW (g/L) | TFAs % DCW | % TFAs | | | | EPA % DCW |
|---|---|---|---|---|---|---|---|
| | | | 18:0 | 18:1 | 18:2 | EPA | |
| Y9502 | 3.42 | 35.1 | 1.8 | 4.3 | 12.8 | 54.0 | 19.0 |
| | 3.52 | 33.6 | 1.7 | 4.3 | 12.8 | 54.1 | 18.2 |
| AVG | 3.47 | 34.4 | 1.8 | 4.3 | 12.8 | 54.1 | 18.6 |
| Y9502U + AtClo1s | 3.96 | 37.0 | 1.8 | 3.8 | 11.9 | 54.9 | 20.3 |
| | 3.62 | 37.0 | 2.5 | 4.0 | 12.1 | 54.6 | 20.2 |
| | 3.76 | 38.0 | 2.3 | 3.9 | 12.1 | 54.7 | 20.8 |
| | 3.88 | 36.7 | 2.4 | 4.0 | 12.2 | 54.5 | 20.0 |
| AVG | 3.81 | 37.2 | 2.3 | 3.9 | 12.1 | 54.7 | 20.3 |
| Y9502U + cys-AtClo1s | 3.72 | 34.5 | 1.8 | 3.7 | 12.3 | 55.0 | 19.0 |
| | 4.16 | 36.5 | 1.8 | 4.4 | 13.2 | 53.9 | 19.7 |
| | 3.88 | 34.8 | 2.2 | 3.9 | 12.3 | 54.3 | 18.9 |
| | 3.92 | 35.3 | 2.3 | 3.8 | 11.9 | 54.9 | 19.4 |
| AVG | 3.92 | 35.3 | 2.0 | 4.0 | 12.4 | 54.5 | 19.3 |

The results in Table 8 show that overexpression of AtClo1s in Y9502U increased the quantity of oil measured as total lipid content [TFAs % DCW] by approximately 8% and increased the EPA titer [EPA % DCW] by approximately 9% relative to the respective values measured in Y9502. These results confirmed those observed in Example 5 (Table 5): oil content and EPA titer were higher in Y9502U+AtClo1s when compared to Y9502.

However, compared to Y9502U+AtClo1 s, Y9502U overexpressing cys-AtClo1 s showed less of an increase in oil quantity (about 2.6%) and EPA titer (about 3.8%) over the respective values measured in Y9502. While cys-AtClo1s overexpression resulted in a more modest effect on oil quantity compared to when the corresponding non-cysteine-modified caleosin was overexpressed in Y9502U, cys-AtClo1 s was associated with more significant increases in oil quantity when expressed in a different strain (Z5567U) or as a fusion protein with PDAT (below).

Example 11

Oil Production by Strains Z5567U+cys-AtClo1s, Z5567U+cys-AtClo1s::PDAT, Z5567U+PDAT::cys-AtClo1s, Z5567U+cys-AtClo1s::LPCAT and Z5567U+LPCAT::cys-AtClo1s The effect of overexpressing caleosin having multiple added cysteine residues (cys-AtClo1s) on oil accumulation in strain Z5567 was tested. In particular, accumulated oil levels were measured in Z5567U+cys-AtClo1s, Z5567U+cys-AtClo1s::PDAT, Z5567U+PDAT::cys-AtClo1s, Z5567U+cys-AtClo1s::LPCAT and Z5567U+LPCAT::cys-AtClo1s and compared to the oil level of the parent strain (Z5567) which lacked caleosin expression. Both cys-AtClo1s::PDAT and PDAT::cys-AtClo1s fusion protein overexpression resulted in significantly increased oil measured as a percent of the total dry cell weight [TFAs % DCW] compared to cells lacking caleosin expression.

To evaluate and compare the effects of caleosin overexpression on oil content and fatty acid (FA) composition in *Y. lipolytica*, strains Z5567 (control), Z5567U+cys-AtClo1s, Z5567U+cys-AtClo1s::PDAT, Z5567U+PDAT::cys-AtClo1s, Z5567U+cys-AtClo1s::LPCAT and Z5567U+LPCAT::cys-AtClo1s were grown under comparable oleaginous conditions. The DCW, total lipid content of cells [TFAs % DCW] and the concentration of each fatty acid as a weight percent of TFAs [% TFAs] for each of the strains were determined as described in General Methods. The results are shown in Tables 9 and 10.

For each caleosin overexpression strain, eight or sixteen transformants were analyzed depending on the background level growth of Z5567U on a control plate lacking uracil. Results for 4 out of 8 or 5 out of 16 of each of the transformed strains were chosen for the analysis; the selection of each set of transformants was based on a higher total lipid content or EPA titer compared to the other transformants for each strain.

TABLE 9

Lipid Content and Composition in *Y. lipolytica* Strains Z5567, Z5567U + cys-AtClo1s, Z5567U + cys-AtClo1s::PDAT, Z5567U + PDAT::cys-AtClo1s

| Strain | DCW (g/L) | TFAs % DCW | % TFAs | | | | EPA % DCW |
|---|---|---|---|---|---|---|---|
| | | | 18:0 | 18:1 | 18:2 | EPA | |
| Z5567 | 5.10 | 47.6 | 2.2 | 6.7 | 15.9 | 46.7 | 22.2 |
| | 5.04 | 47.3 | 2.2 | 6.7 | 16.1 | 46.4 | 22.0 |
| AVG | 5.07 | 47.5 | 2.2 | 6.7 | 16.0 | 46.6 | 22.1 |
| Z5567U + cys-AtClo1s | 3.58 | 49.6 | 2.2 | 0.9 | 15.0 | 47.1 | 23.4 |
| | 3.16 | 51.8 | 2.3 | 0.7 | 16.5 | 47.2 | 24.5 |
| | 2.74 | 47.2 | 2.2 | 0.7 | 12.9 | 51.8 | 24.5 |
| | 3.22 | 51.7 | 2.4 | 0.8 | 15.5 | 48.5 | 25.1 |
| AVG | 3.18 | 50.1 | 2.3 | 0.7 | 15.0 | 48.7 | 24.4 |
| Z5567U + cys-AtClo1s::PDAT | 4.40 | 55.8 | 3.7 | 7.0 | 22.6 | 36.1 | 20.1 |
| | 3.20 | 51.7 | 2.5 | 4.6 | 14.3 | 50.3 | 26.0 |
| | 3.30 | 52.2 | 2.8 | 5.1 | 15.4 | 48.6 | 25.3 |
| | 3.36 | 54.8 | 2.1 | 5.0 | 15.0 | 49.6 | 27.2 |
| | 4.02 | 55.7 | 4.0 | 7.0 | 22.7 | 36.4 | 20.3 |
| AVG | 3.66 | 54.0 | 3.0 | 5.7 | 18.0 | 44.2 | 23.8 |
| Z5567U + PDAT::cys-AtClo1s | 3.26 | 53.3 | 2.5 | 4.9 | 15.1 | 49.2 | 26.2 |
| | 4.32 | 54.8 | 4.0 | 7.1 | 23.1 | 35.9 | 19.6 |
| | 2.94 | 52.2 | 3.0 | 5.9 | 16.1 | 46.6 | 24.3 |
| | 3.02 | 55.6 | 2.7 | 5.5 | 15.8 | 46.6 | 25.9 |
| | 3.88 | 56.2 | 4.0 | 7.5 | 23.4 | 35.3 | 19.8 |
| AVG | 3.48 | 54.4 | 3.2 | 6.2 | 18.7 | 42.7 | 23.2 |

The results in Table 9 show that overexpression of cys-AtClo1s in Z5567U increased the quantity of oil measured as lipid content [TFAs % DCW] by approximately 5% over the total lipid content of control strain Z5567. Also, cys-AtClo1s overexpression in Z5567U increased the average EPA titer [EPA % DCW] by approximately 10% compared to the EPA titer of Z5567.

Thus overexpression of a caleosin modified to contain additional cysteines (cys-AtClo1s) increased oil content in a recombinant oleaginous *Yarrowia* strain (Z5567) that, without caleosin overexpression, accumulated oil to about 47.5% on a dry cell weight basis (TFAs % DCW, Table 9). Therefore, this represents another example of how overexpression of a caleosin polypeptide can increase the oil content of a recombinant oleaginous microorganism that comprises a polyunsaturated fatty acid biosynthetic pathway and that produces at least 25% of its dry cell weight as oil.

Given that the effects of cys-AtClo1s expression are fairly similar between strains Z5567U and Y9502U, it is reasonable to expect that expression of the corresponding caleosin not modified to contain additional cysteines (i.e., AtClo1s) would induce an equal or higher level of oil accumulation in Z5567U compared to that induced by cys-AtClo1s. This is because, while cys-AtClo1s overexpression increased oil content in Y9502U relative to Y9502 by about 2.6%, the elevation of oil content in Y9502U was greater when AtClo1s was overexpressed (about 8%, Table 8).

Overexpression of cys-AtClo1s::PDAT or PDAT::cys-AtClo1s in Z5567U significantly increased the quantity of oil by about 14-15% and the EPA titer by about 5-8%, compared to the respective values measured for control strain Z5567. This represents an example showing that caleosin can be fused to certain other proteins at its N- or C-terminus and retain its ability to induce increased oil content. While the caleosin in this example was cysteine-modified, it is expected that overexpression of a non-cysteine-modified caleosin in fusion with PDAT would be able to increase oil and EPA content. These results altogether demonstrate that overexpressing a caleosin protein in fusion with an enzyme that catalyzes acylation of diacylglycerol, such as PDAT, can increase oil content in a recombinant oleaginous microorganism that comprises a polyunsaturated fatty acid biosynthetic pathway and that produces at least 25% of its dry cell weight as oil.

TABLE 10

Lipid Content and Composition in Y. lipolytica Strains Z5567, Z5567U + cys-AtClo1s::LPCAT, Z5567U + LPCAT::cys-AtClo1s

| Strain | DCW (g/L) | TFAs % DCW | % TFAs 18:0 | 18:1 | 18:2 | EPA | EPA % DCW |
|---|---|---|---|---|---|---|---|
| Z5567 | 3.18 | 50.9 | 2.4 | 6.0 | 15.9 | 47.1 | 24.0 |
| | 3.10 | 53.8 | 2.6 | 5.9 | 16.2 | 47.3 | 25.4 |

TABLE 10-continued

Lipid Content and Composition in Y. lipolytica Strains Z5567, Z5567U + cys-AtClo1s::LPCAT, Z5567U + LPCAT::cys-AtClo1s

| Strain | DCW (g/L) | TFAs % DCW | % TFAs 18:0 | 18:1 | 18:2 | EPA | EPA % DCW |
|---|---|---|---|---|---|---|---|
| AVG | 3.14 | 52.4 | 2.5 | 6.0 | 16.1 | 47.2 | 24.7 |
| Z5567U + cys-AtClo1s::LPCAT | 3.04 | 52.0 | 2.6 | 5.8 | 16.1 | 46.9 | 24.4 |
| | 3.02 | 50.9 | 2.9 | 5.8 | 16.5 | 46.5 | 23.7 |
| | 3.16 | 46.1 | 2.1 | 5.0 | 13.0 | 49.9 | 23.0 |
| | 2.74 | 49.1 | 1.9 | 5.0 | 12.8 | 49.2 | 24.2 |
| | 2.56 | 45.8 | 2.2 | 4.6 | 13.8 | 50.4 | 23.1 |
| AVG | 2.90 | 48.8 | 2.3 | 5.2 | 14.4 | 48.6 | 23.7 |
| Z5567U + LPCAT::cys-AtClo1s | 3.60 | 54.9 | 4.1 | 7.2 | 23.0 | 35.8 | 19.6 |
| | 3.54 | 50.6 | 2.3 | 4.8 | 15.2 | 49.8 | 25.2 |
| | 2.98 | 54.4 | 2.4 | 6.0 | 16.0 | 47.1 | 25.7 |
| | 3.08 | 49.6 | 3.0 | 5.4 | 15.8 | 47.7 | 23.7 |
| | 2.74 | 48.0 | 1.9 | 4.9 | 12.5 | 49.7 | 23.9 |
| AVG | 3.19 | 51.5 | 2.7 | 5.7 | 16.5 | 46.0 | 23.6 |

The results in Table 10 show that overexpression of cys-AtClo1s::LPCAT or LPCAT::cys-AtClo1s in Z5567U did not increase the quantity of oil measured as total lipid content [TFAs % DCW] or EPA titer [EPA % DCW] compared to the respective values of control strain Z5567.

This result indicates that the particular cys-caleosin/LPCAT fusion proteins tested herein (cys-AtClo1s::LPCAT, SEQ ID NO:64; LPCAT::cys-AtClo1s, SEQ ID NO:65) may not be useful for increasing oil content in oleaginous microorganisms comprising a polyunsaturated fatty acid biosynthetic pathway and that produces at least 25% of its dry cell weight as oil, such as Y. lipolytica strain Z5567. This result is in direct contrast to the results obtained using the cys-AtClo1s::PDAT and PDAT::cys-AtClo1s fusion proteins (Table 9), which were able to significantly increase oil content by up to 15% in Y. lipolytica strain Z5567U.

What is claimed is:

1. A recombinant oleaginous *Yarrowia lipolytica* that produces at least 25% of its dry cell weight as oil, wherein said recombinant oleaginous *Yarrowia lipolytica* comprises a functional polyunsaturated fatty acid biosynthetic pathway and at least one genetic construct encoding a caleosin polypeptide comprising the amino acid sequence of SEQ ID NO:2;
further wherein said recombinant oleaginous *Yarrowia lipolytica* comprises at least 35% eicosapentaenoic acid as a weight percentage of total fatty acids of the *Yarrowia lipolytica*.

2. The recombinant oleaginous microorganism of claim 1, wherein the caleosin polypeptide is linked to an enzyme that catalyzes acylation of diacylglycerol.

3. The recombinant oleaginous microorganism of claim 2, wherein said enzyme is a phospholipid:diacylglycerol acyltransferase (PDAT).

4. A method for increasing the amount of oil contained in a recombinant oleaginous *Yarrowia lipolytica*, said method comprising the steps of:
a) providing a recombinant oleaginous *Yarrowia lipolytica* according to claim 1;
b) growing the recombinant oleaginous *Yarrowia lipolytica* of step (a) under conditions whereby said oil is produced; and
c) optionally, recovering the oil of step (b).

5. The recombinant oleaginous *Yarrowia lipolytica* of claim 1, wherein the *Yarrowia lipolytica* comprises at least 45% eicosapentaenoic acid as a weight percentage of the total fatty acids.

6. The recombinant oleaginous *Yarrowia lipolytica* of claim 3, wherein the PDAT is *Yarrowia lipolytica* PDAT.

7. The method of claim 4, wherein the *Yarrowia lipolytica* comprises at least 45% eicosapentaenoic acid as a weight percentage of the total fatty acids.

* * * * *